US011407752B2

(12) United States Patent
Zhou et al.

(10) Patent No.: US 11,407,752 B2
(45) Date of Patent: Aug. 9, 2022

(54) SUBSTITUTED 4,6-DIHYDROSPIRO [[1,2,3]TRIAZOLO[4,5-B]PYRIDINE-7,3'-INDOLINE]-2',5(3H)-DIONE ANALOGUES

(71) Applicants: Jia Zhou, Galveston, TX (US); Pei-Yong Shi, Galveston, TX (US); Jimin Xu, Galveston, TX (US); Xuping Xie, Galveston, TX (US)

(72) Inventors: Jia Zhou, Galveston, TX (US); Pei-Yong Shi, Galveston, TX (US); Jimin Xu, Galveston, TX (US); Xuping Xie, Galveston, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 187 days.

(21) Appl. No.: 16/938,886

(22) Filed: Jul. 24, 2020

(65) Prior Publication Data

US 2021/0047329 A1    Feb. 18, 2021

Related U.S. Application Data

(60) Provisional application No. 62/879,076, filed on Jul. 26, 2019.

(51) Int. Cl.
*C07D 471/20* (2006.01)
*C07D 495/04* (2006.01)
*A61P 31/14* (2006.01)

(52) U.S. Cl.
CPC ............ *C07D 471/20* (2013.01); *A61P 31/14* (2018.01); *C07D 495/04* (2013.01)

(58) Field of Classification Search
CPC ...... C07D 471/20; C07D 495/04; A61P 31/14
See application file for complete search history.

(56) References Cited

FOREIGN PATENT DOCUMENTS

WO    2014167528 A1    10/2014

OTHER PUBLICATIONS

Berge et al., Pharmaceutical Salts, J. Pharm. Sci., (1977) 66:1-19.
Dengue Vaccine: WHO Position Paper—Sep. 2018. Weekly Epidemiological Record. World Health Organization: Geneva. 2018; vol. 93: pp. 457-476.
Xu et al., Design, synthesis and biological evaluation of spiropyrazolopyridone derivatives as potent dengue virus inhibitors. Bioorganic & Medicinal Chemistry Letters, Jun. 1, 2020; 30(11):127162.
Verdonck et al., Synthesis and Structure-Activity Relationships of 3,5-Disubstituted-pyrrolo[2,3-beta]Pyridines as Inhibitors of Adaptor-Associated Kinase 1 with Antiviral Activity, J. Med. Chem. 2019, 62, 5810-5831.
Bardiot et al., Discovery of Indole Derivatives as Novel and Potent Dengue Virus Inhibitors, Journal of Medicinal Chemistry, 2018, 61, 8390-8401.
Beesetti et al., Drugs for dengue: a patent review (2010-2014), Expert Opinion on Therapeutic Patents, 24:11, 1171-1184, DOI: 10.1517/13543776.2014.967212.
Behnam et al., The Medicinal Chemistry of Dengue Virus, Journal of Medicinal Chemistry, 2016, 59, 5622-5649.
Bhatt et al., The global distribution and burden of dengue, Nature, vol. 496, Apr. 25, 2013, 504-507.
Brady et al., Refining the Global Spatial Limits of Dengue Virus Transmission by Evidence-Based Consensus, PLOS Neglected Tropical Diseases, Aug. 2012, vol. 6, Issue 8, e1760, 227 pages.
Chao et al., Discovery and Optimization of 2,4-Diaminoquinazoline Derivatives as a New Class of Potent Dengue Virus Inhibitors, Journal of Medicinal Chemistry, 2012, 55, 3135-3143.
Dengue vaccine: WHO position paper—Sep. 2018, Weekly Epidemiological Record, No. 36, Sep. 7, 2018, 21 pgs.
Dengue, Guidelines for Diagnosis, Treatment, Prevention and Control, World Health Organization 2009, 160 pages.
Endy et al., Prospective Cohort Studies of Dengue Viral Transmission and Severity of Disease, Current topics in microbiology and immunology, Jan. 2010, 14 pgs.
Global Advisory Committee on Vaccine Safety, Jun. 6-7, 2018, Weekly Epidemiological Record, No. 29/30, Jul. 20, 2018, 8 pgs.
Global strategy for dengue prevention and control 2012-2020, World Health Organization 2012, 43 pgs.
Graham et al., A Prospective Seroepidemiologic Study on Dengue in Children Four to Nine Years of Age in Yogyakarta, Indonesia I. Studies in 1995-1996, The American Society of Tropical Medicine and Hygiene, 61(3), 1999, pp. 412-419.
Guzman et al., Dengue, Lancet, Jan. 31, 2015, vol. 385: 453-65.
Guzman et al., Secondary infection as a risk factor for dengue hemorrhagic fever/dengue shock syndrome: an historical perspective and role of antibody-dependent enhancement of infection, Springer, Arch Virol (2013) 158:1445-1459.
Halsey et al., Correlation of Serotype-Specific Dengue Virus Infection with Clinical Manifestations, PLOS Neglected Tropical Diseases, May 2012, vol. 6, Issue 5, e1638, 10 pgs.
Informing Vaccination Programs: A Guide to the Design and Conduct of Dengue Serosurveys, Immunization, Vaccines and Biologicals, World Health Organization 2017, 50 pgs.
Jentes et al., Evidence-based risk assessment and communication: a new global dengue-risk map for travellers and clinicians, Journal of Travel Medicine, 2016, vol. 23, No. 6, 5 pgs.
Kounde et al., Discovery of 2-oxopiperazine dengue inhibitors by scaffold morphing of a phenotypic high-throughput screening hit, Bioorganic & Medicinal Chemistry Letters 27 (2017) 1385-1389.
Li et al., Genetic interaction between NS4A and NS4B for replication of Japanese encephalitis virus, Journal of General Virology (2015), 96, 1264-1275.
Li et al., Secondary Structure and Membrane Topology of the Full-Length Dengue Virus NS4B in Micelles, Angew. Chem. 2016, 128, 12247-12251.
Lim et al., Ten years of dengue drug discovery: Progress and prospects, Antiviral Research 100 (2013) 500-519.

(Continued)

*Primary Examiner* — Laura L Stockton
(74) *Attorney, Agent, or Firm* — Hylton-Rodic Law PLLC

(57) ABSTRACT

A series of substituted 4,6-dihydrospiro[[1,2,3]triazolo[4,5-b]pyridine-7,3'-indoline]-2',5(3H)-dione analogues, the use thereof and the preparation thereof.

16 Claims, 11 Drawing Sheets

(56) References Cited

OTHER PUBLICATIONS

Messina et al., Global spread of dengue virus types: mapping the 70 year history, Trends in Microbiology, Mar. 2014, vol. 22, No. 3, 9 pgs.
Montoya et al., Symptomatic Versus Inapparent Outcome in Repeat Dengue Virus Infections Is Influenced by the Time Interval between Infections and Study Year, PLOS Neglected Tropical Diseases, Aug. 2013, vol. 7, Issue 8, e2357, 10 pgs.
Munoz-Jordan et al., Inhibition of Alpha/Beta Interferon Signaling by the NS4B Protein of Flaviviruses, Journal of Virology, vol. 79, No. 13, Jul. 2005, p. 8004-8013.
Munoz-Jordan et al., Inhibition of interferon signaling by dengue virus, PNAS, Nov. 25, 2003, vol. 100, No. 24, 14333-14338.
Nitsche et al., Biochemistry and Medicinal Chemistry of the Dengue Virus Protease, Chemical Reviews, 2014, 114, 11348-11381.
Noble et al., Structural biology of dengue virus enzymes: Towards rational design of therapeutics, Antiviral Research 96 (2012) 115-126.
Patkar et al., Identification of Inhibitors of Yellow Fever Virus Replication Using a Replicon-Based High-Throughput Assay, Antimicrobial Agents and Chemotherapy, Oct. 2009, p. 4103-4114, vol. 53, No. 10.
Reich et al., Interactions between serotypes of dengue highlight epidemiological impact of cross-immunity, 2013, J R Soc Interface 10:Apr. 14, 2013, 9 pgs.
Rocha et al., Dengue-specific serotype related to clinical severity during the 2012/2013 epidemic in centre of Brazil, Infectious Diseases of Poverty (2017) 6:116, 11 pgs.
Sangkawibha et al., Risk Factors in Dengue Shock Syndrome: a Prospective Epidemiologic Study in Rayong, Thailand, American Journal of Epidemiology, vol. 120, Nov. 1984, No. 5, 17 pgs.
Stanaway et al., The global burden of dengue: an analysis from the Global Burden of Disease Study 2013, Lancet Infect Dis, Jun. 2016; vol. 16: 712-23.
Stevens et al., The Medicinal Chemistry of Dengue Fever, J. Med. Chem. 2009, 52, 7911-7926.
Tajima et al., Restoration of replication-defective dengue type 1 virus bearing mutations in the N-terminal cytoplasmic portion of NS4A by additional mutations in NS4B, Springer, Arch Virol (2011) 156:63-69.
Thein et al., Risk Factors in Dengue Shock Syndrome, Am. J. Trop. Med. Hyg., 56(5), 1997, pp. 566-572.
Umareddy et al., Dengue virus NS4B interacts with NS3 and dissociates it from single-stranded RNA, Journal of General Virology (2006), 87, 2605-2614.
Van Cleef et al., Identification of a new dengue virus inhibitor that targets the viral NS4B protein and restricts genomic RNA replication, Antiviral Research 99 (2013) 165-171.
Vannice et al., Clinical development and regulatory points for consideration for second-generation live attenuated dengue vaccines, Vaccine 36 (2018) 3411-3417.
Verdonck et al., Synthesis and Structure?Activity Relationships of 3,5-Disubstituted pyrrolo[2,3?b]pyridines as Inhibitors of Adaptor-Associated Kinase 1 with Antiviral Activity, J. Med. Chem. 2019, 62, 5810-5831.
Wang et al., Discovery of Dengue Virus NS4B Inhibitors, Journal of Virology, Aug. 2015 vol. 89 No. 16, 12 pgs.
Wang et al., Proteolysis Targeting Chimera (PROTAC): A Paradigm-Shifting Approach in Small Molecule Drug Discovery, Current Topics in Medicinal Chemistry, 2018, 18, 1354-1356.
Whitehorn et al., The pathogenesis of dengue, Vaccine 29 (2011) 7221-7228.
Xie et al., Generation and characterization of mouse monoclonal antibodies against NS4B protein of dengue virus, Virology 450-451 (2014) 250-257.
Xie et al., Inhibition of Dengue Virus by Targeting Viral NS4B Protein, Journal of Virology, Nov. 2011, vol. 85, No. 21, p. 11183-11195.
Xie et al., Targeting dengue virus NS4B protein fordrug discovery, Antiviral Research 118 (2015) 39-45.
Xie et al., Understanding Zika Virus Stability and Developing a Chimeric Vaccine through Functional Analysis, American Society for Microbiology, Jan./Feb. 2017, vol. 8, Issue 1, e02134-16, 14 pgs.
Xie et al., Zika Virus Replicons for Drug Discovery, EBioMedicine 12 (2016) 156-160.
Yang et al., Discovery, Optimization, and Target Identification of Novel Potent Broad-Spectrum Antiviral Inhibitors, J. Med. Chem. 2019, 62, 4056-4073.
Ye et al., Therapeutic Potential of Spirooxindoles as Antiviral Agents, ACS Infect. Dis. 2016, 2, 382-392.
Yokokawa et al., Discovery of Potent Non-Nucleoside Inhibitors of Dengue Viral RNA-Dependent RNA Polymerase from a Fragment Hit Using Structure-Based Drug Design, J. Med. Chem. 2016, 59, 3935-3952.
Youn et al., Evidence for a Genetic and Physical Interaction between Nonstructural Proteins NS1 and NS4B That Modulates Replication of West Nile Virus, Journal of Virology, Jul. 2012, vol. 86, No. 13, p. 7360-7371.
Yung et al., Dengue Serotype-Specific Differences in Clinical Manifestation, Laboratory Parameters and Risk of Severe Disease in Adults, Singapore, Am. J. Trop. Med. Hyg., 92(5), 2015, pp. 999-1005.
Zou et al., Characterization of Dengue Virus NS4A and NS4B Protein Interaction, Apr. 2015, vol. 89, No. 7, Journal of Virology, 16 pgs.
Zou et al., Dimerization of Flavivirus NS4B Protein, Mar. 2014, vol. 88, No. 6, Journal of Virology, p. 3379-3391.
Zou et al., Lead Optimization of Spiropyrazolopyridones: a New and Potent Class of Dengue Virus Inhibitors, ACS Med. Chem. Lett. 2015, 6, 344-348.
Zou et al., Mapping the Interactions between the NS4B and NS3 Proteins of Dengue Virus, Apr. 2015, vol. 89, No. 7, Journal of Virology, 13 pgs.

Antiviral antivity and cytotoxicity

| Cmpd | DENV-2 replicon cell (EC$_{50}$, μM) | DENV-3 replicon cell (EC$_{50}$, μM) | Huh7 cell (CC$_{50}$, μM) |
|---|---|---|---|
| 73 | 0.0414 | 0.0167 | >10 |
| 75 | >5 | >5 | >10 |

| Isolates | Selection | Mutations | EC$_{50}$ | Resistance fold |
|---|---|---|---|---|
| P12-I | DMSO | NS3 T606A | 48 nM | 0.80 |
| P12-II | | NS3 T606A | 56 nM | 0.93 |
| P12-III | | NS3 T606A; NS4B V63M | > 6000 nM | >100 |
| P12-IV | Compound 63 | NS4B V63M; | > 6000 nM | >100 |
| P12-V | | NS4B V63M; NS4B P104S | > 6000 nM | >100 |
| P12-VI | | NS3 T606A; NS4B V63L | > 6000 nM | >100 |
| P0 DENV-2 | -- | -- | 60 nM | -- |

…

SUBSTITUTED 4,6-DIHYDROSPIRO [[1,2,3]TRIAZOLO[4,5-B]PYRIDINE-7,3'-INDOLINE]-2',5(3H)-DIONE ANALOGUES

CROSS-REFERENCE TO RELATED APPLICATIONS

This application claims the benefit of U.S. Provisional Appl. No. 62/879,076, filed Jul. 26, 2019. The content of the foregoing application is relied upon and is incorporated by reference herein in its entirety.

FIELD OF THE INVENTION

The field of the invention relates generally to 4,6-dihydrospiro[[1,2,3]triazolo[4,5-b]pyridine-7,3'-indoline]-2',5(3h)-dione analogues, the preparation and use thereof.

BRIEF DESCRIPTION OF THE FIGURES

FIG. 1A-C. Antiviral activity, cytotoxicity and the association with NS4B of the biotinylated compounds. (A) Chemical structures of biotinylated compound (R,S)-73 and its (S,S)-diastereoisomer 75. (B) Antiviral activity and cytotoxicity of compound 73 and 75 in cell culture. (C) Compound 73 is associated with DENV-2 viral NS4B protein. NS4B in the cell lysates and eluates were detected by Western blot using a mouse monoclonal antibody against DENV-2 NS4B protein.

FIG. 2A-2C. Mutations in NS4B confer to viral resistance to the inhibition by this series of compounds. (A) Scheme of selection and validation of resistant viruses. See details in the Method. DENV-2 strain NGC was used for the selection on Huh7 cells. (B) Resistant profile of P12 mutant viruses. Mutations at position V63 of DENV-2 NS4B were consistently recovered from four independent selections. DMSO (0.45%) was used as a negative control during resistance selection. The resistance fold was calculated by comparing the sensitivities (indicated by $EC_{50}$) of the resistant virus to the that of the PO DENV-2. (C) Sensitivity of P12-VI to the treatment of compound 15. $EC_{50}$ values were determined by viral reduction assay on Huh7 cells.

DETAILED DESCRIPTION

1.0. Definitions

Figure 1A:
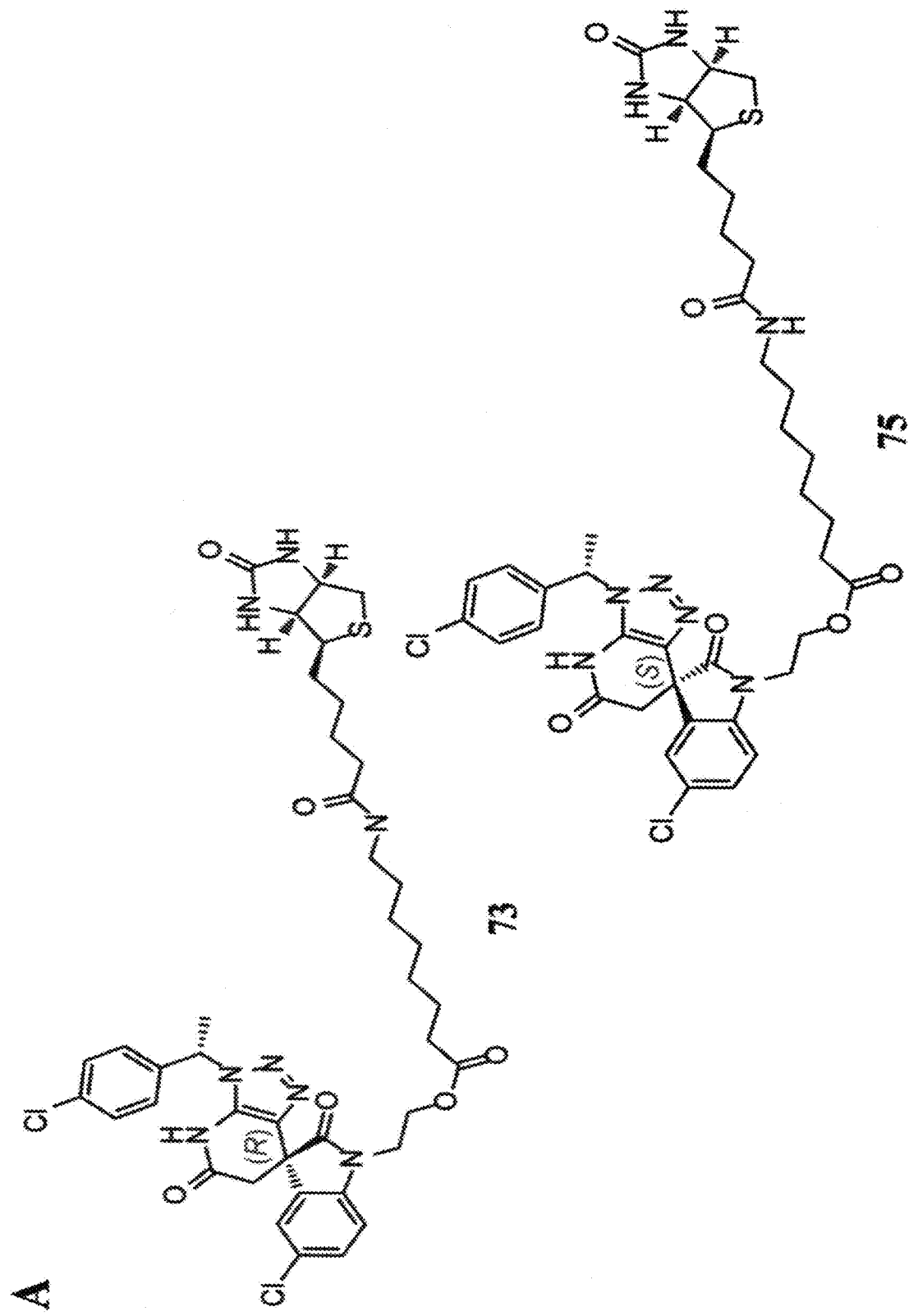

For the purposes of promoting an understanding of the principles of the invention, reference will now be made to certain embodiments and specific language will be used to describe the same. It will nevertheless be understood that no limitation of the scope of the invention is thereby intended, and alterations and modifications in the illustrated invention, and further applications of the principles of the invention as illustrated therein are herein contemplated as would normally occur to one skilled in the art to which the invention relates.

Unless defined otherwise, all technical and scientific terms used herein have the same meaning as commonly understood by one of ordinary skill in the art to which this invention pertains.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used).

The use of "or" means "and/or" unless stated otherwise.

The use of "a" or "an" herein means "one or more" unless stated otherwise or where the use of "one or more" is clearly inappropriate.

The use of "comprise," "comprises," "comprising," "include," "includes," and "including" are interchangeable and not intended to be limiting.

Furthermore, where the description of one or more embodiments uses the term "comprising," those skilled in the art would understand that, in some specific instances, the embodiment or embodiments can be alternatively described using the language "consisting essentially of" and/or "consisting of."

As used herein, the term "about" refers to a ±10% variation from the nominal value. It is to be understood that such a variation is always included in any given value provided herein, whether or not it is specifically referred to.

As used herein, the terms "cell" and "cells" refer to any types of cells from any animal, such as, without limitation, rat, mice, monkey, and human.

The term "alkyl" as used herein by itself or as part of another group refers to both straight and branched chain radicals, and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. The term "alkyl" may include methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, and dodecyl.

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O, and N. The heteroatom(s) may be placed at any interior position of the heteroalkyl group or at the position at which the alkyl group is attached to the remainder of the molecule. Up to two heteroatoms may be consecutive.

The term "alkylene" as used herein refers to straight and branched chain alkyl linking groups, i.e., an alkyl group that links one group to another group in a molecule. In some embodiments, the term "alkylene" may include $(CH_2)_n$— where n is 2-8.

The term "aryl" means a polyunsaturated hydrocarbon substituent. Aryl groups can be monocyclic or polycyclic (e.g., 2 to 3 rings that are fused together or linked covalently). Non-limiting examples of aryl and heteroaryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

The term "heteroaryl" as used herein refers to groups having 5 to 14 ring atoms; 6, 10 or 14 7π-electrons shared in a cyclic array; and containing carbon atoms and 1, 2 or 3 oxygen, nitrogen or sulfur heteroatoms. A heteroaryl group can be attached to the remainder of the molecule through a carbon or heteroatom. Especially preferred heteroaryl groups include 1,2,3-triazole, 1,2,4-triazole, 5-amino 1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, 2-aminopyridine, 4-aminopyridine, 2-aminoimidazoline, and 4-aminoimidazoline.

An "amino" group refers to an —$NH_2$ group.

A "carboxylic acid" group refers to a $CO_2H$ group.

An "alkynyl group" refers to a straight or branched chain radical of 2-20 carbon atoms, unless the chain length is limited thereto, wherein there is at least one triple bond between two of the carbon atoms in the chain, including, but not limited to, acetylene, 1-propylene, 2-propylene, and the like. In some embodiments, "alkynyl group" refers to an alkynyl chain, which is 2 to 10 carbon atoms in length. In other embodiments, "alkynyl group" refers to an alkynyl chain, which is more 2 to 8 carbon atoms in length. In further embodiments, "alkynyl group" refers to an alkynyl chain, which is from 2 to 4 carbon atoms in length.

An "amido" group refers to an —$CONH_2$ group. An alkylamido group refers to an —CONHR group wherein R is a straight chained, or branched alkyl. In some embodiments, R may be taken together with the —(C=O)— group to form a ring, which may be fused with, or bonded to, to a substituted or unsubstituted aryl, heteroaryl, or heterocyclic ring.

A dialkylamido group refers to an —CONRR' group wherein R and R' are may straight-chained, or branched, alkyl or may be taken together to form a ring, which may be fused with, or bonded to, to a substituted or unsubstituted aryl, heteroaryl, or heterocyclic ring.

The term "halogen" or "halo" or "halide" as used herein by itself or as part of another group refers to chlorine, bromine, fluorine or iodine.

The term "hydroxy" or "hydroxyl" as used herein by itself or as part of another group refers to an —OH group.

An "alkoxy" group refers to an —O-alkyl group wherein "alkyl" is as defined above. In one embodiment, the alkyl group has 1-12 carbons. In another embodiment, the alkyl group has 1-7 carbons. In a further embodiment, the alkyl group has 1-6 carbons. In another embodiment, the alkyl group has 1-4 carbons.

The term "heterocycle" or "heterocyclic ring", as used herein except where noted, represents a stable 5- to 7-membered monocyclic-, or stable 7- to 11-membered bicyclic heterocyclic ring system, any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Rings may contain one oxygen or sulfur, one to three nitrogen atoms, or one oxygen or sulfur combined with one or two nitrogen atoms. The heterocyclic ring may be attached at any heteroatom or carbon atom that results in the creation of a stable structure.

The term "alkylamino" as used herein by itself or as part of another group refers to an amino group which is substituted with one alkyl group having from 1 to 6 carbon atoms. The term "dialkylamino" as used herein by itself or as part of another group refers to an amino group which is substituted with two alkyl groups, each having from 1 to 6 carbon atoms.

Various groups are described herein as substituted or unsubstituted (i.e., optionally substituted). Optionally substituted groups may include one or more substituents independently selected from: halogen, nitro, cyano, hydroxy, amino, mercapto, formyl, carboxy, oxo, carbamoyl, alkyl, heteroalkyl, alkoxy, alkylthio, alkylamino, (alkyl)$_2$amino, alkylsulfinyl, alkylsulfonyl, arylsulfonyl, substituted or unsubstituted cycloalkyl, substituted or unsubstituted heterocyclyl, substituted or unsubstituted aryl, and substituted or unsubstituted heteroaryl. In certain aspects, the optional substituents may be further substituted with one or more substituents independently selected from: halogen, nitro, cyano, hydroxy, amino, mercapto, formyl, carboxy, carbamoyl (—C(O)$NR_2$), unsubstituted alkyl, unsubstituted heteroalkyl, alkoxy, alkylthio, alkylamino, (alkyl)$_2$amino, alkylsulfinyl, alkyl sulfonyl, aryl sulfonyl, unsubstituted cycloalkyl, unsubstituted heterocyclyl, unsubstituted aryl, or unsubstituted heteroaryl. Exemplary optional substituents include, but are not limited to: —OH, oxo (=O), —Cl, —F, Br, $C_{1-4}$alkyl, phenyl, benzyl, —$NH_2$, —NH($C_{1-4}$alkyl), —N(C1-4alkyl)$_2$, —$NO_2$, —S($C_{1-4}$alkyl), —$SO_2$($C_{1-4}$alkyl), —$CO_2$($C_{1-4}$alkyl), and —O($C_{1-4}$alkyl).

The term "pharmaceutically acceptable salt" refers to those salts of the compounds of the present invention which are, within the scope of sound medical judgment, suitable for use in contact with the tissues of patients without undue toxicity, and the like. As used herein, the term "pharmaceutically acceptable salt" may include acetate, hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. (See S. M. Barge et al., "Pharmaceutical Salts," J. Pharm. Sci., 66:1-19 (1977)), which is incorporated herein by reference in its entirety, for further examples of pharmaceutically acceptable salt).

The terms "treating," "treatment" and the like as used herein includes the management and care of a subject (preferably a mammal, more preferably a human) for the purpose of combating a disease, condition, or disorder and includes the administration of a compound of the present disclosure to prevent the onset of the symptoms or complications, alleviate the symptoms or complications, or eliminate the disease, condition, or disorder.

The term "subject" as used herein refers to an animal, preferably a mammal, most preferably a human, who has been the object of treatment, observation or experiment. Preferably, the subject has experienced and/or exhibited at least one symptom of the disease or disorder to be treated and/or prevented. Further, a subject may not have exhibited any symptoms of the disorder, disease or condition to be treated and/prevented, but has been deemed by a physician, clinician or other medical professional to be at risk for developing said disorder, disease or condition.

Dengue is a viral disease vectored mainly by female *Aedes* mosquitoes that causes flu-like symptoms with high fever, headache, vomiting, rash and joint/bone/muscle pain, and sometimes it can develop into a potentially life-threatening complication called severe dengue, dengue hemorrhagic fever (DHF) or dengue shock syndrome (DSS).[1] Before 1970, only nine countries had experienced severe dengue epidemics. Today, the disease is widespread globally in more than 100 tropical and subtropical countries, putting almost half of the world's population at risk, and the Americas, South-East Asia and Western Pacific regions are the most seriously affected.[2-4] The incidence of dengue has grown dramatically with a 30-fold increase around the world over the past 50 years.[5] As a vast majority of cases are asymptomatic, the actual numbers of dengue cases are underreported and many cases are misclassified. It is estimated that 390 million dengue infections occur annually, of which 96 million manifest clinically (with any severity of disease), including approximately 500,000 cases of severe dengue and 22,000 deaths worldwide.[6, 7] The burden of dengue is considerable, causing human suffering, strained health services and massive economic losses. However, there remains no effective antiviral therapy for dengue fever, and vector control is the main method to prevent dengue outbreaks.[8-17] Recently, the first dengue vaccine CYD-TDV, developed by Sanofi Pasteur, has been licensed in a number of countries but has limited efficacy and safety issues.[18, 19] Because of this, it is limited to individuals ranging from 9-45 years of age and given as 3-dose series with 6 months between each dose. Moreover, in September 2018, World Health Organization (WHO) updated its recommendations regarding the use of CYD-TDV based on the evidence that seronegative vaccine recipients have an excess risk of hospitalized and severe dengue compared to seronegative non-vaccinated individuals.[20] Therefore, there is an urgent need to develop safe and effective therapeutics for the treatment of dengue virus infection.

Dengue viruses (DENV) belong to the genus Flavivirus within the Flaviviridae family, and there are 4 distinct, but closely related, serotypes of the virus (DENV-1, DENV-2, DENV-3, and DENV-4).[21, 22] A geographic region may be affected by one or more DENV serotypes simultaneously.[23-25] Recovery from infection by one serotype provides lifelong immunity against that particular serotype, while cross-immunity against the other serotypes is only partial and temporary.[26, 27] A second infection with a different dengue serotype is more likely to develop severe dengue.[28-32] Hence an ideal dengue antiviral should be effective against all four serotypes.[33] The dengue viral genome is a positive single-strand RNA of approximately 11 kb in length. This RNA encodes three structural proteins (capsid, envelope, and membrane) that form the virus particle and seven non-structural proteins (NS1, NS2A, NS2B, NS3, NS4A, NS4B, and NS5) that are essential for replication of the virus.[34] Dengue NS4B is a small integral membrane, consisting of 248 amino acid residues. It is moderately conserved, with about 83-89% amino acid similarity among the four dengue serotypes. Due to its high hydrophobicity, neither the crystal nor NMR structure of flavivirus NS4B is currently available.[35, 36] In the recent years, some progresses have been made to figure out the biological functions of NS4B, including its engagement in host innate immunity and interactions with other viral proteins.[37-45] However, the exact mechanisms of flavivirus NS4B involved in the viral replication cycle remain elusive. A series of spiropyrazolopyridone analogues as potent inhibitors against DENV-2 and DENV-3 was discovered, while these compounds have a lack of potency against DENV-1 and DENV-4.[51-53]

One aspect of the invention pertains to a compound of Formula (I)

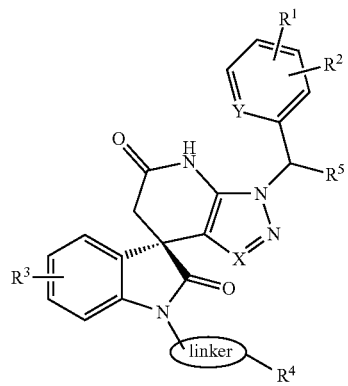

Formula I wherein:
$R^1$, $R^2$ are independently chosen from H, F, Cl, Br and $CF_3$;
$R^3$ is F, Cl and Br;
$R^4$ is F, Cl, Br, alkyl, alkenyl, alkynyl, alkoxy, hydroxyl, carboxyl, ester, acetal, amino, 5-membered cycle or heterocycle, 6-membered cycle or heterocycle;
$R^5$ is H, alkyl;
X, Y are independently chosen from CH and N;
Linker is a 1-20 atom length carbon chain or other chains, which include ester bonds, amide bonds or oxygen atoms (e.g. alkoxy).

A compound according to formula Ia, wherein:

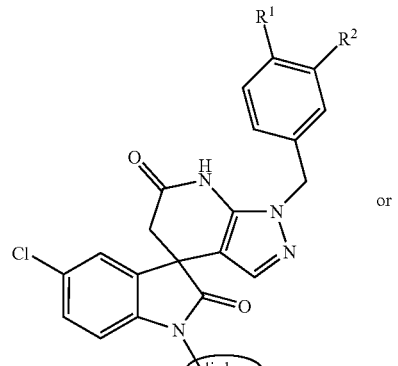

Formula Ia

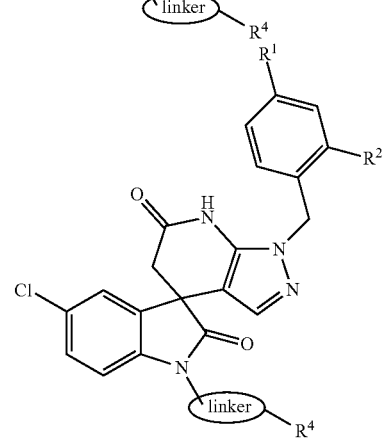

A further aspect of the invention pertains to a compound according to formula Ib, wherein:

Formula Ib

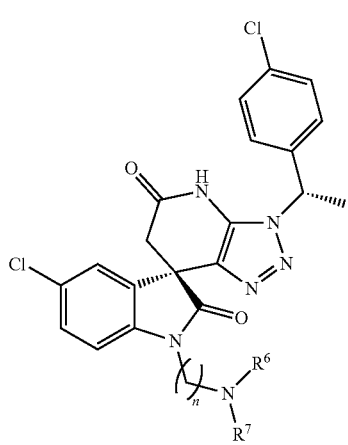

wherein R[6], R[7] are independently chosen from H, alkyl; or R[7], R[8] taken together with other atoms to form 5-membered or 6-membered heterocycle rings n is 1-10.

A further aspect of the invention pertains to compound according to formula Ic, wherein:

Formula Ic wherein R[8], R[9] is independently chosen from H, alkyl, alkoxy, F, Cl, Br and CF$_3$, hydroxyl, carboxyl, ester, cyano, amino, nitro, or R[9], R[10] taken together with other atoms to form 5-membered or 6-membered fused ring.

X$_1$, X$_2$, X$_3$ are independently chosen from CH and N.

n is 1-10.

A further aspect of the invention pertains compound according to formula Id, wherein:

wherein R[10] is chosen from
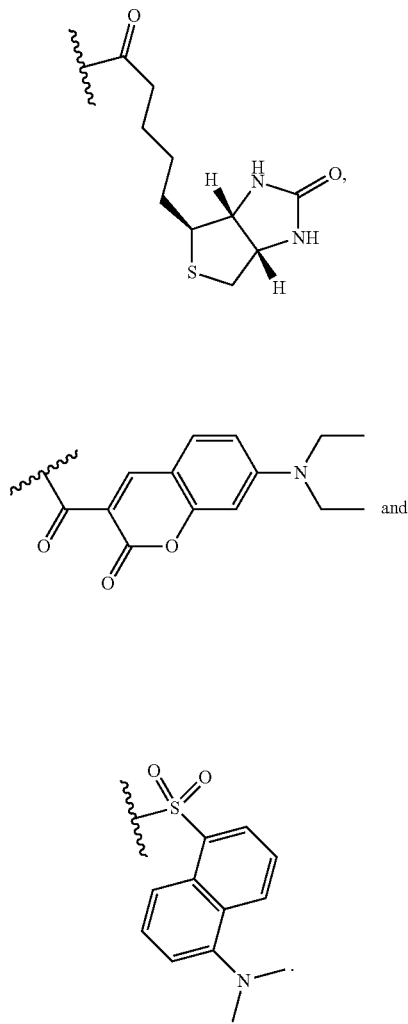
n is 1-10.
In some embodiments, the compound according to formula Ie may be any of:
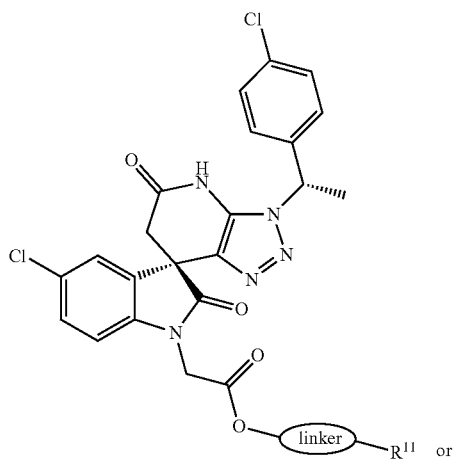
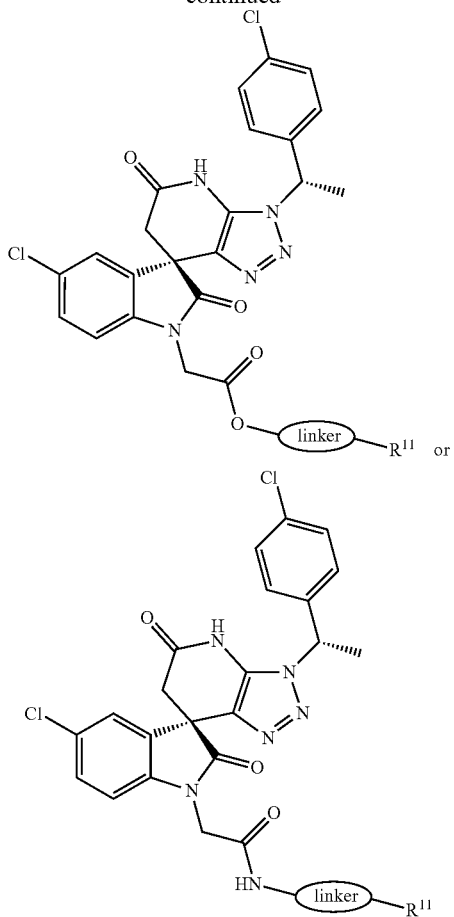
wherein R[11] is chosen from
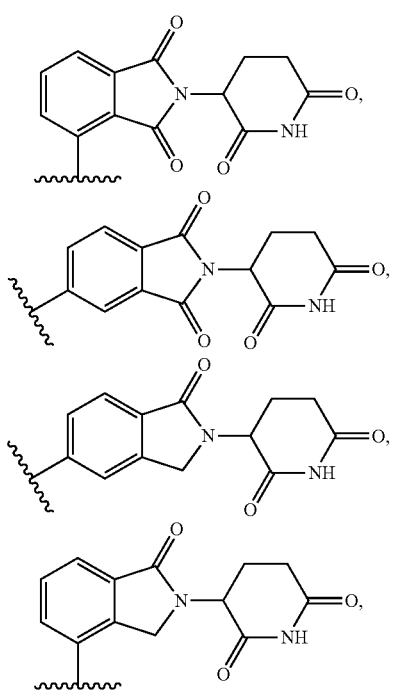

-continued

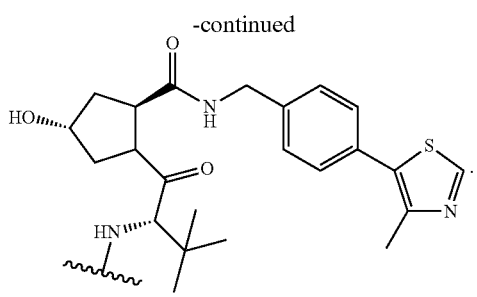

Linker is a 1-20 atom length carbon chain or other chains, which include ester bond, amide bond or oxygen atom.

A further aspect of the invention pertains to a compound of Formula (II)

Formula II

Wherein $X_4$, $X_5$ are independently chosen from F, Cl, Br and $CF_3$, $R^{12}$, $R^{13}$ are 1-20 atom length carbon chains, which is optionally substituted one or more ester bonds, amide bonds or oxygen atoms; wherein said chain is tethered to a terminal group chosen from F, Cl, Br, alkyl, alkenyl, alkynyl, alkoxy, hydroxyl, carboxyl, ester, acetal, amino, 5-membered cycle or heterocycle, 6-membered cycle and heterocycle.

In some embodiments, the invention encompasses a compound of Formula I or a pharmaceutically acceptable salt thereof, wherein said linker is a 7-20 atom length carbon chain, which is optionally substituted one or more ester bonds, amide bonds or oxygen atoms; and wherein $R^4$ is F, Cl, Br, alkyl, alkenyl, alkynyl, alkoxy, hydroxyl, carboxyl, ester, acetal, amino, 5-membered cycle or heterocycle, 6-membered cycle or heterocycle.

In some embodiments, the invention encompasses a compound Of Formula I, or a pharmaceutically acceptable salt thereof according to claim 1, wherein said linker is a 13-20 atom length carbon chain, which is optionally substituted one or more ester bonds, amide bonds or oxygen atoms; and wherein $R^4$ is F, Cl, Br, alkyl, alkenyl, alkynyl, alkoxy, hydroxyl, carboxyl, ester, acetal, amino, 5-membered cycle or heterocycle, 6-membered cycle or heterocycle.

Another aspect of the invention pertains to a method of treating dengue disease comprising administering an Dengue NS4B specific inhibitor to a subject having dengue disease, wherein the Dengue NS4B specific inhibitor is a compound of chosen from Formulas I, Ia, Ib, Ic, Id, and II, or a combination thereof.

In some embodiments, the dengue disease is severe dengue disease, dengue hemorrhagic fever, or dengue shock syndrome.

In some embodiments, the dengue disease is caused by a dengue virus of serotype 1, 2, or 3.

EXAMPLES

Synthesis of Compounds of the Invention

The description of preparation of certain embodiments of the invention is meant to be exemplary of certain embodiments of the invention. The reagents and reactants used for synthetic conversions outlined herein and below is merely exemplary. The invention contemplates using the same or different reagents discussed herein to achieve preparation of the cations of the invention.

The three component condensation of substituted aminotriazoles, isatin derivatives, and Meldrum's acid can provide the access to a series of spirotrizolopyridone analogues for investigating the substitution on the two amide groups.[51, 52] However, this condensation yields the final product as two enantiomers or diastereoisomers with great discrepancy in potency, and it will bring a large amount of separation work to get each pure and potent stereoisomer. Surprisingly, when 1.2 equivalent of methyl iodide was added, direct methylation of pure diastereoisomer 1a afforded mono-methylated product 7 with a high yield of 76% (Scheme 1). The structure of methylated derivative 7 was subsequently determined by X-ray crystallography to confirm the methylation position and the absolute configurations of the chiral centers. These results demonstrated that the amide of the indolone moiety has a higher nucleophilic reactivity in comparison with the one of the pyridone moiety, and it provides a good chance for a quick SAR investigation on this part using pure stereoisomer 1a as a starting material. The synthesis of diastereoisomer 1a commenced with commercially available 1-(4-chlorophenyl)ethanol (2), which was brominated followed by azidation to generate azide 3.[52] This intermediate was treated with ethyl 2-cyanoacetate and sodium in ethanol to provide aminocarboxylate 4, which was then converted to (S)-aminotriazole 6 via hydrolysis, decarboxylation, and then chiral HPLC separation. Aminotriazole 6 was condensed with 5-chloroisatin and Meldrum's acid in acetic acid to give the final products as two diastereoisomers with a ratio of approximately 1:1, which were successfully separated by column chromatography to afford pure stereoisomer 1a and 1b.

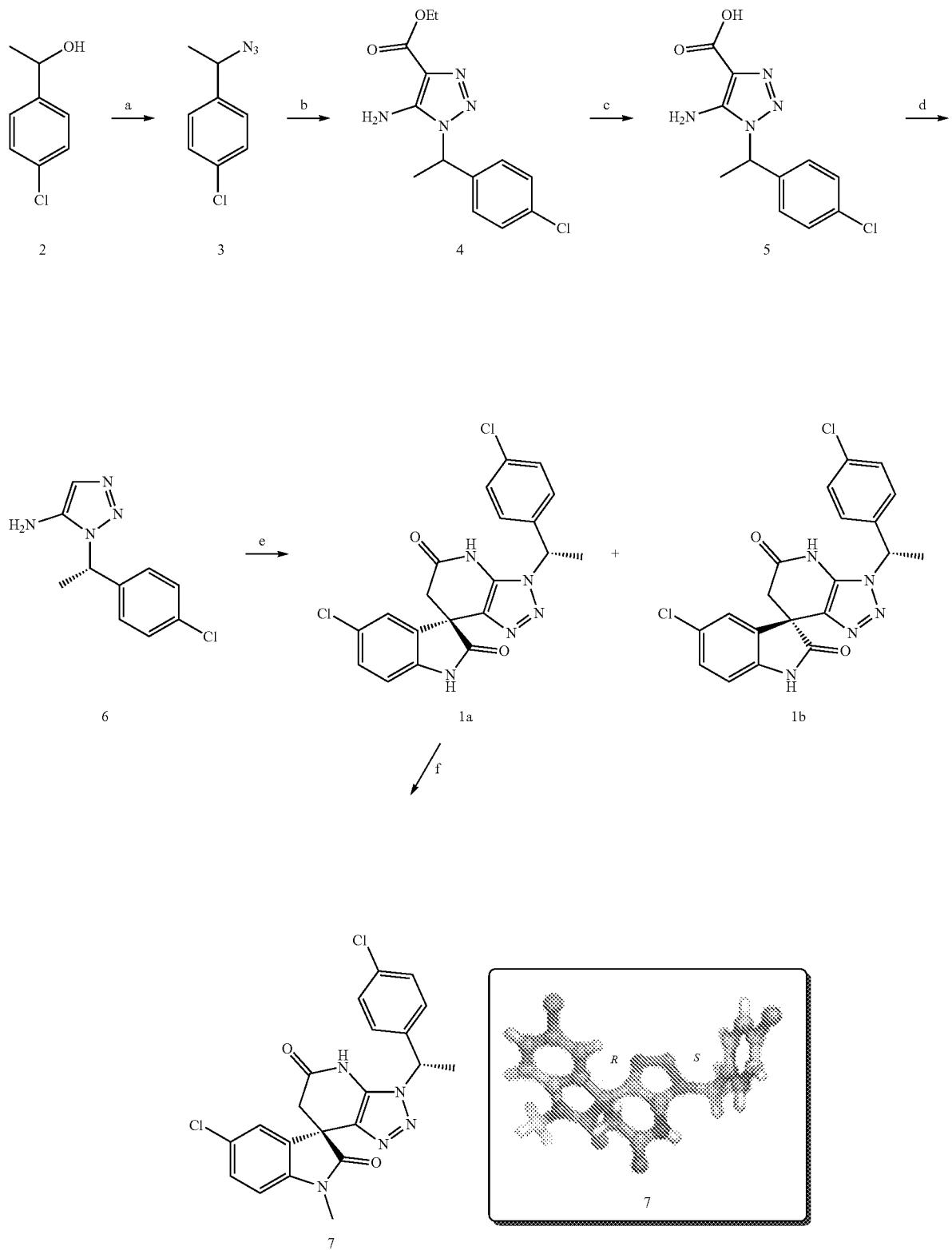
Scheme 1. Synthesis of Compounds 1a and 7[a]
[a]Reagents and conditions: (a) i. PBr₃, CH₂Cl₂, 0° C. to r.t, 4 h; ii. NaN₃, DMSO, r.t, 5 h. (b) ethyl 2-cyanoacetate, Na, EtOH, 85° C., 5 h. (c) NaOH, EtOH/H₂O, 85° C., 4 h. (d) i. DMF, 200° C., 20 min; ii. chiral HPLC separation. (e) 5-chloroisatin, Meldrum's acid, AcOH, 100° C., 4 h. (f) CH₃I, NaH, DMF, 0° C. to r.t, 2 h.

Scheme 2. Synthesis of Substituted 4,6-Dihydrospiro[[1,2,3]triazolo[4,5-b]pyridine-7,3′-indoline]-2′,5(3H)-dione Analogues 8-50 and 50-70[a]
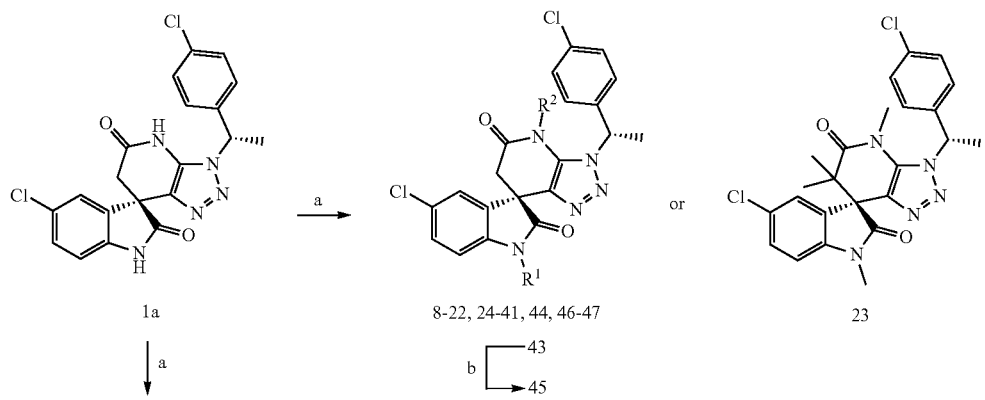
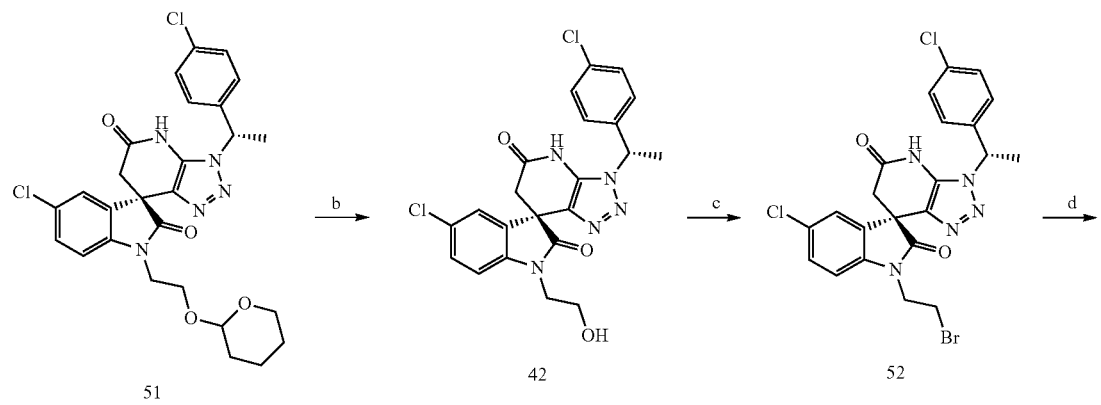
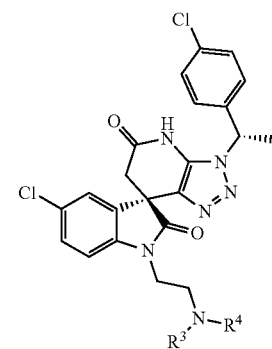
55-62

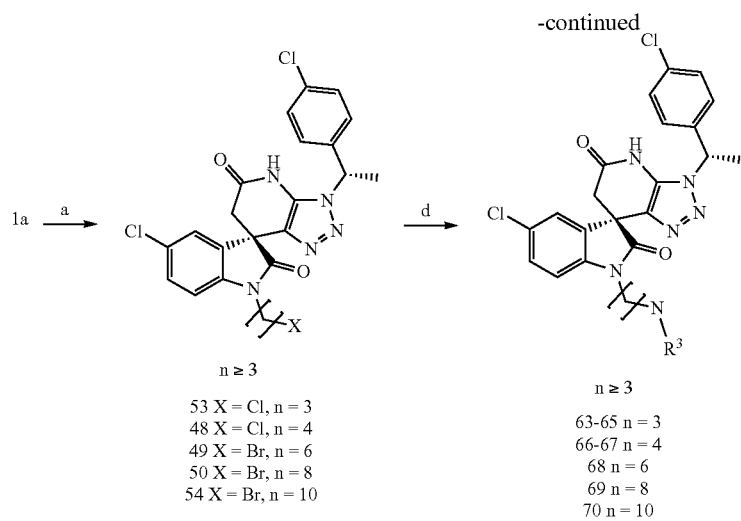

53 X = Cl, n = 3
48 X = Cl, n = 4
49 X = Br, n = 6
50 X = Br, n = 8
54 X = Br, n = 10

63-65 n = 3
66-67 n = 4
68 n = 6
69 n = 8
70 n = 10

[a]Reagents and conditions: (a) RI or RBr, NaH, DMF, 0° C. to r.t. or 50° C. (b) TsOH, MeOH, r.t., (c) PPh$_3$, CBr$_4$, DCM, 0° C. to r.t. (d) R$^3$R$^4$NH, K$_2$CO$_3$, CH$_3$CN, 60° C.~80° C.

With pure stereoisomer 1a in hand, the effect of the substitution on the two amide moieties was successfully explored. As outlined in Scheme 2, direct substitution of 1a with corresponding iodide or bromide afforded a series of substituted 4,6-dihydrospiro[[1,2,3]triazolo[4,5-b]pyridine-7,3'-indoline]-2',5(3H)-dione analogues 8-41, 43-44, 46-51 and 53-54. Acid analogue 45 was accessed from ester 43 via hydrolysis. Depyranylation of THP ether 51 gave alcohol 42, which was then brominated to give bromide 52. Substitution of bromide or chloride 48-50 and 52-54 with different amines afforded the corresponding amine analogues 55-70. To assist the target validation and mechanistic studies of this series of molecules, two biotinylated compounds 73 and 75 were designed and synthesized as the chemical probe tools (Scheme 3). Condensation of D-(+)-Biotin (71) with methyl 8-aminooctanoate was followed by hydrolysis to provide acid 72, which was then condensed with alcohol 42 to give the biotinylated analogue 73. The biotinylated analogue 75 was prepared using the same route as that for its diastereoisomer 73 starting from compound 1b for comparison.

Scheme 3. Synthesis of Biotinylated Analogues 73 and 75[a]

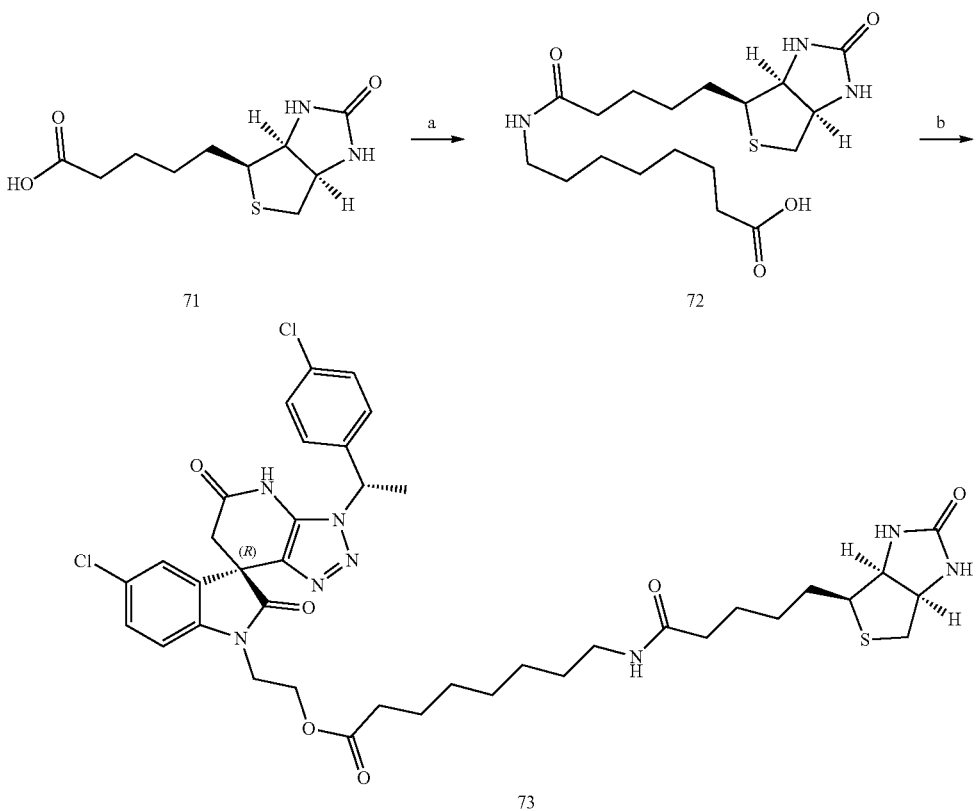

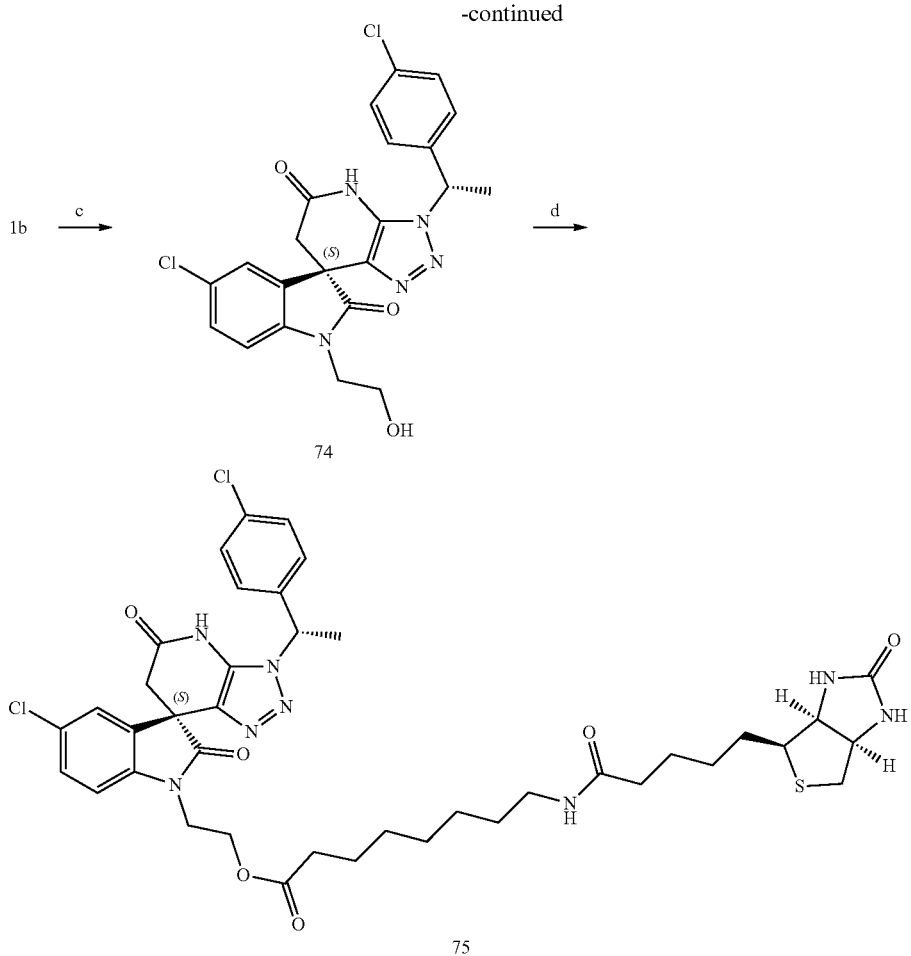

*Reagents and conditions: (a) i. methyl 8-aminooctanoate hydrochloride, EDCI, HOBt, DIEA, DMF, r.t; ii. NaOH, MeOH/H$_2$O, r.t. (b) 42, EDCI, DMAP, DMF, r.t. (c) i. 2-(2-bromoethoxy)tetrahydro-2H-pyran, NaH, DMF, 0° C. to r.t.; ii. TsOH, MeOH, r.t. (d) 72, EDCI, DMAP, DMF, r.t.

In Vitro Evaluation of DENV Inhibition. Compound 7 with methyl on the amide of indolone showed increased inhibitory activities against DENV-2 and DENV-3 (EC$_{50}$=0.019 μM and 0.004 μM, respectively) compared to the parent compound 1a. However, neither of these two compounds showed potency against DENV-1 or DENV-4 (EC$_{50}$>5 μM). Compound 8 with ethyl began to show inhibitory activity against DENV-1 with an EC$_{50}$ of 2.5 μM, while it maintained the same level of potency against DENV-2 and DENV-3 (EC$_{50}$=0.024 μM and 0.006 μM, respectively). When the length of alkyl is increased, the corresponding compounds (9, 10 and 11) showed improved potency against DENV-1 with EC$_{50}$ values of 1.9 μM, 1.3 μM and 0.83 μM, respectively. Nevertheless, n-hexyl group (11) resulted in a significant loss of potency against DENV-2 and DENV-3 (EC$_{50}$=0.81 μM and 0.14 μM, respectively); n-decyl group (12) led to a complete loss of potency against DENV-2 (EC$_{50}$>10 μM), while it showed potency against DENV-1, -3 and -4 with EC$_{50}$ values of 3.4 μM, 1.2 μM and 7.3 μM, respectively. These results indicated that the long length of alkyl was unfavorable for DENV-2 potency. Compounds with the branched alkyl groups (13-15) showed potency against DENV-1 to -3 with the same trend. Among these compounds, 15 with isopentyl showed the most potent inhibitory activity against DENV-1 with an EC$_{50}$ of 0.78 μM, meanwhile maintaining a similar level of potency against DENV-2 and DENV-3 (EC$_{50}$=0.16 μM and 0.035 μM, respectively). Unfortunately, all these compounds showed no obvious potency against DENV-4 (EC$_{50}$>5 μM). Interestingly, compound 16 with 3,3-dimethylbutyl maintained potency against DENV-1 to -3 (EC$_{50}$=1.1 μM, 0.87 μM and 0.082 μM, respectively), while also showing inhibitory activity against DENV-4 with EC$_{50}$ of 3.9 μM.

Compounds 17 with cyclopropylmethyl and 18-20 with unsaturated alkyls all exhibited good potency against DENV-2 and DENV-3 and weak inhibitory activities against DENV-1 and DENV-4. Compound 21 with isopropyl on the amide of pyridone also showed broad inhibitory activities against DENV-1 to -4 with EC$_{50}$ of 2.1 μM, 0.86 μM, 0.31 μM and 4.4 μM, respectively. However, considering the significant loss of potency against DENV-2 when introducing the alkyl group on the amide of pyridone (21), the subsequent investigation was mainly focused on the indolone moiety. Two isopropyl substitutions (22) further decreased the antiviral activity against DENV-2 (EC$_{50}$>10 μM) and DENV-3 (EC$_{50}$=1.5 μM), while it maintained potency against DENV-1 and DENV-4 (EC$_{50}$=3.8 μM and 3.0 μM, respectively). Compound 23 with four methyl groups (α-carbonyl carbon was di-methylated) resulted in significant loss of potency against all four DENV serotypes (EC$_{50}$>5 μM).

TABLE 1
Antiviral Activity and Cytotoxicity of Compounds 1a and 7-23
| Compd | R¹ | R² | EC$_{50}$ (µM)$^a$ | | | | CC$_{50}$ (µM)$^b$ |
| --- | --- | --- | --- | --- | --- | --- | --- |
| | | | DENV-1 | DENV-2 | DENV-3 | DENV-4 | |
| 1a | H | H | >5.0 | 0.039 | 0.010 | >5.0 | >10 |
| 7 |  | H | >5.0 | 0.019 | 0.004 | >5.0 | >10 |
| 8 | 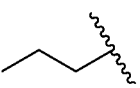 | H | 2.5 | 0.024 | 0.006 | >5.0 | >10 |
| 9 | 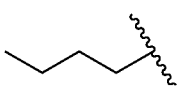 [SMILES: *CCCC] | H | 1.9 | 0.071 | 0.010 | >5.0 | >10 |
| 10 | 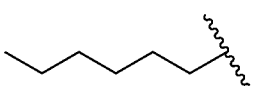 [SMILES: *CCCCCC] | H | 1.3 | 0.075 | 0.018 | >5.0 | >10 |
| 11 | 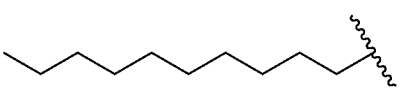 [SMILES: *CCCCCCCCCC] | H | 0.83 | 0.81 | 0.14 | >5.0 | >10 |
| 12 |  | H | 3.4 | >10 | 1.2 | 7.3 | >10 |
| 13 | 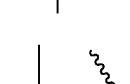 | H | 5.7 | 0.023 | 0.009 | >5.0 | >10 |
| 14 |  | H | 1.3 | 0.15 | 0.020 | >5.0 | >10 |
| 15 | 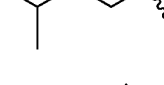 | H | 0.78 | 0.16 | 0.035 | >5.0 | >10 |
| 16 | | H | 1.1 | 0.87 | 0.082 | 3.9 | >10 |

TABLE 1-continued

Antiviral Activity and Cytotoxicity of Compounds 1a and 7-23

| Compd | R¹ | R² | EC$_{50}$ (μM)[a] | | | | CC$_{50}$ (μM)[b] |
|---|---|---|---|---|---|---|---|
| | | | DENV-1 | DENV-2 | DENV-3 | DENV-4 | |
| 17 | cyclopropylmethyl | H | 3.1 | 0.11 | 0.017 | >5.0 | >10 |
| 18 | allyl | H | 2.1 | 0.038 | 0.005 | >5.0 | >10 |
| 19 | propargyl | H | >5.0 | 0.069 | 0.003 | >5.0 | >10 |
| 20 | 2-butynyl | H | >5.0 | 0.063 | 0.020 | >5.0 | >10 |
| 21 | H | isobutyl | 2.1 | 0.86 | 0.31 | 4.4 | >10 |
| 22 | isobutyl | isobutyl | 3.8 | >10 | 1.5 | 3.0 | >10 |
| 23 | (4-chlorobenzyl, gem-dimethyl, N-Me) | | >5.0 | >5.0 | >5.0 | >5.0 | >10 |

[a]EC$_{50}$ values were determined on Huh7 cells stably expressing DENV-1 to -4 replicon.
[b]CC$_{50}$ values were measured using Huh7 cells stably expressing DENV-2 replicon.

Compounds 24-37 were prepared and evaluated as shown in Table 2. Compounds 24 with benzyl and 25-26 with fluorobenzyl showed moderate potency against DENV-2 (EC$_{50}$=0.14~0.29 μM) and DENV-3 (EC$_{50}$=0.020~0.051 μM), weak potency against DENY-1 (EC$_{50}$=2.0 μM, 5.0 μM and 10.0 μM, respectively), and no obvious potency against DENV-4. Compounds 27 with 4-chlorobenzyl and 28 with 4-chloro-3-fluorobenzyl resulted in a significant loss of potency against DENV-2 ($EC_{50}$=3.3 µM and 4.0 µM, respectively) and DENV-3 ($EC_{50}$=0.20 µM and 0.29 µM, respectively). However, these two compounds showed potency against both DENV-1 ($EC_{50}$=2.2 µM and 1.5 µM, respectively) and DENV-4 ($EC_{50}$=6.5 µM and 5.1 µM, respectively). 3-Methoxybenzyl substitution (29) showed moderate potency against DENV-2 and DENV-3 ($EC_{50}$=0.83 µM and 0.087 µM, respectively) and weak potency against DENY-1 and DENV-4 ($EC_{50}$=2.6 µM and 6.2 µM, respectively). 3,5-Dimethoxybenzyl substitution (30) displayed decreased potency against DENV-2 and DENV-3 ($EC_{50}$=3.1 µM and 0.79 µM, respectively) and maintained the same level of potency against DENY-1 and DENV-4 ($EC_{50}$=3.4 µM and 7.4 µM, respectively). Interestingly, 3,5-di-tert-butylbenzyl substitution (31) showed no obvious potency against DENV-2 ($EC_{50}$>10 µM), while it maintained potency against DENY-1 and DENV-4 ($EC_{50}$=4.6 µM and 4.9 µM, respectively). Compound 32 with homobenzyl exhibited improved potency against DENY-1 ($EC_{50}$=1.111M) and decreased potency against DENV-2 and DENV-3 ($EC_{50}$=0.60 µM and 0.19 µM, respectively) in comparison with 24. Excitingly, compounds 33-37 with pyridine moieties displayed highly potent inhibitory activities against DENV-2 ($EC_{50}$=0.020~0.15 µM) and DENV-3 ($EC_{50}$=0.003~0.025 µM). However, no significant improvement of potency against DENV-4 was observed for these compounds.

TABLE 2

Antiviral Activity and Cytotoxicity of Compounds 24-37

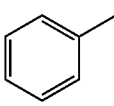

| Compd | R$_1$ | R$_2$ | DENV-1 | DENV-2 | DENV-3 | DENV-4 | CC$_{50}$ (µM)[b] |
|---|---|---|---|---|---|---|---|
| 24 | 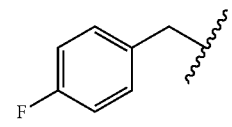 [SMILES: *Cc1ccc(F)cc1] | H | 2.0 | 0.15 | 0.020 | >5.0 | >10 |
| 25 | 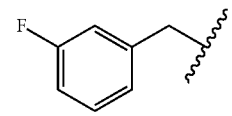 [SMILES: *Cc1cccc(F)c1] | H | 5.0 | 0.16 | 0.048 | 10 | >10 |
| 26 | 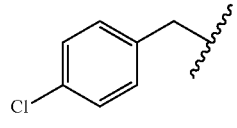 [SMILES: *Cc1ccc(Cl)cc1] | H | 10.0 | 0.29 | 0.051 | >5.0 | >10 |
| 27 | 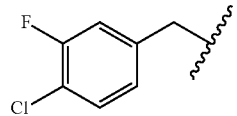 [SMILES: *Cc1ccc(Cl)c(F)c1] | H | 2.2 | 3.3 | 0.20 | 6.5 | >10 |
| 28 | 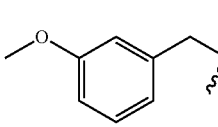 | H | 1.5 | 4.0 | 0.29 | 5.1 | >10 |
| 29 |  | H | 2.6 | 0.83 | 0.087 | 6.2 | >10 |

EC$_{50}$ (µM)[a]

TABLE 2-continued

Antiviral Activity and Cytotoxicity of Compounds 24-37

| Compd | R₁ | R₂ | EC$_{50}$ (μM)[a] | | | | CC$_{50}$ (μM)[b] |
| --- | --- | --- | --- | --- | --- | --- | --- |
| | | | DENV-1 | DENV-2 | DENV-3 | DENV-4 | |
| 30 | 3,5-dimethoxybenzyl | H | 3.4 | 3.1 | 0.79 | 7.4 | >10 |
| 31 | 3,5-di-tert-butylbenzyl | H | 4.6 | >10 | 5.9 | 4.9 | >10 |
| 32 | phenethyl | H | 1.1 | 0.60 | 0.19 | >5.0 | >10 |
| 33 | 2-pyridylmethyl | H | >5.0 | 0.020 | 0.003 | >5.0 | >10 |
| 34 | 3-pyridylmethyl | H | 3.2 | 0.029 | 0.021 | >5.0 | >10 |
| 35 | 4-pyridylmethyl | H | >5.0 | 0.072 | 0.025 | >5.0 | >10 |
| 36 | (6-chloropyridin-3-yl)methyl | H | >5.0 | 0.078 | 0.006 | >5.0 | >10 |

TABLE 2-continued

Antiviral Activity and Cytotoxicity of Compounds 24-37

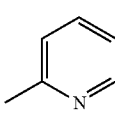

| Compd | R₁ | R₂ | EC$_{50}$ (µM)$^a$ DENV-1 | DENV-2 | DENV-3 | DENV-4 | CC$_{50}$ (µM)$^b$ |
|---|---|---|---|---|---|---|---|
| 37 | (6-methylpyridin-3-yl)methyl | H | >5.0 | 0.15 | 0.011 | >5.0 | >10 |

$^a$EC$_{50}$ values were determined on Huh7 cells stably expressing DENV-1 to -4 replicon.
$^b$CC$_{50}$ values were measured using Huh7 cells stably expressing DENV-2 replicon.

Next, a wide range of functional groups was investigated. As listed in Table 3, ether (38 and 39), acetal (41), alcohol (42), ester (43), 2-fluoroethyl (46) and 4-chlorobutyl (48) groups were all well tolerated on the amide of indolone moiety, presenting potent inhibitory activities against DENV-2 (EC$_{50}$=0.037~0.29 µM) and DENV-3 (EC$_{50}$=0.009~0.076 µM). Ether (40) and ester (44) on the amide of pyridone moiety resulted in a significant loss of potency against DENV-2 (EC$_{50}$=8.7 µM and >10 µM, respectively), compared to the corresponding substitutions on the amide of indolone moiety (39 and 43). Neither of these two compounds showed potency against DENY-1 and DENV-4 (EC$_{50>}$10 µM). The carboxyl group (45) diminished the potency against DENV-2 (EC$_{50}$=2.4 µM) in comparison of the corresponding ester (43). Surprisingly, compound 47 with 3-bromopropyl showed potency against all four serotypes DENY-1 to -4 (EC$_{50}$=2.4 µM, 0.25 µM, 0.076 µM and 3.2 µM, respectively). Substitutions with long carbon chain (49-50) showed decreased potency against DENV-2, consistent with the trend observed before.

TABLE 3

Antiviral Activity and Cytotoxicity of Compounds 38-50

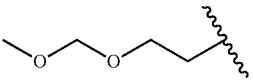 [SMILES: *CCOCOC]

| Compd | R₁ | R₂ | EC$_{50}$ (µM)$^a$ DENV-1 | DENV-2 | DENV-3 | DENV-4 | CC$_{50}$ (µM)$^b$ |
|---|---|---|---|---|---|---|---|
| 38 | methoxymethoxypropyl | H | >5.0 | 0.092 | 0.019 | >5.0 | >10 |

TABLE 3-continued

Antiviral Activity and Cytotoxicity of Compounds 38-50

| Compd | R₁ | R₂ | EC$_{50}$ (μM)$^a$ | | | | CC$_{50}$ (μM)$^b$ |
|---|---|---|---|---|---|---|---|
| | | | DENV-1 | DENV-2 | DENV-3 | DENV-4 | |
| 39 | MeO(CH₂)₃– | H | >5.0 | 0.040 | 0.009 | >5.0 | >10 |
| 40 | H | MeO(CH₂)₃– | >10 | 8.7 | 0.91 | >10 | >10 |
| 41 | (MeO)₂CHCH₂– | H | >5.0 | 0.29 | 0.076 | >5.0 | >10 |
| 42 | HO(CH₂)₂– | H | >5.0 | 0.037 | 0.010 | >5.0 | >10 |
| 43 | MeO₂CCH₂– | H | >5.0 | 0.077 | 0.011 | >5.0 | >10 |
| 44 | H | MeO₂CCH₂– | >10 | >10 | 2.7 | >10 | >10 |
| 45 | HO₂CCH₂– | H | ND$^c$ | 2.4 | ND | ND | >10 |

TABLE 3-continued

Antiviral Activity and Cytotoxicity of Compounds 38-50

[Structure shown with $R_1$, $R_2$ substituents on spiro-indolone/triazole/pyridone scaffold with chlorophenyl and chloroindolone groups]

| Compd | $R_1$ | $R_2$ | $EC_{50}$ (μM)[a] DENV-1 | DENV-2 | DENV-3 | DENV-4 | $CC_{50}$ (μM)[b] |
|---|---|---|---|---|---|---|---|
| 46 | F-CH2CH2- | H | >5.0 | 0.038 | 0.009 | >5.0 | >10 |
| 47 | Br-(CH2)3- | H | 2.4 | 0.25 | 0.076 | 3.2 | >10 |
| 48 | Cl-(CH2)4- | H | >5.0 | 0.073 | 0.019 | >5.0 | >10 |
| 49 | Br-(CH2)7- | H | ND | 3.0 | ND | ND | >10 |
| 50 | Br-(CH2)9- | H | ND | >5.0 | ND | ND | >10 |

[a]$EC_{50}$ values were determined on Huh7 cells stably expressing DENV-1 to -4 replicon.
[b]$CC_{50}$ values were measured using Huh7 cells stably expressing DENV-2 replicon.
[c]ND: not detected.

To improve the aqueous solubility, compounds 55-70 were synthesized and evaluated (Table 4). Intriguingly, amino analogs 55-62 with two carbon chain and 63-65 with three carbon chain all showed great potency against DENV-2 ($EC_{50}$=0.025~0.13 μM) and DENV-3 ($EC_{50}$=0.001~0.030 μM). When the length of carbon chain was increased from 4 to 10, the potency of the compounds (66-70) against DENV-2 exhibited a declining trend. Among these compounds, 68 with 6-(dimethylamino)hexyl group was effective against three serotypes DENY-1 to -3 ($EC_{50}$=1.5 μM, 0.90 μM and 0.066 μM, respectively); 70 with 10-(dimethylamino)decyl group showed moderate to high potency against all four serotypes DENY-1 to -4 ($EC_{50}$=2.7 μM, 3.5 μM, 0.098 μM and 3.5 μM, respectively). However, all these amino compounds except 70 lack potency against DENV-4. Taken together, the substitution on the amide of indolone moiety was widely tolerated against DENV-2 and DENV-3, and various functional groups such as amino, hydroxyl, and ester with proper carbon chain maintained the same level of potency against these two serotypes. The alkyl groups with proper length are favorable for DENY-1 potency, while the long and bulky alkyl groups are beneficial for DENV-4 potency. The substitutions on the amide of pyridone moiety or on both amide moieties diminished the potency against DENV-2 and DENV-3. However, compounds with the proper substitutions at these positions maintained the micromolar level of potency against both DENY-1 and DENV-4. Unfortunately, during this SAR investigation, no highly potent compounds were discovered against all four serotypes DENY-1 to -4 except a few compounds such as 16, 21, 27-29, 47 and 70 with a relatively moderate potency.

TABLE 4
Antiviral Activity and Cytotoxicity of Compounds 55-70
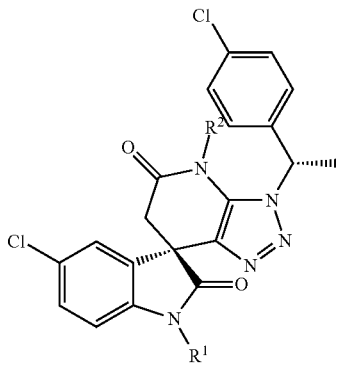
| Compd | R₁ | R₂ | EC$_{50}$ (μM)$^a$ DENV-1 | DENV-2 | DENV-3 | DENV-4 | CC$_{50}$ (μM)$^b$ |
|---|---|---|---|---|---|---|---|
| 55 | 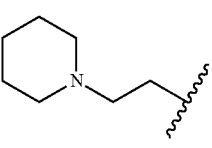 [SMILES: *CCN1CCCCC1] | H | >5.0 | 0.075 | 0.017 | >5.0 | >10 |
| 56 | 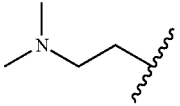 [SMILES: *CCN(C)C] | H | >5.0 | 0.074 | 0.005 | >5.0 | >10 |
| 57 | 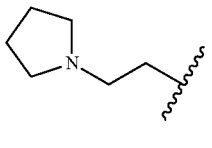 [SMILES: *CCN1CCCC1] | H | >5.0 | 0.025 | 0.002 | >5.0 | >10 |
| 58 | 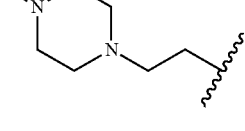 | H | >5.0 | 0.038 | 0.006 | >5.0 | >10 |
| 59 | 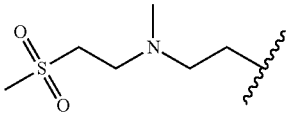 [SMILES: *CCN(C)CCS(C)(=O)=O] | H | >5.0 | 0.30 | 0.030 | >5.0 | >10 |
| 60 | 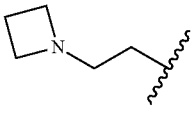 | H | >5.0 | 0.077 | 0.018 | >5.0 | >10 |
| 61 | 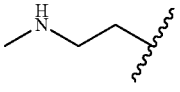 [SMILES: *CCNC] | H | >5.0 | 0.067 | 0.007 | >5.0 | >10 |
| 62 | 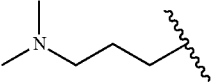 [SMILES: *CCCN(C)C] | H | >5.0 | 0.12 | 0.022 | >5.0 | >10 |
| 63 |  | H | >5.0 | 0.025 | 0.001 | >5.0 | >10 |

TABLE 4-continued

Antiviral Activity and Cytotoxicity of Compounds 55-70

| Compd | R₁ | R₂ | EC$_{50}$ (μM)$^a$ DENV-1 | DENV-2 | DENV-3 | DENV-4 | CC$_{50}$ (μM)$^b$ |
|---|---|---|---|---|---|---|---|
| 64 | piperidinyl-propyl | H | >5.0 | 0.13 | 0.012 | >5.0 | >10 |
| 65 | morpholinyl-propyl | H | >5.0 | 0.076 | 0.005 | >5.0 | >10 |
| 66 | dimethylamino-butyl | H | >5.0 | 0.19 | 0.038 | >5.0 | >10 |
| 67 | piperidinyl-pentyl | H | >5.0 | 0.35 | 0.078 | >5.0 | >10 |
| 68 | dimethylamino-hexyl | H | 1.5 | 0.90 | 0.066 | >5.0 | >10 |
| 69 | dimethylamino-octyl | H | >5.0 | 0.49 | 0.042 | >5.0 | >10 |
| 70 | dimethylamino-decyl | H | 2.7 | 3.5 | 0.098 | 3.5 | >10 |

$^a$EC$_{50}$ values were determined on Huh7 cells stably expressing DENV-1 to -4 replicon.
$^b$CC$_{50}$ values were measured using Huh7 cells stably expressing DENV-2 replicon.

Figure 1C:
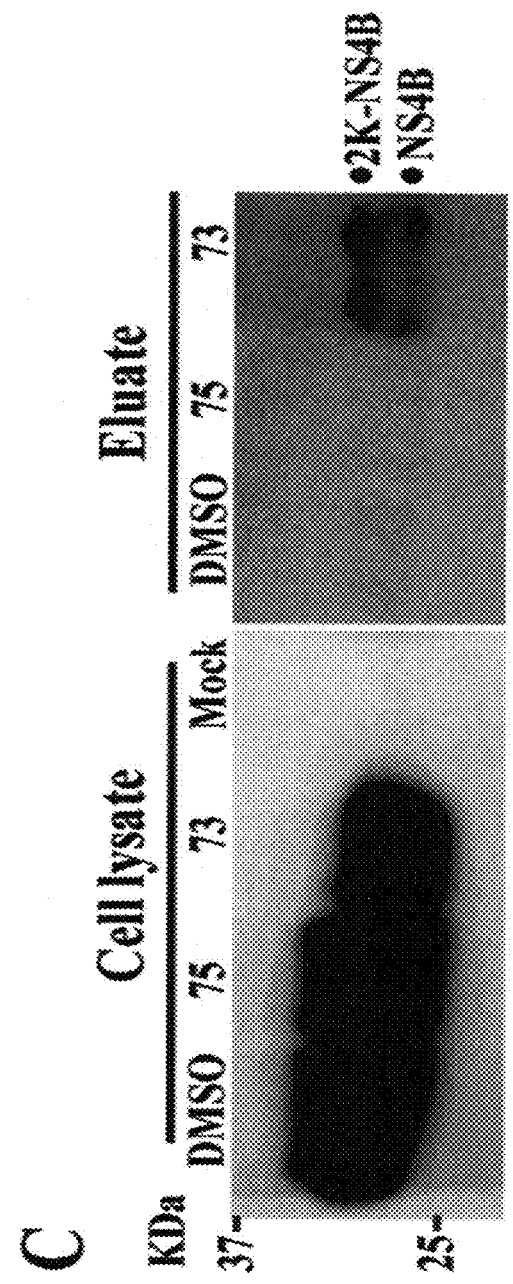

Biotinylated Compound 73 Can Pull Down NS4B Protein from Cell Lysates. The spiropyrazolopyridone derivatives can inhibit DENV replication by targeting NS4B protein.[53] To facilitate the validation of NS4B as the target of this class of compounds, a biotin group with a proper linker was added to compound 1a and its diastereoisomer 1b, resulting in compounds 73 and 75 (FIG. 1A). Consistent with previous SAR results, the (R,S)-diastereoisomer 73 but not the (S,S)-diastereoisomer 75 remains active against DENV-2 and DENV-3 with EC$_{50}$ values of 0.041 μM and 0.017 μM, respectively (FIG. 1B).[51, 52] In addition, compound 73 has no significant activity against DENV-1 and DENV-4 at the concentration up to 10 μM (data not shown). To further prove the association of compound 73 with viral NS4B protein, a pull-down assay was performed by mixing compounds with the lysates of DENV-2 infected cells. As shown in FIG. 1C, only compound 73 but not 75 can pull down viral NS4B protein, suggesting that this class of compounds likely target viral NS4B protein.

Figure 2A:
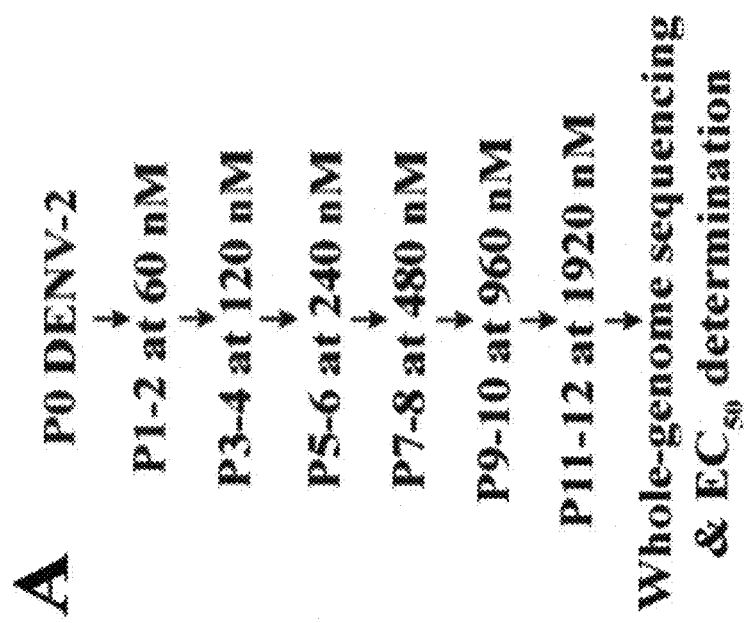
Figure 2C:
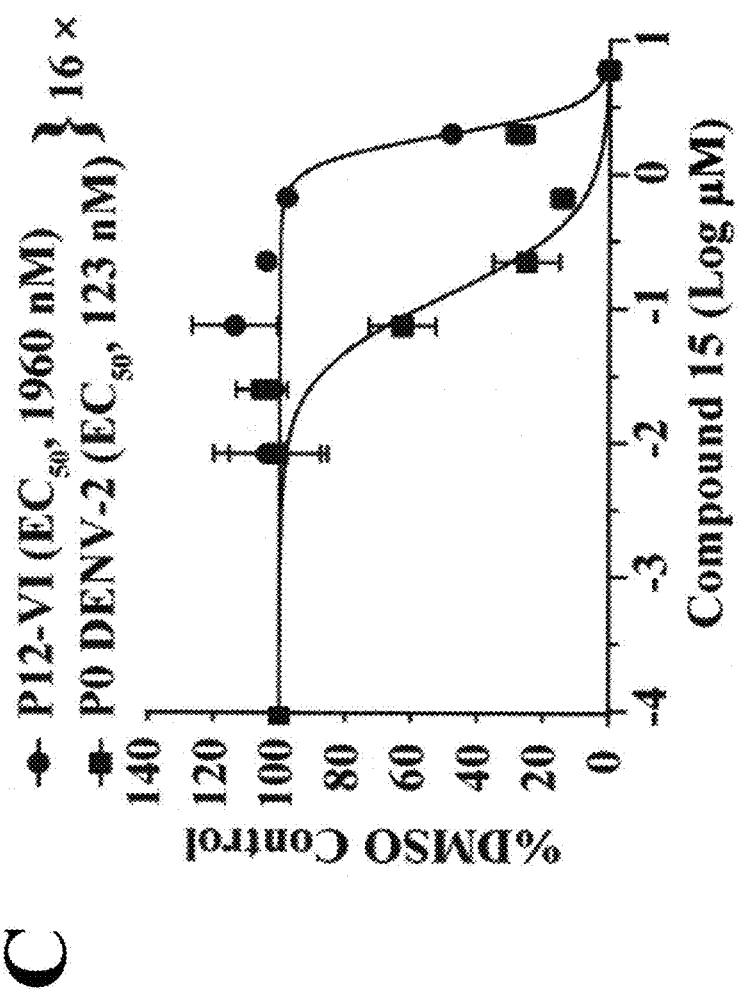

Compound 63 Resistance Maps to the Viral NS4B Protein. To further validate whether the series of compounds generated in this study still target DENV NS4B protein, resistant virus was prepared by consecutively culturing DENV-2 with increasing concentrations of compound 63 (FIG. 2A), a compound with excellent potency against DENV-2 and DENV-3. After twelve rounds of selection, all four independent selections in the presence of compound 63 (selections III to VI) showed increased $EC_{50}$ values by >100 folds (FIG. 2B). Sequencing of the entire genome of the resistant viruses revealed that the amino acid change at position 63 (V63M or V63L) in the NS4B protein occurred in those compound 63-treated isolates but not those DMSO-treated isolates (FIG. 2B). The same mutation has been previously determined responsible for the viral resistance to the spiropyrazolopyridone inhibitors.[53] The data demonstrated that DENV NS4B protein is still the target of this series of compounds. Moreover, we evaluated the sensitivity of the P12 viruses (using P12-VI as an example) to compound 15, a compound with excellent efficacy against three serotypes DENV-1 to -3 (FIG. 2C). The mutation NS4B V63L increased the viral resistance to compound 15 by 16 folds. Notably, compound 15 remained effective against resistant viruses P12-VI with an $EC_{50}$ of 2.0 μM, suggesting that other sequence variations beyond V63 in NS4B protein may influence its sensitivity to compound treatment.

In Vivo PK and Efficacy of Compound 15. Considering its excellent inhibitory activities against three serotypes DENY-1 to -3, Compound 15 (JMX0254) was selected for further in vivo PK and efficacy studies. First, plasma pharmacokinetics after 10 mg/kg intravenous and 20 mg/kg oral administration of compound 15 to male SD rats were characterized. As listed in Table 5, compound 15 showed good oral exposure (6,240 ng·h/mL) and oral bioavailability (30%). Following an oral dose of 20 mg/kg, the rat plasma concentration of 15 reached a maximum (1,517 ng/mL) at 1.0 h postdose administration.

TABLE 5

Pharmacokinetic Parameters of Compound 15 Following 20 mg/kg Oral and 10 mg/kg Intravenous Dosing in Rats[a]

|    | $AUC_{0-\infty}$ (ng · h/mL) | MRT (h) | $t_{1/2}$ (h) | $T_{max}$ (h) | $C_{max}$ (ng/mL) | CL (L/h/kg) | $V_{ss}$ (L/kg) | F (%) |
|----|------|------|------|------|-------|------|-------|----|
| po | 6,240 | 3.46 | 2.24 | 1.00 | 1,517 | 3.57 | 11.54 | 30 |
| iv | 10,334 | 2.28 | 2.29 |      | 10,334 | 0.82 | 2.67 |    |

[a]$C_{max}$, maximum concentration of drug in plasma;
$T_{max}$, time to maximum concentration of drug in plasma;
AUC, area under the curve (t = 0 to 24 h);
MRT, mean residence time;
$V_{ss}$, volume of distribution at steady state;
CL, plasma clearance;
$t_{1/2}$, terminal half-life;
F, absolute oral bioavailability.
Formulation for po and iv: DMSO: 20% HP-β-CD in saline = 1:9.

Figure 3A:
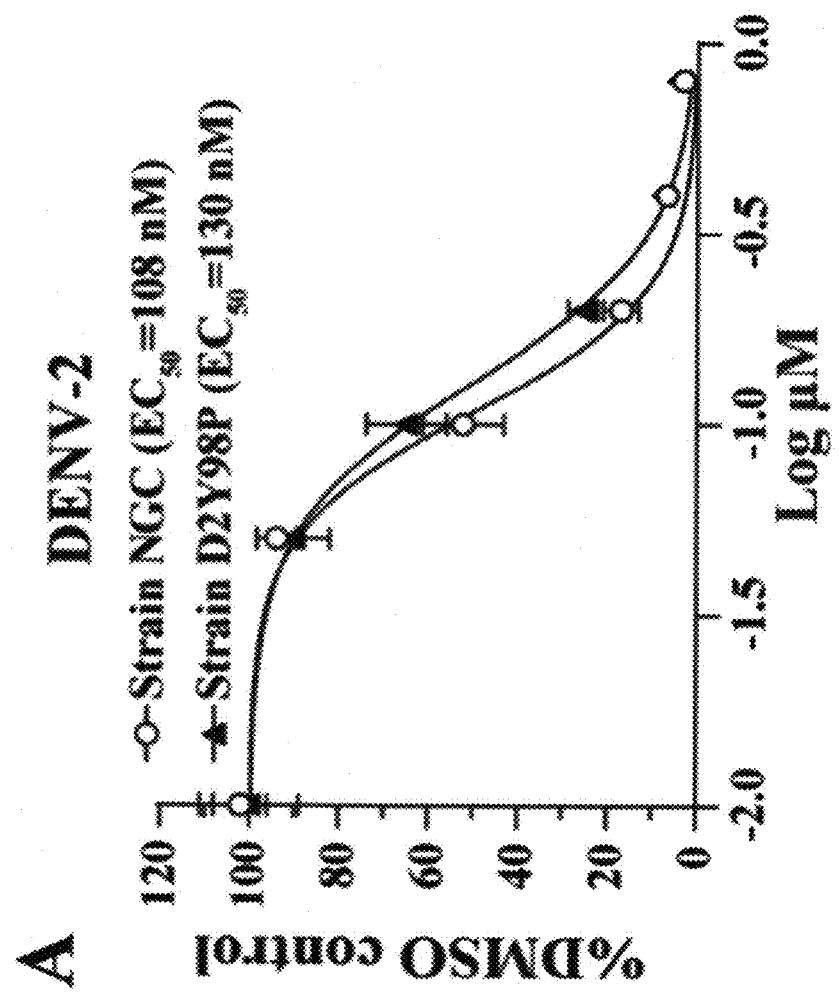
FIG. 3A-3D. In vitro activity and in vivo efficacy profile of compound 15 (JMX0254). (A) Antiviral activity of compound 15 against DENV-2 strains NGC and D2Y98P. (B) Schematic diagram of evaluating the efficacy of compound 15 against DENV-2 strain D2Y98P in vivo. 3-week old A129 mice were subcutaneously (S.C.) inoculated with $10^6$ PFU D2Y98P virus. Immediately, the mice were administrated orally at 100 mg/kg twice daily (BID) with compound 15 or vehicle for 3 days. On day 3 post-infection (p.i.), mice were retro-orbitally bled. Viremia were determined by plaque assay. (C) Viremia on day 3 p.i. (D) Mouse body weight after infection. The statistical significances between the group "vehicle+D2Y98P" and the group "compound 15+D2Y98P" are shown. *, $p<0.05$; , $p<0.01$; *, $p<0.001$.
Figure 3B:
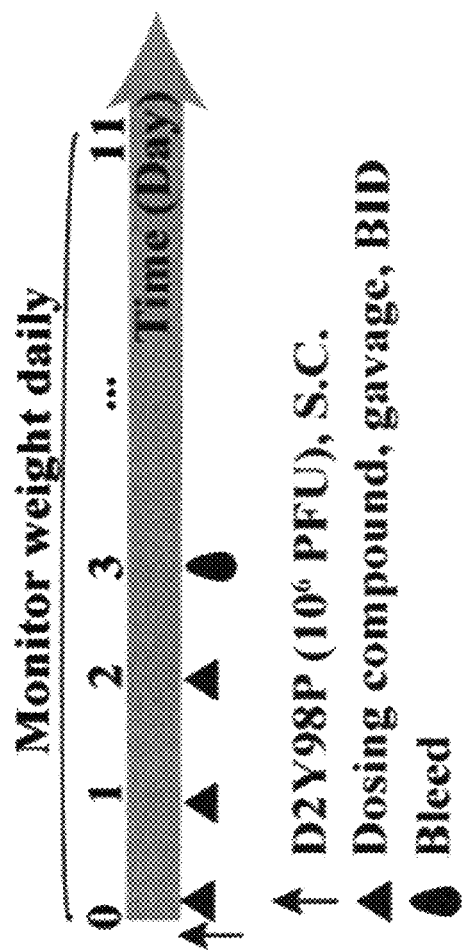
Figure 3C:
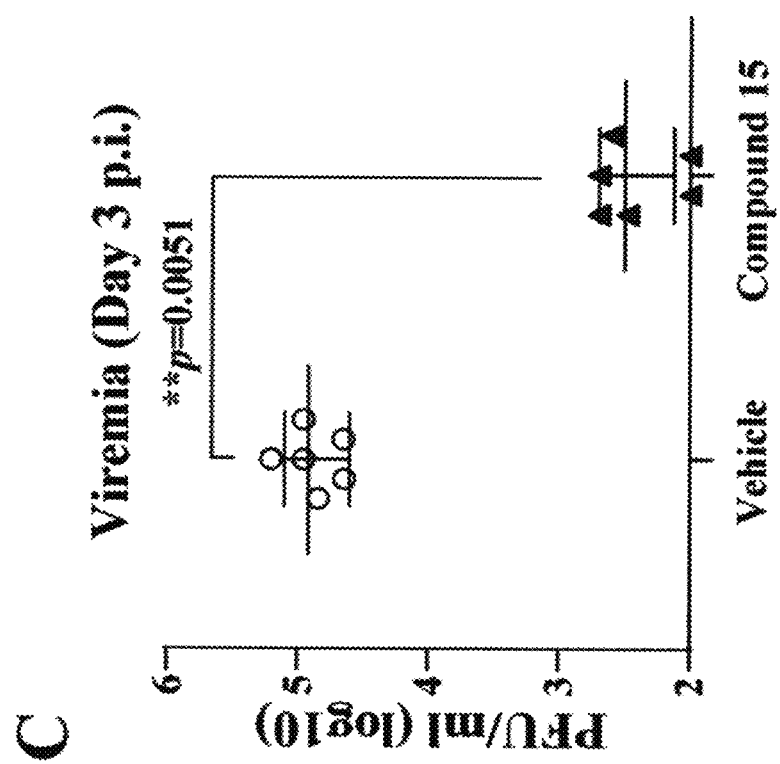
Figure 3D:
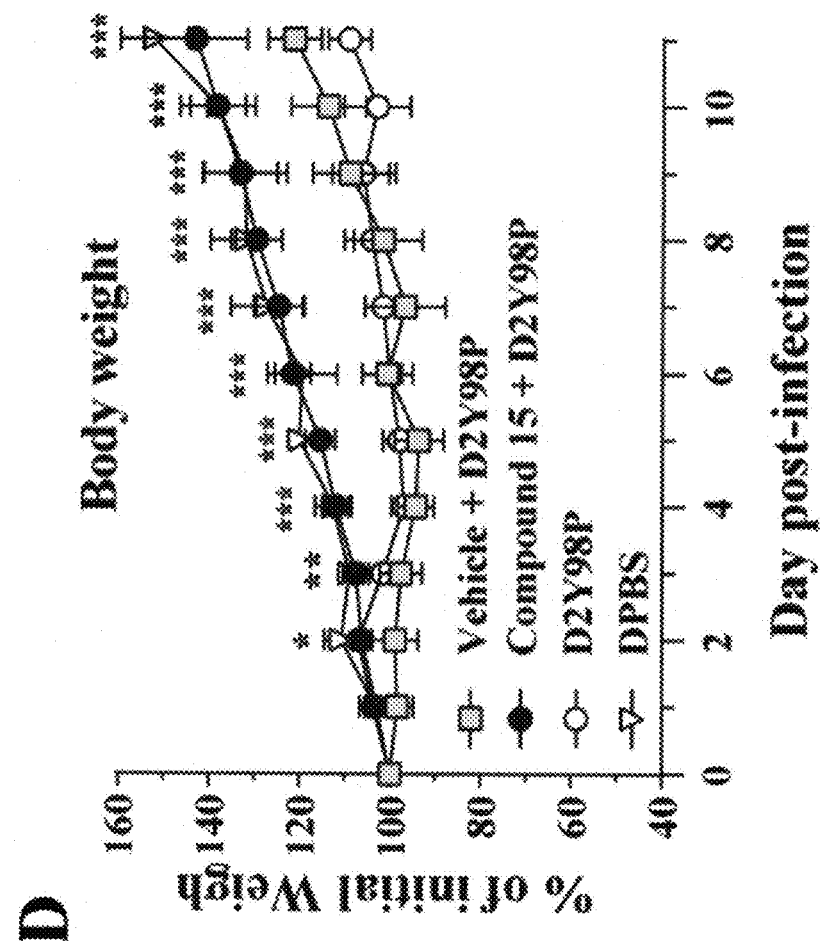
Figure 4:
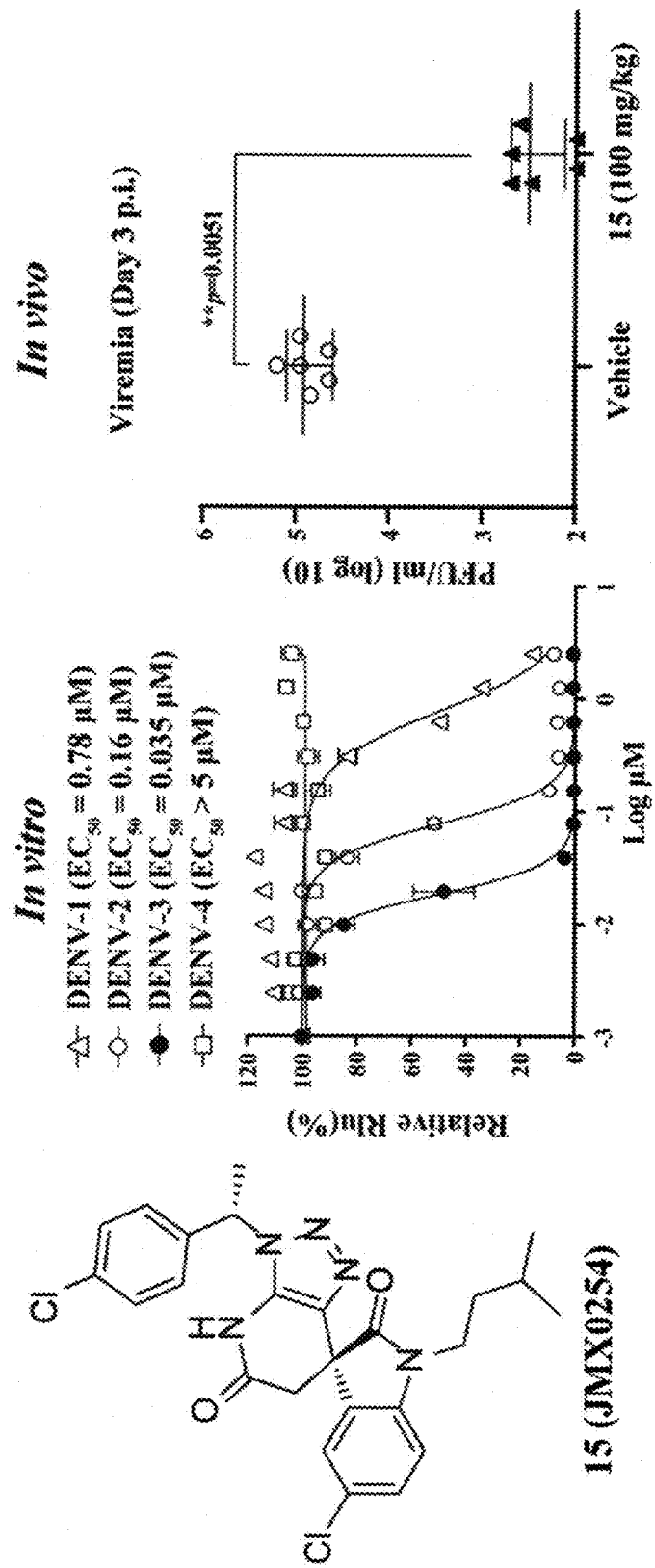
FIG. 4 In vitro activity and in vivo efficacy profile of compound 15 (JMX0254)

In vitro activity of 15 on DENV-2 strain D2Y98P, using a viral titer reduction assay. As shown in FIG. 3A, consistent with the screening results using the replicon cell line, compound 15 inhibited both DENV-2 strains NGC (for in vitro study) and D2Y98P (for in vivo study) in a dose-dependent manner on Huh7 cells, with $EC_{50}$ values of about 100 nM. The in vivo efficacy of compound 15 was then tested in a DENV-2 (strain D2Y98P) viremia A129 mouse model (FIG. 3B). Compared to vehicle control, the compound 15 treatment (when administered orally at 100 mg/kg twice daily for 3 days) significantly reduced viremia (2.4 log, p=0.0051) (FIG. 3C). In addition, this compound eliminated the morbidity caused by DENV-2 infection (FIG. 3D). In summary, compound 15 clearly demonstrated a promising efficacy profile in both cell culture and mouse model.

PREPARATION OF EXEMPLARY EMBODIMENTS

General Chemistry Information. All commercially available starting materials and solvents were reagent grade and used without further purification. Reactions were performed under a nitrogen atmosphere in dry glassware with magnetic stirring. Preparative column chromatography was performed using silica gel 60, particle size 0.063-0.200 mm (70-230 mesh, flash). Analytical TLC was carried out employing silica gel 60 F254 plates (Merck, Darmstadt). Visualization of the developed chromatograms was performed with detection by UV (254 nm). NMR spectra were recorded on a Brucker-600 and Brucker-300 ($^1$H, 600 & 300 MHz; $^{13}$C, 150 & 75 MHz) spectrometer. $^1$H and $^{13}$C NMR spectra were recorded with TMS as an internal reference. Chemical shifts were expressed in ppm, and J values were given in Hz. High-resolution mass spectra (HRMS) were obtained from Thermo Fisher LTQ Orbitrap Elite mass spectrometer. Parameters include the following: Nano ESI spray voltage was 1.8 kV; Capillary temperature was 275° C. and the resolution was 60,000; Ionization was achieved by positive mode. Melting points were measured on a Thermo Scientific Electrothermal Digital Melting Point Apparatus and uncorrected. Purities of final compounds were established by analytical HPLC, which was carried out on a Shimadzu HPLC system (model: CBM-20A LC-20AD SPD-20A UV/VIS). HPLC analysis conditions: Waters μBondapak C18 (300×3.9 mm); flow rate 0.5 mL/min; UV detection at 270 and 254 nm; linear gradient from 10% acetonitrile in water to 100% acetonitrile in water in 20 min followed by 30 min of the last-named solvent (0.1% TFA was added into both acetonitrile and water). All biologically evaluated compounds are >95% pure.

(R)-5'-Chloro-3-((S)-1-(4-chlorophenyl)ethyl)-4,6-dihydrospiro[[1,2,3]triazolo[4,5-b]pyridine-7,3'-indoline]-2',5 (3H)-dione (1a). Compound 1a was prepared by a reported route described in Scheme 1. The title compound was obtained as an off-white solid. HPLC purity 95.9% ($t_R$=17.21 min). $^1$H NMR (300 MHz, DMSO-$d_6$) δ 11.22 (s, 1H), 10.72 (s, 1H), 7.47 (d, J=8.4 Hz, 2H), 7.41-7.29 (m, 4H), 6.93 (d, J=8.4 Hz, 1H), 5.85 (q, J=6.9 Hz, 1H), 3.34 (d, J=16.2 Hz, 1H), 2.61 (d, J=16.2 Hz, 1H), 1.88 (d, J=6.9 Hz, 3H). $^{13}$C NMR (75 MHz, DMSO-$d_6$) δ 177.5, 168.5, 141.3, 139.3, 136.4, 132.7, 132.1, 128.8, 128.8 (2C), 128.5 (2C), 126.8, 126.1, 124.7, 111.4, 55.6, 46.7, 21.2. HRMS (ESI) calcd for $C_{20}H_{16}C_{12}N_5O_2$ 428.0681 (M+H)$^+$, found 428.0679.

(S)-5'-Chloro-3-((S)-1-(4-chlorophenyl)ethyl)-4,6-dihydrospiro[[1,2,3]triazolo[4,5-b]pyridine-7,3'-indoline]-2',5 (3H)-dione (1b). Compound 1b was prepared by a reported route described in Scheme 1. The title compound was obtained as an off-white solid. HPLC purity 99.8% ($t_R$=16.92 min). $^1$H NMR (300 MHz, DMSO-$d_6$) δ 11.23 (s, 1H), 10.72 (s, 1H), 7.47 (d, J=8.7 Hz, 2H), 7.41-7.30 (m, 4H), 6.93 (d, J=8.4 Hz, 1H), 5.85 (q, J=6.9 Hz, 1H), 3.34 (d, J=16.2 Hz, 1H), 2.61 (d, J=16.2 Hz, 1H), 1.87 (d, J=7.2 Hz, 3H). $^{13}$C NMR (75 MHz, DMSO-$d_6$) δ 177.5, 168.5, 141.3, 139.3, 136.4, 132.7, 132.1, 128.8, 128.8 (2C), 128.5 (2C), 126.8, 126.1, 124.7, 111.4, 55.6, 46.7, 21.2. HRMS (ESI) calcd for $C_{20}H_{16}C_{12}N_5O_2$ 428.0681 (M+H)$^+$, found 428.0677.

(R)-5'-Chloro-3-((S)-1-(4-chlorophenyl)ethyl)-1'-methyl-4,6-dihydrospiro[[1,2,3]triazolo[4,5-b]pyridine-7,3'-indoline]-2',5(3H)-dione (7). To a solution of (R)-5'-chloro-3-((S)-1-(4-chlorophenyl)ethyl)-4,6-dihydrospiro[[1,2,3]triazolo[4,5-b]pyridine-7,3'-indoline]-2',5(3H)-dione (1) (33 mg, 0.077 mmol) in anhydrous DMF (3 mL) was added NaH (6 mg, 0.15 mmol, 60% dispersion in mineral oil) at 0° C. The resulting mixture was stirred at r.t. for 30 min. Then CH$_3$I (6 μL, 0.093 mmol) was added and the resulting mixture was stirred at r.t. for 2 h till the reaction was completed monitored by TLC. The reaction mixture was poured into NH$_4$Cl (aq., 15 mL) and extracted with EtOAc/MeOH (3:1, 2×45 mL). The organic phase was washed with water (2×15 mL) and brine (15 mL), dried over Na$_2$SO$_4$ and concentrated. The residue was purified by preparative TLC developed by 60% EtOAc in hexane to afford compound 7 as a white solid (26 mg, 76%). HPLC purity 98.5% ($t_R$=18.50 min). $^1$H NMR (300 MHz, CDCl$_3$) δ 10.45 (s, 1H), 7.36 (dd, J=8.4, 2.1 Hz, 1H), 7.33-7.27 (m, 4H), 7.13 (d, J=2.1 Hz, 1H), 6.89 (d, J=8.4 Hz, 1H), 5.54 (q, J=6.9 Hz, 1H), 3.26 (s, 3H), 3.00 (s, 2H), 1.94 (d, J=6.9 Hz, 3H). $^{13}$C NMR (75 MHz, CDCl$_3$) δ 175.9, 169.9, 142.2, 138.2, 135.5, 134.6, 130.9, 129.8, 129.3 (2C), 129.2, 128.2 (2C), 127.1, 124.4, 110.2, 57.7, 46.8, 40.8, 27.0, 21.8. HRMS (ESI) calcd for $C_{21}H_{18}Cl_2N_5O_2$ 442.0838 (M+H)$^+$, found 442.0831.

(R)-5'-Chloro-3-((S)-1-(4-chlorophenyl)ethyl)-1'-ethyl-4,6-dihydrospiro[[1,2,3]triazolo[4,5-b]pyridine-7,3'-indoline]-2',5(3H)-dione (8). Compound 8 (20 mg, 93%) was prepared by a procedure similar to that used to prepare compound 7. The title compound was obtained as a white solid. HPLC purity 99.4% ($t_R$=18.58 min). $^1$H NMR (300 MHz, CDCl$_3$) δ 10.31 (s, 1H), 7.38-7.27 (m, 5H), 7.14 (d, J=1.8 Hz, 1H), 6.90 (d, J=8.4 Hz, 1H), 5.56 (q, J=6.9 Hz, 1H), 3.80 (q, J=7.2 Hz, 2H), 3.00 (s, 2H), 1.96 (d, J=6.9 Hz, 3H), 1.31 (t, J=7.2 Hz, 3H). $^{13}$C NMR (75 MHz, CDCl$_3$) δ 175.5, 170.0, 141.4, 138.2, 135.4, 134.7, 131.1, 129.7, 129.4 (2C), 129.0, 128.2 (2C), 127.3, 124.7, 110.3, 57.8, 46.7, 40.9, 35.6, 21.8, 12.7. HRMS (ESI) calcd for $C_{22}H_{20}Cl_2N_5O_2$ 456.0994 (M+H)$^+$, found 456.0986.

(R)-5'-Chloro-3-((S)-1-(4-chlorophenyl)ethyl)-1'-propyl-4,6-dihydrospiro[[1,2,3]triazolo[4,5-b]pyridine-7,3'-indoline]-2',5(3H)-dione (9). Compound 9 (20 mg, 90%) was prepared by a procedure similar to that used to prepare compound 7. The title compound was obtained as a white solid. HPLC purity 99.6% ($t_R$=19.10 min). $^1$H NMR (300 MHz, CDCl$_3$) δ 10.36 (s, 1H), 7.37-7.27 (m, 5H), 7.13 (d, J=2.1 Hz, 1H), 6.89 (d, J=8.4 Hz, 1H), 5.56 (q, J=6.9 Hz, 1H), 3.84-3.53 (m, 2H), 3.04 (d, J=16.5 Hz, 1H), 2.97 (d, J=16.8 Hz, 1H), 1.96 (d, J=6.9 Hz, 3H), 1.83-1.71 (m, 2H), 0.98 (t, J=7.5 Hz, 3H). $^{13}$C NMR (75 MHz, CDCl$_3$) δ 175.9, 170.1, 141.7, 138.2, 135.4, 134.7, 131.2, 129.7, 129.4 (2C), 128.9, 128.2 (2C), 127.4, 124.6, 110.5, 57.74, 46.7, 42.3, 40.9, 21.8, 20.8, 11.4. HRMS (ESI) calcd for $C_{23}H_{22}Cl_2N_5O_2$ 470.1151 (M+H)$^+$, found 470.1146.

(R)-1'-Butyl-5'-chloro-3-((S)-1-(4-chlorophenyl)ethyl)-4,6-dihydrospiro[[1,2,3]triazolo[4,5-b]pyridine-7,3'-indoline]-2',5(3H)-dione (10). Compound 10 (20 mg, 88%) was prepared by a procedure similar to that used to prepare compound 7. The title compound was obtained as a white solid. HPLC purity 97.7% ($t_R$=19.65 min). $^1$H NMR (300 MHz, CDCl$_3$) δ 10.32 (s, 1H), 7.36-7.27 (m, 5H), 7.13 (d, J=2.1 Hz, 1H), 6.89 (d, J=8.4 Hz, 1H), 5.56 (q, J=6.9 Hz, 1H), 3.85-3.64 (m, 2H), 3.03 (d, J=16.5 Hz, 1H), 2.97 (d, J=16.5 Hz, 1H), 1.96 (d, J=7.2 Hz, 3H), 1.76-1.61 (m, 2H), 1.48-1.33 (m, 2H), 0.95 (t, J=7.2 Hz, 3H). $^{13}$C NMR (75 MHz, CDCl$_3$) δ 175.8, 170.1, 141.7, 138.2, 135.4, 134.7, 131.2, 129.7, 129.4 (2C), 128.9, 128.2 (2C), 127.4, 124.6, 110.4, 57.8, 46.7, 40.9, 40.6, 29.5, 21.8, 20.2, 13.8. HRMS (ESI) calcd for $C_{24}H_{24}Cl_2N_5O_2$ 484.1307 (M+H)$^+$, found 484.1303.

(R)-5'-Chloro-3-((S)-1-(4-chlorophenyl)ethyl)-1'-hexyl-4,6-dihydrospiro[[1,2,3]triazolo[4,5-b]pyridine-7,3'-indoline]-2',5(3H)-dione (11). Compound 11 (21 mg, 87%) was prepared by a procedure similar to that used to prepare compound 7. The title compound was obtained as an off-white solid. HPLC purity 99.5% ($t_R$=20.81 min). $^1$H NMR (300 MHz, CDCl$_3$) δ 9.98 (s, 1H), 7.38-7.27 (m, 5H), 7.13 (d, J=2.1 Hz, 1H), 6.89 (d, J=8.4 Hz, 1H), 5.56 (q, J=6.9 Hz, 1H), 3.81-3.65 (m, 2H), 3.00 (s, 2H), 1.96 (d, J=7.2 Hz, 3H), 1.76-1.63 (m, 2H), 1.42-1.25 (m, 6H), 0.87 (t, J=6.9 Hz, 3H). $^{13}$C NMR (75 MHz, CDCl$_3$) δ 175.8, 170.1, 141.7, 138.2, 135.4, 134.7, 131.1, 129.7, 129.4 (2C), 129.0, 128.2 (2C), 127.4, 124.6, 110.4, 57.8, 46.7, 40.9, 40.8, 31.5, 27.4, 26.6, 22.6, 21.8, 14.1. HRMS (ESI) calcd for $C_{26}H_{28}Cl_2N_5O_2$ 512.1620 (M+H)$^+$, found 512.1614.

(R)-5'-Chloro-3-((S)-1-(4-chlorophenyl)ethyl)-1'-decyl-4,6-dihydrospiro[[1,2,3]triazolo[4,5-b]pyridine-7,3'-indoline]-2',5(3H)-dione (12). Compound 12 (22 mg, 83%) was prepared by a procedure similar to that used to prepare compound 7. The title compound was obtained as a white solid. HPLC purity 99.5% ($t_R$=23.61 min). $^1$H NMR (300 MHz, CDCl$_3$) δ 10.39 (s, 1H), 7.37-7.27 (m, 5H), 7.13 (d, J=2.1 Hz, 1H), 6.89 (d, J=8.4 Hz, 1H), 5.56 (q, J=6.9 Hz, 1H), 3.81-3.63 (m, 2H), 3.04-2.93 (m, 2H), 1.96 (d, J=6.9 Hz, 3H), 1.76-1.63 (m, 2H), 1.42-1.20 (m, 14H), 0.87 (t, J=6.6 Hz, 3H). $^{13}$C NMR (75 MHz, CDCl$_3$) δ 175.8, 170.1, 141.7, 138.2, 135.4, 134.7, 131.1, 129.7, 129.4 (2C), 128.9, 128.2 (2C), 127.3, 124.6, 110.4, 57.7, 46.7, 40.9, 40.9, 32.0, 29.6, 29.6, 29.4, 29.4, 27.4, 27.0, 22.8, 21.8, 14.2. HRMS (ESI) calcd for $C_{30}H_{36}Cl_2N_5O_2$ 568.2246 (M+H)$^+$, found 568.2241.

(R)-5'-Chloro-3-((S)-1-(4-chlorophenyl)ethyl)-1'-isopropyl-4,6-dihydrospiro[[1,2,3]triazolo[4,5-b]pyridine-7,3'-indoline]-2',5(3H)-dione (13). To a solution of (R)-5'-chloro-3-((S)-1-(4-chlorophenyl)ethyl)-4,6-dihydrospiro[[1,2,3]triazolo[4,5-b]pyridine-7,3'-indoline]-2',5(3H)-dione (7) (42 mg, 0.099 mmol) in anhydrous DMF (3 mL) was added NaH (16 mg, 0.40 mmol, 60% dispersion in mineral oil) at 0° C. The resulting mixture was stirred at r.t. for 30 min. Then 2-bromopropane (32 mg, 0.24 mmol) was added and the resulting mixture was stirred at 50° C. for 24 h. The reaction mixture was cooled to r.t. and poured into NH$_4$Cl (aq., 15 mL) and extracted with EtOAc/MeOH (3:1, 2×45 mL). The organic phase was washed with water (2×15 mL) and brine (15 mL), dried over Na$_2$SO$_4$ and concentrated in vacuo. The residue was purified by preparative TLC developed by 40% EtOAc in hexane to afford compound 13 as an off-white solid (12 mg, 26%). HPLC purity 95.3% ($t_R$=19.08 min). $^1$H NMR (300 MHz, CDCl$_3$) δ 10.24 (s, 1H), 7.35-7.28 (m, 5H), 7.14 (d, J=2.1 Hz, 1H), 7.03 (d, J=8.7 Hz, 1H), 5.56 (q, J=6.9 Hz, 1H), 4.65-4.50 (m, 1H), 3.03-2.91 (m, 2H), 1.97 (d, J=7.2 Hz, 3H), 1.52 (d, J=7.2 Hz, 6H). $^{13}$C NMR (75 MHz, CDCl$_3$) δ 175.6, 170.1, 141.1, 138.1, 135.4, 134.7, 131.3, 129.5, 129.4 (2C), 128.7, 128.2 (2C), 127.6, 124.7, 111.7, 57.8, 46.7, 45.0, 41.0, 21.8, 19.5, 19.5. HRMS (ESI) calcd for $C_{23}H_{22}Cl_2N_5O_2$ 470.1151 (M+H)$^+$, found 470.1146.

(R)-5'-Chloro-3-((S)-1-(4-chlorophenyl)ethyl)-1'-isobutyl-4,6-dihydrospiro[[1,2,3]triazolo[4,5-b]pyridine-7,3'-indoline]-2',5(3H)-dione (14). Compound 14 (13 mg, 57%) was prepared by a procedure similar to that used to prepare compound 7. The title compound was obtained as a light yellow solid. HPLC purity 99.4% ($t_R$=19.57 min). $^1$H NMR (300 MHz, CDCl$_3$) δ 10.36 (s, 1H), 7.36-7.27 (m, 5H), 7.12 (d, J=1.8 Hz, 1H), 6.88 (d, J=8.4 Hz, 1H), 5.56 (q, J=6.9 Hz, 1H), 3.61 (dd, J=13.8, 7.8 Hz, 1H), 3.50 (dd, J=13.8, 7.2 Hz, 1H), 3.06 (d, J=16.5 Hz, 1H), 2.98 (d, J=16.5 Hz, 1H), 2.25-2.10 (m, 1H), 1.97 (d, J=6.9 Hz, 3H), 1.03-0.94 (m, 6H). $^{13}$C NMR (75 MHz, CDCl$_3$) δ 176.1, 170.2, 142.0, 138.2, 135.3, 134.7, 131.2, 129.6, 129.4 (2C), 128.9, 128.2 (2C), 127.5, 124.5, 110.7, 57.8, 48.1, 46.7, 40.9, 27.1, 21.8, 20.3, 20.2. HRMS (ESI) calcd for C$_{24}$H$_{24}$Cl$_2$N$_5$O$_2$ 484.1307 (M+H)$^+$, found 484.1299.

(R)-5'-Chloro-3-((S)-1-(4-chlorophenyl)ethyl)-1'-isopentyl-4,6-dihydrospiro[[1,2,3]triazolo[4,5-b]pyridine-7,3'-indoline]-2',5(3H)-dione (15). Compound 15 (18 mg, 77%) was prepared by a procedure similar to that used to prepare compound 7. The title compound was obtained as an off-white solid. $^1$H NMR (300 MHz, CDCl$_3$) δ 10.42 (s, 1H), 7.38-7.26 (m, 5H), 7.13 (d, J=2.1 Hz, 1H), 6.88 (d, J=8.4 Hz, 1H), 5.56 (q, J=6.9 Hz, 1H), 3.87-3.60 (m, 2H), 2.99 (s, 2H), 1.97 (d, J=6.9 Hz, 3H), 1.73-1.54 (m, 3H), 0.98 (d, J=6.3 Hz, 6H). $^{13}$C NMR (75 MHz, CDCl$_3$) δ 175.7, 170.2, 141.6, 138.2, 135.4, 134.7, 131.1, 129.7, 129.4 (2C), 128.9, 128.2 (2C), 127.3, 124.6, 110.4, 57.7, 46.7, 40.9, 39.2, 36.0, 26.1, 22.6, 22.5, 21.8. HRMS (ESI) calcd for C$_{25}$H$_{26}$Cl$_2$N$_5$O$_2$ 498.1464 (M+H)$^+$, found 498.1457.

(R)-5'-Chloro-3-((S)-1-(4-chlorophenyl)ethyl)-1'-(3,3-dimethylbutyl)-4,6-dihydrospiro[[1,2,3]triazolo[4,5-b]pyridine-7,3'-indoline]-2',5(3H)-dione (16). Compound 16 (29 mg, 65%) was prepared by a procedure similar to that used to prepare compound 7. The title compound was obtained as a yellow solid. HPLC purity 99.6% ($t_R$=19.71 min). $^1$H NMR (300 MHz, CDCl$_3$) δ 10.50 (s, 1H), 7.39-7.26 (m, 5H), 7.13 (d, J=2.1 Hz, 1H), 6.85 (d, J=8.4 Hz, 1H), 5.56 (d, J=6.9 Hz, 1H), 3.84-3.64 (m, 2H), 2.99 (s, 2H), 1.95 (d, J=6.9 Hz, 3H), 1.67-1.50 (m, 2H), 1.02 (s, 9H). $^{13}$C NMR (75 MHz, CDCl$_3$) δ 175.6, 170.1, 141.6, 138.3, 135.4, 134.6, 131.2, 129.7, 129.3 (2C), 128.9, 128.2 (2C), 127.2, 124.6, 110.2, 57.7, 46.7, 40.8, 40.4, 37.4, 30.1, 29.3 (3C), 21.8. HRMS (ESI) calcd for C$_{26}$H$_{28}$Cl$_2$N$_5$O$_2$ 512.1620 (M+H)$^+$, found 512.1617.

(R)-5'-Chloro-3-((S)-1-(4-chlorophenyl)ethyl)-1'-(cyclopropylmethyl)-4,6-dihydrospiro[[1,2,3]triazolo[4,5-b]pyridine-7,3'-indoline]-2',5(3H)-dione (17). Compound 17 (43 mg, 84%) was prepared by a procedure similar to that used to prepare compound 7. The title compound was obtained as an off-white solid. HPLC purity 98.4% ($t_R$=19.58 min). $^1$H NMR (300 MHz, CDCl$_3$) δ 10.56 (s, 1H), 7.37-7.26 (m, 5H), 7.13 (d, J=2.1 Hz, 1H), 6.97 (d, J=8.4 Hz, 1H), 5.67-5.42 (q, J=6.9 Hz, 1H), 3.64 (d, J=6.9 Hz, 2H), 3.05 (d, J=16.5 Hz, 1H), 2.98 (d, J=16.5 Hz, 1H), 1.95 (d, J=6.9 Hz, 3H), 1.22-1.10 (m, 1H), 0.61-0.53 (m, 2H), 0.44-0.35 (m, 2H). $^{13}$C NMR (75 MHz, CDCl$_3$) δ 175.9, 170.2, 141.9, 138.3, 135.4, 134.6, 131.1, 129.7, 129.3 (2C), 128.9, 128.2 (2C), 127.2, 124.5, 110.6, 57.7, 46.8, 45.1, 41.0, 21.8, 9.6, 4.2, 4.1. HRMS (ESI) calcd for C$_{24}$H$_{22}$Cl$_2$N$_5$O$_2$ 482.1151 (M+H)$^+$, found 482.1146.

(R)-1'-Allyl-5'-chloro-3-((S)-1-(4-chlorophenyl)ethyl)-4,6-dihydrospiro[[1,2,3]triazolo[4,5-b]pyridine-7,3'-indoline]-2',5(3H)-dione (18). Compound 18 (22 mg, 70%) was prepared by a procedure similar to that used to prepare compound 7. The title compound was obtained as a light-yellow solid. HPLC purity 98.1% ($t_R$=19.54 min). $^1$H NMR (300 MHz, CDCl$_3$) δ 10.08 (s, 1H), 7.37-7.28 (m, 5H), 7.15 (d, J=2.1 Hz, 1H), 6.87 (d, J=8.4 Hz, 1H), 5.93-5.78 (m, 1H), 5.53 (q, J=6.9 Hz, 1H), 5.34-5.23 (m, 2H), 4.48-4.29 (m, 2H), 3.09-2.95 (m, 2H), 1.95 (d, J=6.9 Hz, 3H). $^{13}$C NMR (75 MHz, CDCl$_3$) δ 175.7, 169.8, 141.4, 138.2, 135.4, 134.7, 130.9, 130.4, 129.7, 129.4 (2C), 129.2, 128.2 (2C), 127.3, 124.5, 118.3, 111.1, 57.8, 46.8, 42.9, 40.8, 21.8. HRMS (ESI) calcd for C$_{23}$H$_{20}$Cl$_2$N$_5$O$_2$ 468.0994 (M+H)$^+$, found 468.0988.

(R)-5'-Chloro-3-((S)-1-(4-chlorophenyl)ethyl)-1'-(prop-2-yn-1-yl)-4,6-dihydrospiro[[1,2,3]triazolo[4,5-b]pyridine-7,3'-indoline]-2',5(3H)-dione (19). To a solution of (R)-5'-chloro-3-((S)-1-(4-chlorophenyl)ethyl)-4,6-dihydrospiro[[1,2,3]triazolo[4,5-b]pyridine-7,3'-indoline]-2',5(3H)-dione (1) (41 mg, 0.096 mmol) in anhydrous DMF (4 mL) was added NaH (8 mg, 0.19 mmol, 60% dispersion in mineral oil) at 0° C. The resulting mixture was stirred at r.t. for 30 min. Then propargyl bromide (14 mg, 0.12 mmol) was added at 0° C., and the resulting mixture was stirred at 0° C. for 30 min. The reaction mixture was then poured into NH$_4$Cl (aq., 15 mL) and extracted with EtOAc/MeOH (3:1, 2×50 mL). The organic phase was washed with water (2×15 mL) and brine (15 mL), dried over Na$_2$SO$_4$ and concentrated in vacuo. The residue was purified by preparative TLC developed by 50% EtOAc in hexane to afford compound 19 as a yellow solid (41 mg, 85%). HPLC purity 97.4% ($t_R$=18.96 min). $^1$H NMR (300 MHz, CDCl$_3$) δ 10.52 (s, 1H), 7.39 (dd, J=8.4, 2.1 Hz, 1H), 7.34-7.27 (m, 4H), 7.17 (d, J=1.8 Hz, 1H), 7.12 (d, J=8.4 Hz, 1H), 5.54 (q, J=6.9 Hz, 1H), 4.63 (dd, J=17.8, 2.4 Hz, 1H), 4.46 (dd, J=17.8, 2.4 Hz, 1H), 3.02 (s, 2H), 2.32 (t, J=2.4 Hz, 1H), 1.93 (d, J=7.2 Hz, 3H). $^{13}$C NMR (75 MHz, CDCl$_3$) δ 175.1, 169.8, 140.3, 138.3, 135.6, 134.6, 130.6, 129.8, 129.7, 129.3 (2C), 128.2 (2C), 126.8, 124.6, 111.3, 76.1, 73.5, 57.8, 46.8, 40.8, 30.1, 21.9. HRMS (ESI) calcd for C$_{23}$H$_{18}$Cl$_2$N$_5$O$_2$ 466.0838 (M+H)$^+$, found 466.0833.

(R)-1'-(But-2-yn-1-yl)-5'-chloro-3-((S)-1-(4-chlorophenyl)ethyl)-4,6-dihydrospiro[[1,2,3]triazolo[4,5-b]pyridine-7,3'-indoline]-2',5(3H)-dione (20). Compound 20 (40 mg, 79%) was prepared by a procedure similar to that used to prepare compound 7. The title compound was obtained as an off-white solid. HPLC purity 98.8% ($t_R$=19.08 min). $^1$H NMR (300 MHz, CDCl$_3$) δ 10.45 (s, 1H), 7.38 (dd, J=8.4, 2.1 Hz, 1H), 7.34-7.27 (m, 4H), 7.16 (d, J=2.1 Hz, 1H), 7.11 (d, J=8.4 Hz, 1H), 5.49 (q, J=6.9 Hz, 1H), 4.59-4.37 (m, 2H), 3.00 (s, 2H), 1.90 (d, J=6.9 Hz, 3H), 1.78 (s, 3H). $^{13}$C NMR (75 MHz, CDCl$_3$) δ 175.2, 169.5, 140.7, 138.4, 135.8, 134.5, 130.7, 129.7, 129.5, 129.3 (2C), 128.2 (2C), 126.9, 124.5, 111.4, 81.3, 71.5, 57.7, 46.8, 40.9, 30.5, 21.8, 3.6. HRMS (ESI) calcd for C$_{24}$H$_{20}$Cl$_2$N$_5$O$_2$ 480.0994 (M+H)$^+$, found 480.0991.

(R)-5'-Chloro-3-((S)-1-(4-chlorophenyl)ethyl)-4-isopropyl-4,6-dihydrospiro[[1,2,3]triazolo[4,5-b]pyridine-7,3'-indoline]-2',5(3H)-dione (21). Compound 21 (9 mg, 19%) was prepared by a procedure same to that used to prepare compound 13. The title compound was obtained as a white solid. HPLC purity 97.0% ($t_R$=20.85 min). $^1$H NMR (300 MHz, CDCl$_3$) δ 8.80 (br s, 1H), 7.40-7.30 (m, 4H), 7.10-7.02 (m, 1H), 6.91 (d, J=1.8 Hz, 1H), 6.60 (d, J=8.4 Hz, 1H), 5.80 (q, J=7.2 Hz, 1H), 5.39-5.20 (m, 1H), 3.06 (d, J=17.4 Hz, 1H), 2.73 (d, J=17.4 Hz, 1H), 2.02 (d, J=7.2 Hz, 3H), 1.36-1.30 (m, 6H). $^{13}$C NMR (75 MHz, CDCl$_3$) δ 177.7, 168.0, 142.4, 139.3, 139.1, 134.1, 133.4, 129.2, 129.1 (2C), 128.9, 128.6 (2C), 128.1, 124.0, 111.7, 71.6, 57.1, 47.1, 36.8, 21.7, 21.6, 20.8. HRMS (ESI) calcd for C$_{23}$H$_{22}$Cl$_2$N$_5$O$_2$ 470.1151 (M+H)$^+$, found 470.1143.

(R)-5'-Chloro-3-((S)-1-(4-chlorophenyl)ethyl)-1',4-diisopropyl-4,6-dihydrospiro[[1,2,3]triazolo[4,5-b]pyridine-7,3'-indoline]-2',5(3H)-dione (22). compound 22 (7.4 mg, 14%) was prepared by a procedure same to that used to prepare compound 13. The title compound was obtained as a light-yellow solid. HPLC purity 99.3% ($t_R$=22.62 min). $^1$H NMR (300 MHz, CDCl$_3$) δ 7.39-7.27 (m, 4H), 7.26-7.21 (m, 1H), 7.01 (d, J=2.1 Hz, 1H), 6.96 (d, J=8.7 Hz, 1H), 5.77 (q, J=7.2 Hz, 1H), 5.37-5.23 (m, 1H), 4.64-4.49 (m, 1H), 2.93 (d, J=17.4 Hz, 1H), 2.74 (d, J=17.1 Hz, 1H), 2.00 (d, J=7.5 Hz, 3H), 1.51-1.45 (m, 6H), 1.38-1.28 (m, 6H). $^{13}$C NMR (75 MHz, CDCl$_3$) δ 175.9, 167.8, 142.3, 140.7, 139.4, 134.0, 133.4, 129.0 (3C), 128.9, 128.5 (2C), 128.3, 124.4, 111.4, 71.4, 56.9, 46.6, 44.7, 37.0, 21.7, 21.6, 21.0, 19.5, 19.5. HRMS (ESI) calcd for C$_{26}$H$_{28}$Cl$_2$N$_5$O$_2$ 512.1620 (M+H)$^+$, found 512.1622.

(S)-5'-Chloro-3-((S)-1-(4-chlorophenyl)ethyl)-1',4,6,6-tetramethyl-4,6-dihydrospiro[[1,2,3]triazolo[4,5-b]pyridine-7,3'-indoline]-2',5(3H)-dione (23). To a solution of (R)-5'-chloro-3-((S)-1-(4-chlorophenyl)ethyl)-4,6-dihydrospiro[[1,2,3]triazolo[4,5-b]pyridine-7,3'-indoline]-2',5(3H)-dione (1) (42 mg, 0.098 mmol) in anhydrous DMF (4 mL) was added NaH (24 mg, 0.59 mmol, 60% dispersion in mineral oil) at 0° C. The resulting mixture was stirred at r.t. for 30 min. Then CH$_3$I (37 μL, 0.59 mmol) was added and the resulting mixture was stirred at r.t. for 2 h till the reaction was completed monitored by TLC. The reaction mixture was poured into NH$_4$Cl (aq., 15 mL) and extracted with EtOAc/MeOH (3:1, 2×45 mL). The organic phase was washed with water (2×15 mL) and brine (15 mL), dried over Na$_2$SO$_4$ and concentrated. The residue was purified by preparative TLC developed by 40% EtOAc in hexane to afford compound 23 as a white solid (41 mg, 86%). HPLC purity 98.0% ($t_R$=20.73 min). $^1$H NMR (300 MHz, CDCl$_3$) δ 7.38 (dd, J=8.4, 2.1 Hz, 1H), 7.35-7.28 (m, 3H), 7.07-7.01 (m, 2H), 6.85 (d, J=8.1 Hz, 1H), 5.78 (q, J=6.9 Hz, 1H), 3.36 (s, 3H), 3.14 (s, 3H), 2.06 (d, J=6.9 Hz, 3H), 1.09 (s, 3H), 0.90 (s, 3H). $^{13}$C NMR (75 MHz, CDCl$_3$) δ 175.5, 174.2, 143.6, 139.6, 138.0, 134.5, 130.8, 129.7, 129.5 (2C), 128.4, 127.0 (2C), 126.9, 126.5, 109.8, 59.5, 54.4, 46.8, 31.3, 26.4, 22.4, 21.5, 18.9. HRMS (ESI) calcd for C$_{24}$H$_{24}$Cl$_2$N$_5$O$_2$ 484.1307 (M+H)$^+$, found 484.1304.

(R)-1'-Benzyl-5'-chloro-3-((S)-1-(4-chlorophenyl)ethyl)-4,6-dihydrospiro[[1,2,3]triazolo[4,5-b]pyridine-7,3'-indoline]-2',5(3H)-dione (24). Compound 24 (47 mg, 85%) was prepared by a procedure similar to that used to prepare compound 7. The title compound was obtained as a white solid. HPLC purity 99.9% ($t_R$=20.11 min). $^1$H NMR (300 MHz, CDCl$_3$) δ 10.62 (s, 1H), 7.38-7.28 (m, 5H), 7.27-7.18 (m, 5H), 7.14 (d, J=1.8 Hz, 1H), 6.73 (d, J=8.4 Hz, 1H), 5.53 (q, J=6.9 Hz, 1H), 5.06 (d, J=15.9 Hz, 1H), 4.91 (d, J=15.9 Hz, 1H), 3.15 (d, J=16.5 Hz, 1H), 3.03 (d, J=16.8 Hz, 1H), 1.90 (d, J=6.9 Hz, 3H). $^{13}$C NMR (75 MHz, CDCl$_3$) δ 176.3, 169.8, 141.2, 138.3, 135.6, 134.6, 134.4, 131.1, 129.6, 129.3, 129.2 (2C), 129.2 (2C), 128.1 (2C), 127.1 (2C), 127.0, 124.4, 111.2, 57.7, 46.9, 44.3, 40.8, 21.8. HRMS (ESI) calcd for C$_{27}$H$_{22}$Cl$_2$N$_5$O$_2$ 518.1151 (M+H)$^+$, found 518.1159.

(R)-5'-Chloro-3-((S)-1-(4-chlorophenyl)ethyl)-1'-(4-fluorobenzyl)-4,6-dihydrospiro[[1,2,3]triazolo[4,5-b]pyridine-7,3'-indoline]-2',5(3H)-dione (25). Compound 25 (29 mg, 92%) was prepared by a procedure similar to that used to prepare compound 7. The title compound was obtained as a light yellow solid. HPLC purity 99.5% ($t_R$=20.17 min). $^1$H NMR (300 MHz, CDCl$_3$) δ 10.50 (s, 1H), 7.33-7.27 (m, 6H), 7.24 (dd, J=8.4, 2.1 Hz, 1H), 7.14 (d, J=2.1 Hz, 1H), 7.09-6.97 (m, 2H), 6.72 (d, J=8.4 Hz, 1H), 5.57 (q, J=6.9 Hz, 1H), 5.02 (d, J=15.9 Hz, 1H), 4.84 (d, J=15.9 Hz, 1H), 3.13 (d, J=16.5 Hz, 1H), 3.03 (d, J=16.5 Hz, 1H), 1.96 (d, J=6.9 Hz, 3H). $^{13}$C NMR (75 MHz, CDCl$_3$) δ 175.6, 169.9, 162.4 (d, J=245.4 Hz), 140.9, 138.0, 135.3, 134.5, 131.0, 130.3 (d, J=3.3 Hz), 129.6, 129.3 (3C), 128.8 (d, J=8.2 Hz, 2C), 128.0 (2C), 127.1, 124.4, 116.1 (d, J=21.6 Hz, 2C), 111.0, 57.7, 46.7, 43.6, 40.6, 21.7. HRMS (ESI) calcd for C$_{27}$H$_{21}$Cl$_2$FN$_5$O$_2$ 536.1056 (M+H)$^+$, found 536.1052.

(R)-5'-Chloro-3-((S)-1-(4-chlorophenyl)ethyl)-1'-(3-fluorobenzyl)-4,6-dihydrospiro[[1,2,3]triazolo[4,5-b]pyridine-7,3'-indoline]-2',5(3H)-dione (26). Compound 26 (30 mg, 95%) was prepared by a procedure similar to that used to prepare compound 7. The title compound was obtained as a light yellow solid. HPLC purity 99.3% ($t_R$=20.18 min). $^1$H NMR (300 MHz, CDCl$_3$) δ 10.54 (s, 1H), 7.36-7.26 (m, 5H), 7.26-7.21 (m, 1H), 7.17-7.06 (m, 2H), 7.05-6.93 (m, 2H), 6.72 (d, J=8.4 Hz, 1H), 5.55 (q, J=6.9 Hz, 1H), 5.02 (d, J=15.9 Hz, 1H), 4.90 (d, J=15.9 Hz, 1H), 3.14 (d, J=16.5 Hz, 1H), 3.04 (d, J=16.5 Hz, 1H), 1.94 (d, J=6.9 Hz, 3H). $^{13}$C NMR (75 MHz, CDCl$_3$) δ 176.2, 170.0, 163.2 (d, J=246.0 Hz), 140.9, 138.2, 137.3 (d, J=7.0 Hz), 135.4, 134.6, 131.1, 130.9 (d, J=8.3 Hz), 129.8, 129.5, 129.3 (2C), 128.1 (2C), 127.1, 124.6, 122.6 (d, J=2.9 Hz), 115.2 (d, J=20.9 Hz), 114.2 (d, J=22.0 Hz), 111.1, 57.8, 46.8, 43.9, 40.7, 21.8. HRMS (ESI) calcd for C$_{27}$H$_{21}$Cl$_2$FN$_5$O$_2$ 536.1056 (M+H)$^+$, found 536.1052.

(R)-5'-Chloro-1'-(4-chlorobenzyl)-3-((S)-1-(4-chlorophenyl)ethyl)-4,6-dihydrospiro[[1,2,3]triazolo[4,5-b]pyridine-7,3'-indoline]-2',5(3H)-dione (27). Compound 27 (57 mg, 94%) was prepared by a procedure similar to that used to prepare compound 7. The title compound was obtained as an off-white solid. HPLC purity 99.8% ($t_R$=20.11 min). $^1$H NMR (300 MHz, CDCl$_3$) δ 10.62 (s, 1H), 7.34-7.20 (m, 9H), 7.13 (d, J=1.8 Hz, 1H), 6.70 (d, J=8.4 Hz, 1H), 5.56 (q, J=6.9 Hz, 1H), 5.00 (d, J=15.9 Hz, 1H), 4.83 (d, J=15.9 Hz, 1H), 3.12 (d, J=16.5 Hz, 1H), 3.03 (d, J=16.5 Hz, 1H), 1.95 (d, J=7.2 Hz, 3H). $^{13}$C NMR (75 MHz, CDCl$_3$) δ 176.1, 170.1, 140.9, 138.2, 135.4, 134.6, 134.1, 133.2, 131.1, 129.7, 129.4, 129.4 (2C), 129.3 (2C), 128.5 (2C), 128.1 (2C), 127.1, 124.5, 111.0, 57.8, 46.8, 43.7, 40.6, 21.8. HRMS (ESI) calcd for C$_{27}$H$_{21}$Cl$_3$N$_5$O$_2$ 552.0761 (M+H)$^+$, found 552.0761.

(R)-5'-Chloro-1'-(4-chloro-3-fluorobenzyl)-3-((S)-1-(4-chlorophenyl)ethyl)-4,6-dihydrospiro[[1,2,3]triazolo[4,5-b]pyridine-7,3'-indoline]-2',5(3H)-dione (28). Compound 28 (15 mg, 30%) was prepared by a procedure similar to that used to prepare compound 7. The title compound was obtained as a yellow solid. HPLC purity 95.8% ($t_R$=19.66 min). $^1$H NMR (300 MHz, CDCl$_3$) δ 10.05 (s, 1H), 7.43-7.27 (m, 5H), 7.26-7.22 (m, 1H), 7.18-7.02 (m, 3H), 6.69 (d, J=8.4 Hz, 1H), 5.58 (q, J=6.9 Hz, 1H), 4.98 (d, J=16.2 Hz, 1H), 4.84 (d, J=16.2 Hz, 1H), 3.11 (d, J=16.5 Hz, 1H), 3.03 (d, J=16.5 Hz, 1H), 2.00 (d, J=6.9 Hz, 3H). $^{13}$C NMR (75 MHz, CDCl$_3$) δ 175.9, 169.7, 158.5 (d, J=249.0 Hz), 140.7, 137.9, 135.7 (d, J=6.3 Hz), 135.1 (d, J=29.6 Hz), 131.5 (2C), 131.0, 129.8, 129.6, 129.5 (2C), 128.1 (2C), 127.3, 124.7, 123.5 (d, J=3.7 Hz), 121.0 (d, J=17.6 Hz), 115.6 (d, J=21.8 Hz), 110.9, 58.0, 46.8, 43.5, 40.6, 21.8. HRMS (ESI) calcd for C$_{27}$H$_{20}$Cl$_3$FN$_5$O$_2$ 570.0667 (M+H)$^+$, found 570.0668.

(R)-5'-Chloro-3-((S)-1-(4-chlorophenyl)ethyl)-1'-(3-methoxybenzyl)-4,6-dihydrospiro[[1,2,3]triazolo[4,5-b]pyridine-7,3'-indoline]-2',5(3H)-dione (29). Compound 29 (49 mg, 93%) was prepared by a procedure similar to that used to prepare compound 7. The title compound was obtained as a yellow solid. HPLC purity 99.6% ($t_R$=18.97 min). $^1$H NMR (300 MHz, CDCl$_3$) δ 10.35 (s, 1H), 7.32-7.22 (m, 6H), 7.16 (d, J=2.1 Hz, 1H), 6.93-6.80 (m, 3H), 6.76 (d, J=8.4 Hz, 1H), 5.53 (q, J=6.9 Hz, 1H), 5.05 (d, J=15.9 Hz, 1H), 4.88 (d, J=15.9 Hz, 1H), 3.79 (s, 3H), 3.15 (d, J=16.5 Hz, 1H), 3.05 (d, J=16.5 Hz, 1H), 1.94 (d, J=6.9 Hz, 3H). $^{13}$C NMR (75 MHz, CDCl$_3$) δ 176.3, 169.7, 160.3, 141.2, 138.3, 136.2, 135.5, 134.4, 131.1, 130.3, 129.7, 129.3, 129.3 (2C), 128.1 (2C), 127.1, 124.4, 119.1, 113.4, 112.7, 111.2, 57.7, 55.4, 46.9, 44.2, 40.7, 21.8. HRMS (ESI) calcd for $C_{28}H_{24}Cl_2N_5O_3$ 548.1256 (M+H)$^+$, found 548.1256.

(R)-5'-Chloro-3-((S)-1-(4-chlorophenyl)ethyl)-1'-(3,5-dimethoxybenzyl)-4,6-dihydrospiro[[1,2,3]triazolo[4,5-b]pyridine-7,3'-indoline]-2',5(3H)-dione (30). Compound 30 (30 mg, 53%) was prepared by a procedure similar to that used to prepare compound 7. The title compound was obtained as a yellow solid. HPLC purity 99.8% ($t_R$=19.11 min). $^1$H NMR (300 MHz, CDCl$_3$) δ 10.48 (s, 1H), 7.29-7.18 (m, 5H), 7.13 (d, J=1.8 Hz, 1H), 6.76 (d, J=8.4 Hz, 1H), 6.44 (d, J=2.1 Hz, 2H), 6.33 (t, J=2.1 Hz, 1H), 5.47 (q, J=6.9 Hz, 1H), 5.02 (d, J=15.9 Hz, 1H), 4.79 (d, J=15.9 Hz, 1H), 3.74 (s, 6H), 3.14 (d, J=16.5 Hz, 1H), 3.03 (d, J=16.5 Hz, 1H), 1.88 (d, J=6.9 Hz, 3H). $^{13}$C NMR (75 MHz, CDCl$_3$) δ 176.3, 169.7, 161.5 (2C), 141.2, 138.3, 137.0, 135.5, 134.4, 131.1, 129.7, 129.3, 129.2 (2C), 128.1 (2C), 127.1, 124.4, 111.2, 104.8 (2C), 99.6, 57.7, 55.5 (2C), 46.9, 44.2, 40.6, 21.7. HRMS (ESI) calcd for $C_{29}H_{26}Cl_2N_5O_4$ 578.1362 (M+H)$^+$, found 578.1364.

(R)-5'-Chloro-3-((S)-1-(4-chlorophenyl)ethyl)-1'-(3,5-di-tert-butylbenzyl)-4,6-dihydrospiro[[1,2,3]triazolo[4,5-b]pyridine-7,3'-indoline]-2',5(3H)-dione (31). Compound 31 (45 mg, 87%) was prepared by a procedure similar to that used to prepare compound 7. The title compound was obtained as a yellow solid. HPLC purity 99.5% ($t_R$=21.93 min). $^1$H (300 MHz, CDCl$_3$) δ 10.55 (s, 1H), 7.36-7.22 (m, 6H), 7.17-7.11 (m, 3H), 6.78 (d, J=8.4 Hz, 1H), 5.57 (q, J=6.9 Hz, 1H), 4.94 (s, 2H), 3.05 (s, 2H), 1.96 (d, J=6.9 Hz, 3H), 1.30 (s, 18H). $^{13}$C NMR (75 MHz, CDCl$_3$) δ 176.1, 170.1, 151.7 (2C), 141.6, 138.3, 135.5, 134.5, 134.0, 130.9, 129.6, 129.3 (2C), 129.1, 128.2 (2C), 127.2, 124.5, 122.0, 121.3 (2C), 111.2, 57.7, 46.8, 44.7, 41.0, 35.0 (2C), 31.5 (6C), 21.9. HRMS (ESI) calcd for $C_{35}H_{38}Cl_2N_5O_2$ 630.2403 (M+H)$^+$, found 630.2400.

(R)-5'-Chloro-3-((S)-1-(4-chlorophenyl)ethyl)-1'-phenethyl-4,6-dihydrospiro[[1,2,3]triazolo[4,5-b]pyridine-7,3'-indoline]-2',5(3H)-dione (32). Compound 32 (16 mg, 64%) was prepared by a procedure similar to that used to prepare compound 7. The title compound was obtained as a white solid. HPLC purity 99.4% ($t_R$=19.95 min). 41 NMR (300 MHz, CDCl$_3$) δ 10.23 (s, 1H), 7.35-7.25 (m, 7H), 7.24-7.17 (m, 3H), 7.11 (d, J=1.8 Hz, 1H), 6.75 (d, J=8.4 Hz, 1H), 5.58 (q, J=6.9 Hz, 1H), 4.08-3.87 (m, 2H), 3.01 (t, J=7.2 Hz, 2H), 2.92 (d, J=16.5 Hz, 1H), 2.82 (d, J=16.5 Hz, 1H), 1.99 (d, J=7.2 Hz, 3H). $^{13}$C NMR (75 MHz, CDCl$_3$) δ 175.6, 170.0, 141.6, 138.1, 137.7, 135.3, 134.7, 130.8, 129.6, 129.4 (2C), 129.1 (2C), 128.9 (3C), 128.2 (2C), 127.3, 127.0, 124.6, 110.3, 57.8, 46.6, 42.1, 40.8, 33.7, 21.8. HRMS (ESI) calcd for $C_{28}H_{24}Cl_2N_5O_2$ 532.1307 (M+H)$^+$, found 532.1305.

(R)-5'-chloro-3-((S)-1-(4-chlorophenyl)ethyl)-1'-(pyridin-2-ylmethyl)-4,6-dihydrospiro[[1,2,3]triazolo[4,5-b]pyridine-7,3'-indoline]-2',5(3H)-dione (33). Compound 33 (32 mg, 87%) was prepared by a procedure similar to that used to prepare compound 7. The title compound was obtained as a light yellow solid. HPLC purity 99.8% ($t_R$=19.08 min). $^1$H NMR (300 MHz, CDCl$_3$) δ 10.63 (s, 1H), 8.55 (d, J=4.2 Hz, 1H), 7.64 (td, J=7.8, 1.8 Hz, 1H), 7.31-7.26 (m, 5H), 7.25-7.16 (m, 2H), 7.13 (d, J=2.1 Hz, 1H), 6.84 (d, J=8.4 Hz, 1H), 5.56 (q, J=6.9 Hz, 1H), 5.19 (d, J=16.2 Hz, 1H), 4.98 (d, J=16.2 Hz, 1H), 3.17 (d, J=16.8 Hz, 1H), 3.04 (d, J=16.5 Hz, 1H), 1.92 (d, J=6.9 Hz, 3H). $^{13}$C NMR (75 MHz, CDCl$_3$) δ 176.1, 170.0, 154.7, 149.7, 141.2, 138.3, 137.4, 135.5, 134.5, 131.0, 129.7, 129.3 (3C), 128.1 (2C), 127.2, 124.4, 123.1, 121.5, 111.4, 57.7, 46.9, 46.2, 40.7, 21.9. HRMS (ESI) calcd for $C_{26}H_{21}Cl_2N_6O_2$ 519.1103 (M+H)$^+$, found 519.1104.

(R)-5'-Chloro-3-((S)-1-(4-chlorophenyl)ethyl)-1'-(pyridin-3-ylmethyl)-4,6-dihydrospiro[[1,2,3]triazolo[4,5-b]pyridine-7,3'-indoline]-2',5(3H)-dione (34). Compound 34 (45 mg, 81%) was prepared by a procedure similar to that used to prepare compound 7. The title compound was obtained as a white solid. HPLC purity 99.6% ($t_R$=19.80 min). $^1$H NMR (300 MHz, CDCl$_3$) δ 10.56 (s, 1H), 8.65 (s, 1H), 8.54 (d, J=4.2 Hz, 1H), 7.65 (d, J=8.1 Hz, 1H), 7.32-7.26 (m, 5H), 7.26-7.22 (m, 1H), 7.14 (d, J=2.1 Hz, 1H), 6.73 (d, J=8.4 Hz, 1H), 5.60 (q, J=6.9 Hz, 1H), 5.03 (d, J=15.9 Hz, 1H), 4.90 (d, J=15.9 Hz, 1H), 3.12 (d, J=16.5 Hz, 1H), 3.03 (d, J=16.5 Hz, 1H), 1.97 (d, J=6.9 Hz, 3H). $^{13}$C NMR (75 MHz, CDCl$_3$) δ 176.1, 169.9, 149.6, 148.8, 140.7, 138.1, 135.4, 135.1, 134.7, 131.1, 130.7, 129.8, 129.6, 129.4 (2C), 128.1 (2C), 127.1, 124.7, 124.2, 110.8, 57.8, 46.8, 41.9, 40.7, 21.9. HRMS (ESI) calcd for $C_{26}H_{21}Cl_2N_6O_2$ 519.1103 (M+H)$^+$, found 519.1105.

(R)-5'-Chloro-3-((S)-1-(4-chlorophenyl)ethyl)-1'-(pyridin-4-ylmethyl)-4,6-dihydrospiro[[1,2,3]triazolo[4,5-b]pyridine-7,3'-indoline]-2',5(3H)-dione (35). Compound 35 (13 mg, 43%) was prepared by a procedure similar to that used to prepare compound 7. The title compound was obtained as a light yellow solid. HPLC purity 99.9% ($t_R$=19.49 min). $^1$H NMR (300 MHz, CDCl$_3$) δ 10.42 (s, 1H), 8.59 (d, J=6.0 Hz, 2H), 7.23-7.28 (m, 4H), 7.27-7.21 (m, 3H), 7.17 (d, J=2.1 Hz, 1H), 6.64 (d, J=8.4 Hz, 1H), 5.59 (q, J=6.9 Hz, 1H), 5.09 (d, J=16.8 Hz, 1H), 4.83 (d, J=16.8 Hz, 1H), 3.15 (d, J=16.5 Hz, 1H), 3.06 (d, J=16.8 Hz, 1H), 1.99 (d, J=6.9 Hz, 3H). $^{13}$C NMR (75 MHz, CDCl$_3$) δ 176.0, 169.8, 150.6 (2C), 143.8, 140.6, 138.0, 135.3, 134.8, 131.0, 129.9, 129.7, 129.5 (2C), 128.1 (2C), 127.2, 124.7, 121.9 (2C), 110.8, 57.9, 46.8, 43.2, 40.6, 21.9. HRMS (ESI) calcd for $C_{26}H_{21}Cl_2N_6O_2$ 519.1103 (M+H)$^+$, found 519.1103.

(R)-5'-Chloro-3-((S)-1-(4-chlorophenyl)ethyl)-1'-((6-chloropyridin-3-yl)methyl)-4,6-dihydrospiro[[1,2,3]triazolo[4,5-b]pyridine-7,3'-indoline]-2',5(3H)-dione (36). Compound 36 (23 mg, 71%) was prepared by a procedure similar to that used to prepare compound 7. The title compound was obtained as an off-white solid. HPLC purity 99.5% ($t_R$=19.51 min). $^1$H NMR (300 MHz, CDCl$_3$+CD$_3$OD) δ 8.37 (d, J=2.4 Hz, 1H), 7.62 (dd, J=8.4, 2.4 Hz, 1H), 7.34-7.21 (m, 6H), 7.15 (d, J=2.1 Hz, 1H), 6.78 (d, J=8.4 Hz, 1H), 5.61 (q, J=6.9 Hz, 1H), 4.98 (d, J=15.9 Hz, 1H), 4.84 (d, J=15.9 Hz, 1H), 3.01 (d, J=16.5 Hz, 1H), 2.87 (d, J=16.5 Hz, 1H), 1.96 (d, J=7.2 Hz, 3H). $^{13}$C NMR (75 MHz, CDCl$_3$+CD$_3$OD) δ 176.6, 168.7, 151.3, 148.8, 140.7, 138.6, 138.5, 136.8, 134.7, 131.1, 130.5, 129.9, 129.8, 129.4 (2C), 128.3 (2C), 126.9, 125.3, 125.0, 110.9, 57.7, 47.0, 41.1, 40.6, 21.7. HRMS (ESI) calcd for $C_{26}H_{20}Cl_3N_6O_2$ 553.0713 (M+H)$^+$, found 553.0714.

(R)-5'-Chloro-3-((S)-1-(4-chlorophenyl)ethyl)-1'-((6-methylpyridin-3-yl)methyl)-4,6-dihydrospiro[[1,2,3]triazolo[4,5-b]pyridine-7,3'-indoline]-2',5(3H)-dione (37). To a solution of (R)-5'-chloro-3-((S)-1-(4-chlorophenyl)ethyl)-4,6-dihydrospiro[[1,2,3]triazolo[4,5-b]pyridine-7,3'-indoline]-2',5(3H)-dione (1) (30 mg, 0.070 mmol) in anhydrous THF (10 mL) was added LiHMDS (0.7 mL, 0.70 mmol, 1 M in THF) at 0° C. The resulting mixture was stirred at 0° C. for 15 min. Then 5-(bromomethyl)-2-methylpyridine hydrobromide (28 mg, 0.105 mmol) was added at 0° C. and the resulting mixture was stirred at r.t. for 5 d. The reaction mixture was diluted with EtOAc/MeOH (3:1, 60 mL), washed with water (10 mL) and brine (10 mL), dried over Na$_2$SO$_4$ and concentrated. The residue was purified by preparative TLC developed by 3% MeOH in EtOAc to afford compound 37 (6 mg, 16%) as a light yellow solid. HPLC purity 99.9% ($t_R$=20.16 min). $^1$H NMR (300 MHz, CDCl$_3$) δ 10.30 (br s, 1H), 8.52 (d, J=1.8 Hz, 1H), 7.53 (dd, J=8.1, 2.4 Hz, 1H), 7.33-7.27 (m, 4H), 7.26-7.22 (m, 1H), 7.17-7.10 (m, 2H), 6.74 (d, J=8.4 Hz, 1H), 5.59 (q, J=6.9 Hz, 1H), 4.97 (d, J=15.9 Hz, 1H), 4.87 (d, J=15.9 Hz, 1H), 3.10 (d, J=16.5 Hz, 1H), 3.02 (d, J=16.5 Hz, 1H), 2.53 (s, 3H), 1.99 (d, J=7.2 Hz, 3H). $^{13}$C NMR (75 MHz, CDCl$_3$) δ 176.0, 169.9, 158.7, 148.2, 140.8, 138.0, 135.5, 135.3, 134.8, 131.1, 129.8, 129.5 (3C), 128.1 (2C), 127.6, 127.3, 124.6, 123.9, 110.9, 57.9, 46.8, 41.8, 40.7, 24.3, 21.9. HRMS (ESI) calcd for C$_{27}$H$_{23}$Cl$_2$N$_6$O$_2$ 533.1260 (M+H)$^+$, found 533.1257.

(R)-5'-Chloro-3-((S)-1-(4-chlorophenyl)ethyl)-1'-(2-(methoxymethoxy)ethyl)-4,6-dihydrospiro[[1,2,3]triazolo[4,5-b]pyridine-7,3'-indoline]-2',5(3H)-dione (38). Compound 38 (60 mg, 81%) was prepared by a procedure similar to that used to prepare compound 7. The title compound was obtained as a light yellow solid. HPLC purity 98.9% ($t_R$=18.79 min). $^1$H NMR (300 MHz, CDCl$_3$) δ 10.53 (s, 1H), 7.36-7.27 (m, 5H), 7.11 (d, J=2.1 Hz, 1H), 7.04 (d, J=8.4 Hz, 1H), 5.56 (q, J=6.9 Hz, 1H), 4.57 (s, 2H), 3.96 (t, J=5.4 Hz, 2H), 3.80 (t, J=5.4 Hz, 2H), 3.26 (s, 3H), 3.00 (s, 2H), 1.95 (d, J=6.9 Hz, 3H). $^{13}$C NMR (75 MHz, CDCl$_3$) δ 176.1, 170.0, 142.0, 138.3, 135.5, 134.5, 130.8, 129.6, 129.3 (2C), 129.0, 128.2 (2C), 127.1, 124.3, 111.2, 96.6, 64.9, 57.6, 55.5, 46.6, 41.0, 40.9, 21.8. HRMS (ESI) calcd for C$_{24}$H$_{24}$Cl$_2$N$_5$O$_4$ 516.1205 (M+H)$^+$, found 516.1199.

(R)-5'-Chloro-3-((S)-1-(4-chlorophenyl)ethyl)-1'-(3-methoxypropyl)-4,6-dihydrospiro[[1,2,3]triazolo[4,5-b]pyridine-7,3'-indoline]-2',5(3H)-dione (39). Compound 39 (43 mg, 83%) was prepared by a procedure similar to that used to prepare compound 7. The title compound was obtained as a white solid. HPLC purity 99.5% ($t_R$=18.92 min). 41 NMR (300 MHz, CDCl$_3$) δ 10.60 (s, 1H), 7.37-7.26 (m, 5H), 7.11 (d, J=2.1 Hz, 1H), 6.97 (d, J=8.7 Hz, 1H), 5.56 (q, J=6.9 Hz, 1H), 3.93-3.74 (m, 2H), 3.41 (t, J=5.7 Hz, 2H), 3.30 (s, 3H), 3.08-2.92 (m, 2H), 2.03-1.89 (m, 5H). $^{13}$C NMR (75 MHz, CDCl$_3$) δ 175.9, 170.2, 141.8, 138.3, 135.4, 134.5, 131.0, 129.7, 129.3 (2C), 128.9, 128.2 (2C), 127.2, 124.4, 110.5, 69.5, 58.8, 57.6, 46.7, 40.7, 38.0, 27.7, 21.8. HRMS (ESI) calcd for C$_{24}$H$_{24}$Cl$_2$N$_5$O$_3$ 500.1256 (M+H)$^+$, found 500.1254.

(R)-5'-Chloro-3-((S)-1-(4-chlorophenyl)ethyl)-4-(3-methoxypropyl)-4,6-dihydrospiro[[1,2,3]triazolo[4,5-b]pyridine-7,3'-indoline]-2',5(3H)-dione (40). Compound 40 (5 mg, 10%) was prepared by a procedure same to that used to prepare compound 39. The title compound was obtained a light-yellow solid. HPLC purity 97.5% ($t_R$=18.54 min). $^1$H NMR (300 MHz, CDCl$_3$) δ 8.98 (s, 1H), 7.38-7.26 (m, 5H), 7.14 (d, J=1.8 Hz, 1H), 6.96 (d, J=8.4 Hz, 1H), 5.58 (q, J=6.9 Hz, 1H), 3.83 (t, J=6.9 Hz, 2H), 3.41 (t, J=5.7 Hz, 2H), 3.29 (s, 3H), 3.03 (d, J=16.5 Hz, 1H), 2.93 (d, J=16.5 Hz, 1H), 2.07-1.90 (m, 5H). $^{13}$C NMR (75 MHz, CDCl$_3$) δ 175.4, 169.4, 141.8, 137.4, 135.2, 135.1, 131.2, 129.7 (3C), 128.8, 128.1 (3C), 124.4, 110.4, 69.6, 58.8, 58.1, 46.6, 40.8, 38.1, 27.7, 21.6. HRMS (ESI) calcd for C$_{24}$H$_{24}$Cl$_2$N$_5$O$_3$ 500.1256 (M+H)$^+$, found 500.1247.

(R)-5'-Chloro-3-((S)-1-(4-chlorophenyl)ethyl)-1'-(2,2-diethoxyethyl)-4,6-dihydrospiro[[1,2,3]triazolo[4,5-b]pyridine-7,3'-indoline]-2',5(3H)-dione (41). Compound 41 (10 mg, 24%) was prepared by a procedure similar to that used to prepare compound 7. The title compound was obtained as a yellow solid. HPLC purity 99.6% ($t_R$=19.81 min). $^1$H NMR (300 MHz, CDCl$_3$) δ 10.14 (s, 1H), 7.36-7.29 (m, 5H), 7.14-7.10 (m, 2H), 5.58 (q, J=6.9 Hz, 1H), 4.69 (t, J=5.4 Hz, 1H), 3.88-3.82 (m, 2H), 3.81-3.69 (m, 2H), 3.59-3.46 (m, 2H), 3.07-2.93 (m, 2H), 1.99 (d, J=6.9 Hz, 3H), 1.21-1.10 (m, 6H). $^{13}$C NMR (75 MHz, CDCl$_3$) δ 176.1, 170.0, 142.1, 138.0, 135.3, 134.8, 130.6, 129.5 (3C), 128.9, 128.2 (2C), 127.4, 124.1, 112.0, 100.7, 64.3, 64.0, 57.9, 46.6, 44.3, 41.0, 21.79, 15.5, 15.4. HRMS (ESI) calcd for C$_{26}$H$_{28}$Cl$_2$N$_5$O$_4$ 544.1518 (M+H)$^+$, found 544.1515.

(R)-5'-Chloro-3-((S)-1-(4-chlorophenyl)ethyl)-1'-(2-hydroxyethyl)-4,6-dihydrospiro[[1,2,3]triazolo[4,5-b]pyridine-7,3'-indoline]-2',5(3H)-dione (42). The intermediate (3'R)-5'-chloro-3-((S)-1-(4-chlorophenyl)ethyl)-1'-(2-((tetrahydro-2H-pyran-2-yl)oxy)ethyl)-4,6-dihydrospiro[[1,2,3]triazolo[4,5-b]pyridine-7,3'-indoline]-2',5(3H)-dione 51 (46 mg, 74%) was prepared by a procedure similar to that used to prepare compound 7.

To a solution of compound 51 (125 mg, 0.23 mmol) in 10 mL of EtOH was added TsOH (8 mg, 0.045 mmol). The resulting mixture was stirred at r.t. for 24 h. Then the mixture was concentrated and purified by preparative TLC developed by 4% MeOH in DCM to give compound 42 (90 mg, 84%) as a white solid. HPLC purity 99.3% ($t_R$=17.56 min). $^1$H NMR (300 MHz, CDCl$_3$) δ 10.49 (s, 1H), 7.36-7.23 (m, 5H), 7.04 (d, J=1.8 Hz, 1H), 7.00 (d, J=8.4 Hz, 1H), 5.56 (q, J=6.9 Hz, 1H), 4.05-3.54 (m, 5H), 3.03 (d, J=16.5 Hz, 1H), 2.93 (d, J=16.5 Hz, 1H), 1.89 (d, J=6.9 Hz, 3H). $^{13}$C NMR (75 MHz, CDCl$_3$) δ 176.5, 169.8, 142.0, 138.2, 135.7, 134.7, 131.0, 129.7, 129.4 (2C), 129.0, 128.1 (2C), 127.2, 124.2, 111.2, 59.7, 57.8, 46.7, 43.7, 40.5, 21.8. HRMS (ESI) calcd for C$_{22}$H$_{20}$Cl$_2$N$_5$O$_3$ 472.0943 (M+H)$^+$, found 472.0942.

Methyl 2-((R)-5'-chloro-3-((S)-1-(4-chlorophenyl)ethyl)-2',5-dioxo-3,4,5,6-tetrahydrospiro[[1,2,3]triazolo[4,5-b]pyridine-7,3'-indolin]-1'-yl)acetate (43). Compound 43 (47 mg, 79%) was prepared by a procedure similar to that used to prepare compound 7. The title compound was obtained as a white solid. HPLC purity 99.6% ($t_R$=18.61 min). $^1$H NMR (300 MHz, CDCl$_3$) δ 10.46 (s, 1H), 7.41-7.30 (m, 5H), 7.19 (d, J=2.1 Hz, 1H), 6.80 (d, J=8.4 Hz, 1H), 5.60 (q, J=6.9 Hz, 1H), 4.73 (d, J=17.7 Hz, 1H), 4.33 (d, J=17.4 Hz, 1H), 3.80 (s, 3H), 3.16-3.01 (m, 2H), 2.00 (d, J=6.9 Hz, 3H). $^{13}$C NMR (75 MHz, CDCl$_3$) δ 176.0, 170.0, 167.6, 141.0, 138.3, 135.6, 134.6, 130.6, 129.8, 129.5, 129.3 (2C), 128.2 (2C), 126.8, 124.7, 110.2, 57.7, 53.0, 46.7, 41.7, 41.0, 21.8. HRMS (ESI) calcd for C$_{23}$H$_{20}$Cl$_2$N$_5$O$_4$ 500.0892 (M+H)$^+$, found 500.0886.

Methyl 2-((R)-5'-chloro-3-((S)-1-(4-chlorophenyl)ethyl)-2',5-dioxo-5,6-dihydrospiro[[1,2,3]triazolo[4,5-b]pyridine-7,3'-indolin]-4(3H)-yl)acetate (44). Compound 44 (3 mg, 5%) was prepared by a procedure same to that used to prepare compound 43. The title compound was obtained as a white solid. HPLC purity 95.0% ($t_R$=18.20 min). $^1$H NMR (300 MHz, CDCl$_3$) δ 9.27 (s, 1H), 7.38-7.28 (m, 5H), 7.19 (d, J=1.8 Hz, 1H), 6.76 (d, J=8.4 Hz, 1H), 5.59 (q, J=6.9 Hz, 1H), 4.71 (d, J=17.7 Hz, 1H), 4.27 (d, J=17.4 Hz, 1H), 3.78 (s, 3H), 3.09 (d, J=16.5 Hz, 1H), 3.00 (d, J=16.5 Hz, 1H), 2.01 (d, J=7.2 Hz, 3H). $^{13}$C NMR (75 MHz, CDCl$_3$) δ 175.5, 169.4, 167.6, 140.9, 137.4, 135.3, 135.0, 130.8, 129.8, 129.7 (2C), 129.5, 128.1 (2C), 127.5, 124.7, 110.2, 58.2, 53.0, 46.6, 41.7, 40.9, 21.6. HRMS (ESI) calcd for C$_{23}$H$_{20}$Cl$_2$N$_5$O$_4$ 500.0892 (M+H)$^+$, found 500.0881.

2-((R)-5'-Chloro-3-((S)-1-(4-chlorophenyl)ethyl)-2',5-dioxo-3,4,5,6-tetrahydrospiro[[1,2,3]triazolo[4,5-b]pyridine-7,3'-indolin]-1'-yl)acetic acid (45). To a solution of compound 43 (124 mg, 0.25 mmol) in THF (6 mL) was added NaOH (50 mg, 1.24 mmol, in 2 mL of H$_2$O). The resulting mixture was stirred at r.t for 1 h. Then the pH value of the mixture was adjusted to 3~4 with 1 M HCl (aq.). The resulting mixture was extracted with EtOAc/MeOH (3:1, 2×60 mL), washed with water (2×15 mL) and concentrated in vacuo to give compound 45 (100 mg, 83%) as a white solid. HPLC purity 98.4% ($t_R$=11.91 min). $^1$H NMR (300 MHz, CD$_3$OD) δ 7.43-7.30 (m, 6H), 7.03 (d, J=8.4 Hz, 1H), 5.74 (q, J=6.9 Hz, 1H), 4.57 (d, J=18.0 Hz, 1H), 4.46 (d, J=18.0 Hz, 1H), 3.31 (d, J=16.2 Hz, 1H), 2.77 (d, J=16.5 Hz, 1H), 1.97 (d, J=6.9 Hz, 3H). $^{13}$C NMR (75 MHz, CD$_3$OD) δ 177.9, 170.4, 170.1, 143.1, 140.0, 138.5, 135.3, 131.9, 130.5, 130.1, 130.1 (2C), 129.3 (2C), 128.1, 125.8, 111.8, 58.5, 47.9, 42.2, 41.3, 21.8. HRMS (ESI) calcd for C$_{22}$H$_{18}$Cl$_2$N$_5$O$_4$ 486.0736 (M+H)$^+$, found 486.0728.

(R)-5'-Chloro-3-((S)-1-(4-chlorophenyl)ethyl)-1'-(2-fluoroethyl)-4,6-dihydrospiro[[1,2,3]triazolo[4,5-b]pyridine-7,3'-indoline]-2',5(3H)-dione (46). Compound 46 (20 mg, 41%) was prepared by a procedure similar to that used to prepare compound 7. The title compound was obtained as a light yellow solid. HPLC purity 99.6% ($t_R$=18.70 min). $^1$H NMR (300 MHz, CDCl$_3$) δ 10.50 (s, 1H), 7.37-7.28 (m, 5H), 7.14 (d, J=2.1 Hz, 1H), 7.00 (d, J=8.4 Hz, 1H), 5.58 (q, J=6.9 Hz, 1H), 4.69 (dt, J=46.8, 4.8 Hz, 2H), 4.19-3.93 (m, 2H), 3.03 (s, 2H), 1.96 (d, J=7.0 Hz, 3H). $^{13}$C NMR (75 MHz, CDCl$_3$) δ 176.1, 170.1, 141.6, 138.2, 135.4, 134.7, 130.7, 129.8, 129.4 (2C), 129.3, 128.2 (2C), 127.1, 124.5, 111.0, 110.9, 81.7 (d, J=170.9 Hz), 57.8, 46.7, 41.5 (d, J=21.0 Hz), 41.0, 21.9. HRMS (ESI) calcd for C$_{22}$H$_{19}$Cl$_2$FN$_5$O$_2$ 474.0900 (M+H)$^+$, found 474.0907.

(R)-1'-(3-Bromopropyl)-5'-chloro-3-((S)-1-(4-chlorophenyl)ethyl)-4,6-dihydrospiro[[1,2,3]triazolo[4,5-b]pyridine-7,3'-indoline]-2',5(3H)-dione (47). Compound 47 (32 mg, 50%) was prepared by a procedure similar to that used to prepare compound 7. The title compound was obtained as a white solid. HPLC purity 96.2% ($t_R$=19.78 min). 41 NMR (300 MHz, CDCl$_3$) δ 10.38 (s, 1H), 7.41-7.29 (m, 5H), 7.14 (t, J=2.1 Hz, 1H), 7.00 (d, J=8.7 Hz, 1H), 5.58 (q, J=6.9 Hz, 1H), 4.03-3.78 (m, 2H), 3.50-3.40 (m, 2H), 3.10-2.95 (m, 2H), 2.35-2.22 (m, 2H), 1.98 (d, J=6.9 Hz, 3H). $^{13}$C NMR (75 MHz, CDCl$_3$) δ 175.9, 170.1, 141.4, 138.1, 135.3, 134.7, 131.0, 129.9, 129.4 (2C), 129.2, 128.2 (2C), 127.3, 124.6, 110.4, 57.8, 46.6, 40.6, 39.3, 30.5, 30.2, 21.9. HRMS (ESI) calcd for C$_{23}$H$_{21}$BrCl$_2$N$_5$O$_2$ 548.0256 (M+H)$^+$, found 548.0256.

(R)-5'-Chloro-1'-(4-chlorobutyl)-3-((S)-1-(4-chlorophenyl)ethyl)-4,6-dihydrospiro[[1,2,3]triazolo[4,5-b]pyridine-7,3'-indoline]-2',5(3H)-dione (48). Compound 48 (64 mg, 87%) was prepared by a procedure similar to that used to prepare compound 7. The title compound was obtained as a white solid. HPLC purity 99.4% ($t_R$=19.88 min). 41 NMR (300 MHz, CDCl$_3$) δ 10.64 (s, 1H), 7.38-7.27 (m, 5H), 7.12 (d, J=1.8 Hz, 1H), 6.91 (d, J=8.4 Hz, 1H), 5.58 (q, J=6.9 Hz, 1H), 3.92-3.68 (m, 2H), 3.66-3.50 (m, 2H), 3.09-2.95 (m, 2H), 2.01-1.78 (m, 7H). $^{13}$C NMR (75 MHz, CDCl$_3$) δ 175.9, 170.3, 141.3, 138.2, 135.3, 134.6, 131.1, 129.8, 129.3 (2C), 129.1, 128.2 (2C), 127.2, 124.6, 110.4, 57.7, 46.7, 44.4, 40.8, 39.8, 29.4, 24.6, 21.9. HRMS (ESI) calcd for C$_{24}$H$_{23}$Cl$_3$N$_5$O$_2$ 518.0917 (M+H)$^+$, found 518.0921.

(R)-1'-(6-Bromohexyl)-5'-chloro-3-((S)-1-(4-chlorophenyl)ethyl)-4,6-dihydrospiro[[1,2,3]triazolo[4,5-b]pyridine-7,3'-indoline]-2',5(3H)-dione (49). Compound 49 (17 mg, 47%) was prepared by a procedure similar to that used to prepare compound 7. The title compound was obtained as a light yellow solid. HPLC purity 99.6% ($t_R$=20.68 min). $^1$H NMR (300 MHz, CDCl$_3$) δ 10.17 (s, 1H), 7.38-7.27 (m, 5H), 7.14 (d, J=2.1 Hz, 1H), 6.89 (d, J=8.4 Hz, 1H), 5.57 (q, J=6.9 Hz, 1H), 3.87-3.62 (m, 2H), 3.39 (t, J=6.9 Hz, 2H), 3.00 (s, 2H), 1.98 (d, J=6.9 Hz, 3H), 1.91-1.67 (m, 4H), 1.54-1.33 (m, 4H). $^{13}$C NMR (75 MHz, CDCl$_3$) δ 175.8, 170.0, 141.6, 138.1, 135.3, 134.8, 131.1, 129.7, 129.5 (2C), 129.0, 128.2 (2C), 127.4, 124.6, 110.4, 57.8, 46.7, 40.8, 40.5, 33.8, 32.6, 27.8, 27.2, 26.0, 21.8. HRMS (ESI) calcd for C$_{26}$H$_{27}$BrCl$_2$N$_5$O$_2$ 590.0725 (M+H)$^+$, found 590.0723.

(R)-1'-(8-bromooctyl)-5'-chloro-3-((S)-1-(4-chlorophenyl)ethyl)-4,6-dihydrospiro[[1,2,3]triazolo[4,5-b]pyridine-7,3'-indoline]-2',5(3H)-dione (50). Compound 50 (17 mg, 47%) was prepared by a procedure similar to that used to prepare compound 7. The title compound was obtained as a light yellow solid. HPLC purity 97.2% ($t_R$=21.82 min). $^1$H NMR (300 MHz, CDCl$_3$) δ 10.18 (s, 1H), 7.37-7.27 (m, 5H), 7.13 (d, J=2.1 Hz, 1H), 6.88 (d, J=8.4 Hz, 1H), 5.56 (q, J=6.9 Hz, 1H), 3.85-3.63 (m, 2H), 3.39 (t, J=6.9 Hz, 2H), 3.00 (s, 2H), 1.97 (d, J=6.9 Hz, 3H), 1.88-1.77 (m, 2H), 1.75-1.67 (m, 2H), 1.45-1.26 (m, 8H). $^{13}$C NMR (75 MHz, CDCl$_3$) δ 175.8, 170.0, 141.7, 138.1, 135.3, 134.7, 131.1, 129.7, 129.5 (2C), 129.0, 128.2 (2C), 127.4, 124.6, 110.4, 57.8, 46.7, 40.9, 40.7, 34.1, 32.8, 29.1, 28.7, 28.1, 27.3, 26.7, 21.8. HRMS (ESI) calcd for C$_{28}$H$_{31}$BrCl$_2$N$_5$O$_2$ 618.1038 (M+H)$^+$, found 618.1036.

(R)-5'-chloro-3-((S)-1-(4-chlorophenyl)ethyl)-1'-(2-morpholinoethyl)-4,6-dihydrospiro[[1,2,3]triazolo[4,5-b]pyridine-7,3'-indoline]-2',5(3H)-dione (55). To a solution of compound 42 (90 mg, 0.19 mmol) and CBr$_4$ (190 mg, 0.57 mmol) in 8 mL of DCM was added PPh$_3$ (150 mg, 0.57 mmol) at 0° C. After addition, the resulting mixture was stirred at r.t for 24 h. The mixture was concentrated and purified by column chromatography (Hex/EtOAc=1/1 to 1/2) to give (R)-1'-(2-bromoethyl)-5'-chloro-3-((S)-1-(4-chlorophenyl)ethyl)-4,6-dihydrospiro[[1,2,3]triazolo[4,5-b]pyridine-7,3'-indoline]-2',5(3H)-dione 52 (90 mg, 97%) as a white solid. $^1$H NMR (300 MHz, CDCl$_3$) δ 10.63 (s, 1H), 7.39-7.27 (m, 5H), 7.13 (d, J=1.8 Hz, 1H), 6.96 (d, J=8.4 Hz, 1H), 5.61 (q, J=6.9 Hz, 1H), 4.27-4.03 (m, 2H), 3.70-3.56 (m, 2H), 3.07 (d, J=16.8 Hz, 1H), 3.00 (d, J=16.8 Hz, 1H), 1.97 (d, J=6.9 Hz, 3H).

To a solution of compound 52 (21 mg, 0.039 mmol) and K$_2$CO$_3$ (6 mg, 0.039 mmol) in 4 mL of MeCN was added morpholine (17 mg, 0.19 mmol). The resulting mixture was stirred at 80° C. for 24 h. Then the solids were filtered out. The resulting mixture was concentrated and purified by preparative TLC developed by 5% MeOH in DCM to give compound 55 (19 mg, 90%) as an off-white solid. HPLC purity 95.6% ($t_R$=17.15 min). $^1$H NMR (300 MHz, CDCl$_3$) δ 7.39-7.26 (m, 5H), 7.16 (d, J=2.1 Hz, 1H), 6.89 (t, J=8.4 Hz, 1H), 5.60 (q, J=6.9 Hz, 1H), 4.03-3.91 (m, 1H), 3.80-3.59 (m, 5H), 3.08-2.97 (m, 2H), 2.76-2.50 (m, 4H), 2.47-2.36 (m, 2H), 1.98 (d, J=6.9 Hz, 3H). $^{13}$C NMR (75 MHz, CDCl$_3$) δ 176.0, 170.4, 141.5, 138.3, 135.5, 134.6, 130.9, 129.6, 129.3 (2C), 128.9, 128.2 (2C), 127.1, 124.7, 110.4, 67.1 (2C), 57.7, 55.0, 53.8 (2C), 46.7, 41.5, 37.7, 21.8. HRMS (ESI) calcd for C$_{26}$H$_{27}$Cl$_2$N$_6$O$_3$ 541.1522 (M+H)$^+$, found 541.1519.

(R)-5'-Chloro-3-((S)-1-(4-chlorophenyl)ethyl)-1'-(2-(piperidin-1-yl)ethyl)-4,6-dihydrospiro[[1,2,3]triazolo[4,5-b]pyridine-7,3'-indoline]-2',5(3H)-dione (56). Compound 56 (13 mg, 86%) was prepared by a procedure similar to that used to prepare compound 55. The title compound was obtained as a yellow solid. HPLC purity 99.0% ($t_R$=17.78 min). $^1$H NMR (300 MHz, CDCl$_3$) δ 7.37-7.27 (m, 5H), 7.13 (d, J=1.8 Hz, 1H), 6.97 (d, J=8.4 Hz, 1H), 5.60 (q, J=6.9 Hz, 1H), 4.05-3.90 (m, 1H), 3.89-3.74 (m, 1H), 3.07-2.93 (m, 2H), 2.76-2.35 (m, 6H), 1.97 (d, J=6.9 Hz, 3H), 1.65-1.51 (m, 4H), 1.48-1.37 (m, 2H). $^{13}$C NMR (75 MHz, CDCl$_3$) δ 175.9, 170.1, 141.7, 138.2, 135.5, 134.7, 131.0, 129.7, 129.4 (2C), 128.9, 128.2 (2C), 127.3, 124.6, 110.7, 57.7, 55.4, 54.9

(2C), 46.7 (2C), 41.2, 38.3, 25.9, 24.2, 21.8. HRMS (ESI) calcd for $C_{27}H_{29}Cl_2N_6O_2$ 539.1729 (M+H)$^+$, found 539.1729.

(R)-5'-Chloro-3-((S)-1-(4-chlorophenyl)ethyl)-1'-(2-(dimethylamino)ethyl)-4,6-dihydrospiro[[1,2,3]triazolo[4,5-b]pyridine-7,3'-indoline]-2',5(3H)-dione (57). Compound 57 (16 mg, 85%) was prepared by a procedure similar to that used to prepare compound 55. The title compound was obtained as a white solid. HPLC purity 98.2% ($t_R$=17.07 min). $^1$H NMR (300 MHz, CDCl$_3$) δ 7.39-7.27 (m, 5H), 7.13 (d, J=2.1 Hz, 1H), 6.94 (d, J=8.4 Hz, 1H), 5.58 (q, J=6.9 Hz, 1H), 3.94-3.77 (m, 2H), 3.04-2.96 (m, 2H), 2.71-2.51 (m, 2H), 2.32 (s, 6H), 1.96 (d, J=6.9 Hz, 3H). $^{13}$C NMR (75 MHz, CDCl$_3$) δ 175.9, 170.1, 141.6, 138.2, 135.5, 134.6, 131.0, 129.7, 129.4 (2C), 129.0, 128.2 (2C), 127.2, 124.6, 110.5, 57.8, 56.0, 46.7, 45.7 (2C), 41.0, 39.1, 21.8. HRMS (ESI) calcd for $C_{24}H_{25}Cl_2N_6O_2$ 499.1416 (M+H)$^+$, found 499.1416.

(R)-5'-Chloro-3-((S)-1-(4-chlorophenyl)ethyl)-1'-(2-(pyrrolidin-1-yl)ethyl)-4,6-dihydrospiro[[1,2,3]triazolo[4,5-b]pyridine-7,3'-indoline]-2',5(3H)-dione (58). Compound 58 (12 mg, 87%) was prepared by a procedure similar to that used to prepare compound 55. The title compound was obtained as a yellow solid. HPLC purity 99.5% ($t_R$=17.50 min). $^1$H NMR (300 MHz, CDCl$_3$) δ 7.38-7.27 (m, 5H), 7.14 (d, J=2.1 Hz, 1H), 6.94 (d, J=8.4 Hz, 1H), 5.57 (q, J=6.9 Hz, 1H), 4.00-3.78 (m, 2H), 2.99 (s, 2H), 2.90-2.79 (m, 1H), 2.74-2.48 (m, 5H), 1.97 (d, J=6.9 Hz, 3H), 1.84-1.72 (m, 4H). $^{13}$C NMR (75 MHz, CDCl$_3$) δ 175.9, 170.1, 141.7, 138.2, 135.5, 134.7, 131.0, 129.7, 129.4 (2C), 129.0, 128.2 (2C), 127.3, 124.6, 110.5, 57.8, 54.4 (2C), 52.6, 46.7, 41.1, 40.0, 23.7 (2C), 21.8. HRMS (ESI) calcd for $C_{26}H_{27}Cl_2N_6O_2$ 525.1573 (M+H)$^+$, found 5251574.

(R)-5'-Chloro-3-((S)-1-(4-chlorophenyl)ethyl)-1'-(2-(4-methylpiperazin-1-yl)ethyl)-4,6-dihydrospiro[[1,2,3]triazolo[4,5-b]pyridine-7,3'-indoline]-2',5(3H)-dione (59). Compound 59 (12 mg, 81%) was prepared by a procedure similar to that used to prepare compound 55. The title compound was obtained as a yellow solid. HPLC purity 98.9% ($t_R$=17.33 min). $^1$H NMR (300 MHz, CDCl$_3$) δ 7.47-7.27 (m, 5H), 7.15 (d, J=2.1 Hz, 1H), 6.92 (d, J=8.4 Hz, 1H), 5.90 (br s, 1H), 5.58 (q, J=6.9 Hz, 1H), 3.98-3.72 (m, 2H), 3.00 (s, 2H), 2.81-2.30 (m, 10H), 2.27 (s, 3H), 1.99 (d, J=6.9 Hz, 3H). $^{13}$C NMR (75 MHz, CDCl$_3$) δ 175.9, 170.0, 141.6, 138.1, 135.5, 134.7, 130.9, 129.7, 129.5 (2C), 128.9, 128.2 (2C), 127.3, 124.7, 110.5, 57.8, 55.2 (2C), 54.6, 53.3 (2C), 46.7, 46.1, 41.2, 38.2, 21.8. HRMS (ESI) calcd for $C_{27}H_{30}Cl_2N_7O_2$ 554.1838 (M+H)$^+$, found 554.1859.

(R)-5'-Chloro-3-((S)-1-(4-chlorophenyl)ethyl)-1'-(2-(methyl(2-(methylsulfonyl)ethyl)amino)ethyl)-4,6-dihydrospiro[[1,2,3]triazolo[4,5-b]pyridine-7,3'-indoline]-2',5(3H)-dione (60). Compound 60 (5 mg, 30%) was prepared by a procedure similar to that used to prepare compound 55. The title compound was obtained as a white solid. HPLC purity 95.0% ($t_R$=17.02 min). $^1$H NMR (300 MHz, CDCl$_3$) δ 9.51 (s, 1H), 7.40-7.26 (m, 5H), 7.15 (d, J=2.1 Hz, 1H), 6.90 (d, J=8.4 Hz, 1H), 5.57 (q, J=6.9 Hz, 1H), 3.91-3.74 (m, 2H), 3.08 (t, J=6.6 Hz, 2H), 3.00-2.85 (m, 7H), 2.81-2.68 (m, 2H), 2.33 (s, 3H), 1.99 (d, J=6.9 Hz, 3H). $^{13}$C NMR (75 MHz, CDCl$_3$) δ 176.0, 169.4, 141.5, 137.8, 135.5, 134.9, 130.9, 129.8, 129.6 (2C), 129.2, 128.1 (2C), 127.5, 124.8, 110.3, 58.0, 54.4, 52.9, 51.0, 46.7, 42.2, 42.2, 40.9, 38.7, 21.6. HRMS (ESI) calcd for $C_{26}H_{29}Cl_2N_6O_4S$ 591.1348 (M+H)$^+$, found 591.1345.

(R)-1'-(2-(Azetidin-1-yl)ethyl)-5'-chloro-3-((S)-1-(4-chlorophenyl)ethyl)-4,6-dihydrospiro[[1,2,3]triazolo[4,5-b]pyridine-7,3'-indoline]-2',5(3H)-dione (61). Compound 61 (12 mg, 78%) was prepared by a procedure similar to that used to prepare compound 55. The title compound was obtained as a white solid. HPLC purity 95.1% ($t_R$=17.28 min). $^1$H NMR (300 MHz, CDCl$_3$) δ 7.38-7.29 (m, 5H), 7.13 (d, J=2.1 Hz, 1H), 6.94 (d, J=8.4 Hz, 1H), 5.58 (q, J=6.9 Hz, 1H), 3.71 (t, J=6.9 Hz, 2H), 3.30-3.18 (m, 4H), 3.06-2.92 (m, 2H), 2.80-2.62 (m, 2H), 2.06 (p, J=7.2 Hz, 2H), 1.96 (d, J=7.2 Hz, 3H). $^{13}$C NMR (75 MHz, CDCl$_3$) δ 175.9, 169.9, 141.7, 138.1, 135.6, 134.7, 131.0, 129.7, 129.5 (2C), 129.0, 128.2 (2C), 127.3, 124.6, 110.5, 57.8, 56.2, 55.8 (2C), 46.7, 41.0, 39.5, 21.8, 18.0. HRMS (ESI) calcd for $C_{25}H_{27}Cl_2N_6O_2$ 511.1416 (M+H)$^+$, found 511.1418.

(R)-5'-chloro-3-((S)-1-(4-chlorophenyl)ethyl)-1'-(2-(methylamino)ethyl)-4,6-dihydrospiro[[1,2,3]triazolo[4,5-b]pyridine-7,3'-indoline]-2',5(3H)-dione (62). Compound 62 (14 mg, 77%) was prepared by a procedure similar to that used to prepare compound 55. The title compound was obtained as a yellow solid. HPLC purity 96.5% ($t_R$=16.79 min). $^1$H NMR (300 MHz, CDCl$_3$) δ 7.38-7.27 (m, 5H), 7.10 (d, J=1.8 Hz, 1H), 6.98 (d, J=8.4 Hz, 1H), 5.66 (q, J=6.9 Hz, 1H), 4.92 (br s, 2H), 4.04-3.79 (m, 2H), 3.09-2.86 (m, 4H), 2.45 (s, 3H), 1.94 (d, J=6.9 Hz, 3H). $^{13}$C NMR (75 MHz, CDCl$_3$) δ 176.3, 169.9, 141.4, 138.3, 135.8, 134.6, 131.2, 129.8, 129.4 (2C), 129.2, 128.1 (2C), 127.3, 124.5, 110.6, 57.8, 48.6, 46.7, 40.6, 40.3, 35.9, 21.9. HRMS (ESI) calcd for $C_{23}H_{23}Cl_2N_6O_2$ 485.1260 (M+H)$^+$, found 485.1259.

(R)-5'-Chloro-3-((S)-1-(4-chlorophenyl)ethyl)-1'-(3-(dimethylamino)propyl)-4,6-dihydrospiro[[1,2,3]triazolo[4,5-b]pyridine-7,3'-indoline]-2',5(3H)-dione (63). Compound 63 (20 mg, 51%) was prepared by a procedure similar to that used to prepare compound 55. The title compound was obtained as an off-white solid. HPLC purity 98.7% ($t_R$=17.10 min). $^1$H NMR (300 MHz, CDCl$_3$) δ 7.38-7.27 (m, 5H), 7.12 (d, J=2.1 Hz, 1H), 6.99 (d, J=8.4 Hz, 1H), 6.15 (br s, 1H), 5.60 (q, J=6.9 Hz, 1H), 3.88-3.73 (m, 2H), 3.05-2.91 (m, 2H), 2.37 (t, J=6.9 Hz, 2H), 2.23 (s, 6H), 1.96 (d, J=7.0 Hz, 3H), 1.93-1.82 (m, 2H). $^{13}$C NMR (75 MHz, CDCl$_3$) δ 175.9, 170.1, 141.8, 138.2, 135.5, 134.6, 131.1, 129.7, 129.4 (2C), 128.9, 128.2 (2C), 127.4, 124.5, 110.5, 57.7, 56.6, 46.7, 45.4 (2C), 40.8, 38.9, 25.5, 21.8. HRMS (ESI) calcd for $C_{25}H_{27}Cl_2N_6O_2$ 513.1573 (M+H)$^+$, found 513.1557.

(R)-5'-Chloro-3-((S)-1-(4-chlorophenyl)ethyl)-1'-(3-(piperidin-1-yl)propyl)-4,6-dihydrospiro[[1,2,3]triazolo[4,5-b]pyridine-7,3'-indoline]-2',5(3H)-dione (64). Compound 64 (22 mg, 57%) was prepared by a procedure similar to that used to prepare compound 55. The title compound was obtained as an off-white solid. HPLC purity 99.8% ($t_R$=17.79 min). $^1$H NMR (300 MHz, CDCl$_3$) δ 7.37-7.27 (m, 5H), 7.11 (d, J=2.1 Hz, 1H), 7.03 (d, J=8.4 Hz, 1H), 6.08 (br s, 1H), 5.58 (q, J=6.9 Hz, 1H), 3.90-3.66 (m, 2H), 2.99 (s, 2H), 2.46-2.21 (m, 6H), 2.07-1.79 (m, 5H), 1.67-1.51 (m, 4H), 1.49-1.37 (m, 2H). $^{13}$C NMR (75 MHz, CDCl$_3$) δ 175.8, 170.2, 141.9, 138.2, 135.5, 134.6, 131.0, 129.6, 129.4 (2C), 128.9, 128.2 (2C), 127.3, 124.4, 110.8, 57.7, 55.8, 54.6 (2C), 46.7, 40.9, 38.9, 26.1 (2C), 24.9, 24.5, 21.8. HRMS (ESI) calcd for $C_{28}H_{31}Cl_2N_6O_2$ 553.1886 (M+H)$^+$, found 553.1884.

(R)-5'-Chloro-3-((S)-1-(4-chlorophenyl)ethyl)-1'-(3-morpholinopropyl)-4,6-dihydrospiro[[1,2,3]triazolo[4,5-b]pyridine-7,3'-indoline]-2',5(3H)-dione (65). Compound 65 (25 mg, 65%) was prepared by a procedure similar to that used to prepare compound 55. The title compound was obtained as a yellow solid. HPLC purity 99.7% ($t_R$=17.09 min). $^1$H NMR (300 MHz, CDCl$_3$) δ 7.37-7.28 (m, 5H), 7.12 (d, J=1.8 Hz, 1H), 6.99 (d, J=8.4 Hz, 1H), 5.57 (q, J=6.9 Hz, 1H), 3.93-3.63 (m, 6H), 3.00 (s, 2H), 2.48-2.32 (m, 6H), 2.03-

1.81 (m, 5H). $^{13}$C NMR (75 MHz, CDCl$_3$) δ 175.8, 170.2, 141.8, 138.2, 135.3, 134.7, 131.0, 129.6, 129.4 (2C), 129.0, 128.2 (2C), 127.3, 124.5, 110.5, 67.1 (2C), 57.8, 55.5, 53.7 (2C), 46.7, 40.8, 38.7, 24.4, 21.9. FIRMS (ESI) calcd for C$_{27}$H$_{29}$Cl$_2$N$_6$O$_3$ 555.1678 (M+H)$^+$, found 555.1676.

(R)-5'-Chloro-3-((S)-1-(4-chlorophenyl)ethyl)-1'-(4-(dimethylamino)butyl)-4,6-dihydrospiro[[1,2,3]triazolo[4,5-b]pyridine-7,3'-indoline]-2',5(3H)-dione (66). Compound 66 (20 mg, 98%) was prepared by a procedure similar to that used to prepare compound 55. The title compound was obtained as an off-white solid. HPLC purity 99.5% (t$_R$=17.32 min). $^1$H NMR (300 MHz, CDCl$_3$) δ 7.37-7.27 (m, 5H), 7.12 (d, J=2.1 Hz, 1H), 6.91 (d, J=8.4 Hz, 1H), 6.76 (br s, 1H), 5.58 (q, J=6.9 Hz, 1H), 3.87-3.64 (m, 2H), 2.98 (s, 2H), 2.32 (t, J=7.2 Hz, 2H), 2.21 (s, 6H), 1.97 (d, J=6.9 Hz, 3H), 1.82-1.67 (m, 2H), 1.61-1.47 (m, 2H). $^{13}$C NMR (75 MHz, CDCl$_3$) δ 175.8, 170.2, 141.6, 138.2, 135.6, 134.6, 131.1, 129.7, 129.4 (2C), 129.0, 128.2 (2C), 127.3, 124.6, 110.5, 59.0, 57.7, 46.7, 45.4 (2C), 40.9, 40.5, 25.2, 24.7, 21.8. HRMS (ESI) calcd for C$_{26}$H$_{29}$Cl$_2$N$_6$O$_2$ 527.1729 (M+H)$^+$, found 527.1729.

(R)-5'-Chloro-3-((S)-1-(4-chlorophenyl)ethyl)-1'-(4-(piperidin-1-yl)butyl)-4,6-dihydrospiro[[1,2,3]triazolo[4,5-b]pyridine-7,3'-indoline]-2',5(3H)-dione (67). Compound 67 (19 mg, 96%) was prepared by a procedure similar to that used to prepare compound 55. The title compound was obtained as a yellow solid. HPLC purity 99.4% (t$_R$=18.13 min). $^1$H NMR (300 MHz, CDCl$_3$) δ 7.30 (s, 5H), 7.12 (d, J=2.1 Hz, 1H), 6.94 (d, J=8.4 Hz, 1H), 6.81 (br s, 1H), 5.58 (q, J=6.9 Hz, 1H), 3.82-3.65 (m, 2H), 3.05-2.91 (m, 2H), 2.47-2.24 (m, 6H), 1.96 (d, J=6.9 Hz, 3H), 1.80-1.66 (m, 2H), 1.64-1.50 (m, 6H), 1.43 (d, J=4.9 Hz, 2H). $^{13}$C NMR (75 MHz, CDCl$_3$) δ 175.8, 170.2, 141.6, 138.3, 135.8, 134.6, 131.2, 129.6, 129.4 (2C), 128.9, 128.2 (2C), 127.3, 124.5, 110.5, 58.5, 57.7, 54.6 (2C), 46.8, 40.8, 40.5, 26.0 (2C), 25.3, 24.5, 23.9, 21.8. HRMS (ESI) calcd for C$_{29}$H$_{33}$Cl$_2$N$_6$O$_2$ 567.2042 (M+H)$^+$, found 567.2043.

(R)-5'-Chloro-3-((S)-1-(4-chlorophenyl)ethyl)-1'-(6-(dimethylamino)hexyl)-4,6-dihydrospiro[[1,2,3]triazolo[4,5-b]pyridine-7,3'-indoline]-2',5(3H)-dione (68). Compound 68 (9 mg, 73%) was prepared by a procedure similar to that used to prepare compound 55. The title compound was obtained as a white solid. HPLC purity 99.3% (t$_R$=17.81 min). $^1$H NMR (300 MHz, CDCl$_3$) δ 7.38-7.28 (m, 5H), 7.12 (d, J=2.1 Hz, 1H), 6.88 (d, J=8.4 Hz, 1H), 5.56 (q, J=6.9 Hz, 1H), 3.81-3.61 (m, 2H), 3.01 (d, J=16.5 Hz, 1H), 2.95 (d, J=16.5 Hz, 1H), 2.28-2.16 (m, 8H), 1.97 (d, J=6.9 Hz, 3H), 1.77-1.64 (m, 2H), 1.51-1.31 (m, 6H). $^{13}$C NMR (75 MHz, CDCl$_3$) δ 175.8, 170.0, 141.7, 138.2, 135.6, 134.7, 131.2, 129.7, 129.4 (2C), 128.9, 128.2 (2C), 127.4, 124.6, 110.4, 59.8, 57.7, 46.7, 45.6 (2C), 40.9, 40.7, 27.6, 27.4, 27.2, 26.9, 21.8. HRMS (ESI) calcd for C$_{28}$H$_{33}$Cl$_2$N$_6$O$_2$ 555.2042 (M+H)$^+$, found 555.2039.

(R)-5'-Chloro-3-((S)-1-(4-chlorophenyl)ethyl)-1'-(8-(dimethylamino)octyl)-4,6-dihydrospiro[[1,2,3]triazolo[4,5-b]pyridine-7,3'-indoline]-2',5(3H)-dione (69). Compound 69 (13 mg, 92%) was prepared by a procedure similar to that used to prepare compound 55. The title compound was obtained as a yellow solid. HPLC purity 98.9% (t$_R$=19.66 min). $^1$H NMR (300 MHz, CDCl$_3$) δ 7.37-7.27 (m, 5H), 7.13 (d, J=2.1 Hz, 1H), 6.87 (d, J=8.4 Hz, 1H), 5.84 (s, 1H), 5.57 (q, J=6.9 Hz, 1H), 3.82-3.63 (m, 2H), 2.97 (s, 2H), 2.29-2.16 (m, 8H), 1.97 (d, J=6.9 Hz, 3H), 1.76-1.64 (m, 2H), 1.48-1.22 (m, 10H). $^{13}$C NMR (75 MHz, CDCl$_3$) δ 175.8, 169.9, 141.7, 138.1, 135.7, 134.7, 131.2, 129.7, 129.5 (2C), 128.9, 128.1 (2C), 127.4, 124.6, 110.4, 60.0, 57.7, 46.7, 45.6 (2C), 40.9, 40.7, 29.5, 29.2, 27.7, 27.5, 27.4, 26.9, 21.7. HRMS (ESI) calcd for C$_{30}$H$_{37}$Cl$_2$N$_6$O$_2$ 583.2355 (M+H)$^+$, found 583.2354.

(R)-5'-Chloro-3-((S)-1-(4-chlorophenyl)ethyl)-1'-(10-(dimethylamino)decyl)-4,6-dihydrospiro[[1,2,3]triazolo[4,5-b]pyridine-7,3'-indoline]-2',5(3H)-dione (70). Compound 70 (12 mg, 85%) was prepared by a procedure similar to that used to prepare compound 55. The title compound was obtained as a yellow solid. HPLC purity 95.0% (t$_R$=19.46 min). $^1$H NMR (300 MHz, CDCl$_3$) δ 7.37-7.27 (m, 5H), 7.13 (d, J=2.1 Hz, 1H), 6.87 (d, J=8.4 Hz, 1H), 5.57 (q, J=6.9 Hz, 1H), 5.46 (s, 1H), 3.79-3.63 (m, 2H), 2.96 (s, 2H), 2.31-2.19 (m, 8H), 1.97 (d, J=6.9 Hz, 3H), 1.76-1.62 (m, 2H), 1.51-1.40 (m, 2H), 1.37-1.22 (m, 12H). $^{13}$C NMR (75 MHz, CDCl$_3$) δ 175.8, 169.8, 141.7, 138.1, 135.9, 134.7, 131.1, 129.6, 129.5 (2C), 128.9, 128.1 (2C), 127.5, 124.6, 110.4, 60.0, 57.7, 46.7, 45.6 (2C), 41.0, 40.7, 29.6, 29.5, 29.5, 29.2, 27.8, 27.6, 27.4, 26.8, 21.7. HRMS (ESI) calcd for C$_{32}$H$_{41}$Cl$_2$N$_6$O$_2$ 611.2668 (M+H)$^+$, found 611.2664.

2-((R)-5'-Chloro-3-((S)-1-(4-chlorophenyl)ethyl)-2',5-dioxo-3,4,5,6-tetrahydrospiro[[1,2,3]triazolo[4,5-b]pyridine-7,3'-indolin]-1'-yl)ethyl 8-(5-((3aS,4S,6aR)-2-oxohexahydro-1H-thieno[3,4-d]imidazol-4-yl)pentanamido)octanoate (73). To a solution of methyl 8-aminooctanoate hydrochloride (129 mg, 0.614 mmol) and D-(+)-Biotin (100 mg, 0.409 mmol) in 6 mL of DMF was added EDCI (118 mg, 0.614 mmol), HOBt (83 mg, 0.614 mmol) and DIEA (106 mg, 0.818 mmol) successively. The resulting mixture was stirred at r.t. overnight and then diluted with EtOAc/MeOH (150 mL, 3/1). The mixture was washed with water (3×30 mL) and brine (30 mL), dried over Na$_2$SO$_4$ and concentrated in vacuo. The residue was dissolved in MeOH/H$_2$O (6 mL/4 mL), and then NaOH (82 mg, 2.05 mmol) was added. The resulting mixture was stirred at r.t. for 3 h. Then the solvent (MeOH) was evaporated and the pH value was adjusted to 5-6 with 2 M HCl (aq.) at 0° C. The white precipitate was isolated by filtration, washed with water and dried under vacuum to give 8-(5-((3aS,4S,6aR)-2-oxohexahydro-1H-thieno[3,4-d]imidazol-4-yl)pentanamido)octanoic acid 72 (110 mg, 70% in two steps) as a white solid. $^1$H NMR (300 MHz, DMSO-d6) δ 11.99 (s, 1H), 7.73 (t, J=5.4 Hz, 1H), 6.50-6.20 (m, 2H), 4.30 (dd, J=7.8, 4.8 Hz, 1H), 4.12 (dd, J=7.8, 4.5 Hz, 1H), 3.14-3.05 (m, 1H), 3.04-2.95 (m, 2H), 2.82 (dd, J=12.6, 5.1 Hz, 1H), 2.57 (d, J=12.3 Hz, 1H), 2.18 (t, J=7.2 Hz, 2H), 2.04 (t, J=7.2 Hz, 2H), 1.67-1.19 (m, 16H). $^{13}$C NMR (75 MHz, DMSO-d6) δ 174.5, 171.8, 162.7, 61.0, 59.2, 55.4, 38.8, 35.2, 33.7, 29.1, 28.5, 28.5, 28.2, 28.0, 26.3, 25.3, 24.4.

To a solution of compound 72 (42 mg, 0.11 mmol) and compound 42 (26 mg, 0.055 mmol) in 3 mL of DMF was added EDCI (21 mg, 0.011 mmol) and DMAP (2 mg, 0.011 mmol). The resulting mixture was stirred at 50° C. for 48 h. Then the mixture was diluted with EtOAc/MeOH (80 mL, 3/1), washed with water (2×20 mL) and brine (15 mL), and concentrated. The residue was purified by preparative TLC developed by 5% MeOH in DCM to give compound 73 (9 mg, 63%) as a white solid, and 18 mg of compound 42 was recovered. HPLC purity 95.0% (t$_R$=19.18 min). 41 NMR (300 MHz, CDCl$_3$) δ 11.76 (s, 1H), 7.42 (d, J=8.4 Hz, 2H), 7.36-7.28 (m, 3H), 7.16 (d, J=1.8 Hz, 1H), 6.90 (d, J=8.4 Hz, 1H), 6.67 (s, 1H), 6.01 (s, 1H), 5.80 (q, J=6.9 Hz, 1H), 5.16 (s, 1H), 4.62-4.48 (m, 2H), 4.42-4.32 (m, 1H), 4.25-4.06 (m, 2H), 3.83-3.71 (m, 1H), 3.29-3.08 (m, 3H), 3.02-2.68 (m, 4H), 2.31-2.08 (m, 4H), 1.97 (d, J=6.9 Hz, 3H), 1.79-1.57 (m, 4H), 1.53-1.33 (m, 6H), 1.24-0.99 (m, 6H). $^{13}$C NMR (75 MHz, CDCl$_3$) δ 176.2, 173.6, 173.4, 169.6, 164.3, 141.7, 138.8, 136.5, 134.3, 131.1, 129.4, 129.2 (2C), 129.0, 128.6

(2C), 126.6, 124.8, 110.2, 62.2, 60.7, 60.3, 57.0, 55.5, 46.6, 40.9, 40.8, 40.0, 39.4, 36.1, 34.0, 29.3, 28.6, 28.5, 28.2, 28.1, 26.3, 25.7, 24.3, 21.8. FIRMS (ESI) calcd for $C_{40}H_{49}Cl_2N_8O_6S$ 839.2873 (M+H)$^+$, found 839.2877.

2-((S)-5'-Chloro-3-((S)-1-(4-chlorophenyl)ethyl)-2',5-dioxo-3,4,5,6-tetrahydrospiro[[1,2,3]triazolo[4,5-b]pyridine-7,3'-indolin]-1'-yl)ethyl 8-(5-((3aS,4S,6aR)-2-oxohexahydro-1H-thieno[3,4-d]imidazol-4-yl)pentanamido)octanoate (75). Compound 75 (19 mg, 60%) was prepared by a route similar to that used to prepare compound 73 starting from compound 1b and 72. The title compound was obtained as a white solid. HPLC purity 98.3% ($t_R$=19.15 min). 41 NMR (300 MHz, CDCl$_3$) δ 11.69 (s, 1H), 7.40 (d, J=8.4 Hz, 2H), 7.34-7.27 (m, 3H), 7.13 (d, J=1.8 Hz, 1H), 6.91 (d, J=8.4 Hz, 1H), 6.59 (s, 1H), 6.37 (s, 1H), 5.81 (q, J=6.9 Hz, 1H), 5.49 (s, 1H), 4.60-4.38 (m, 2H), 4.37-4.17 (m, 2H), 4.17-4.05 (m, 1H), 3.88-3.75 (m, 1H), 3.29-3.09 (m, 3H), 2.99-2.81 (m, 3H), 2.73 (d, J=12.9 Hz, 1H), 2.27-2.13 (m, 4H), 1.96 (d, J=6.9 Hz, 3H), 1.75-1.56 (m, 4H), 1.51-1.35 (m, 6H), 1.32-1.08 (m, 6H). $^{13}$C NMR (75 MHz, CDCl$_3$) δ 176.2, 173.7, 173.5, 169.5, 164.3, 141.4, 138.8, 136.5, 134.3, 131.2, 129.5, 129.2 (2C), 129.0, 128.6 (2C), 126.7, 124.7, 110.2, 62.1, 60.5, 60.4, 57.1, 55.7, 46.7, 41.1, 40.7, 39.8, 39.6, 36.1, 34.0, 29.3, 28.5 (2C), 28.3, 28.0, 26.4, 25.7, 24.3, 21.9. HRMS (ESI) calcd for $C_{40}H_{49}Cl_2N_8O_6S$ 839.2873 (M+H)$^+$, found 839.2875.

Luciferase Reporter Replicon-Based Screening. Huh7 cells containing a luciferase reporter replicon of DENY-1 (strain WestPac), DENV-2 (New Guinea C strain, NGC), DENV-3 (strain D3MY05-34640) and DENV-4 (strain D4MY01-22713) were used in this study. The replicon cells containing the *Renilla* luciferase and neomycin-resistance genes were generated using a similar strategy as described previously.[55] Briefly, Huh7 DENY-1 to -4 replicon cells were seeded at a density of 10 k per well in a 96-well microplate. After incubation at 37° C. with 5% CO$_2$ overnight, the cells were treated with 2-fold serial dilutions of compounds. Experiments were performed in duplicates. After 48 h of incubation, luciferase activities were measured using the EnduRen live-cell substrate (Promega) by following the manufacturer's instructions. The dose-dependent curve was plotted and EC$_{50}$ values were calculated using four parameter logistic regression in GraphPad software Prism 8.0.

Cytotoxicity Assay. Huh7 cells or Huh7 replicon cells were seeded in a 96-well plate. After incubation at 37° C. with 5% CO$_2$ overnight, the cells were treated with 2-fold serial dilutions of compounds. Experiments were performed in duplicates. After 48 h of incubation, cell viability was measured by adding the CellTiter-Glo reagent (Promega) to each well. The cell viability in 0.45% DMSO-treatment groups was treated at 100%. The cell viability in compound-treated wells was normalized to that of DMSO-treated wells. CC$_{50}$ values were calculated using four parameter logistic regression in GraphPad software Prism 8.0.

Viral Titer Reduction Assay. Huh7 cells were seeded in a 96-well plate. The next day, cells were infected with DENV-2 strains NGC or D2Y98P at a MOI of 0.3 in the presence of 2-fold serial dilutions of compounds. Experiments were performed in triplicates. After incubation at 37° C. for 48 h, cell culture fluids were harvested. The infectious viruses in the culture fluids were determined by plaque assay using a protocol as described previously.[48] The EC$_{50}$ values were calculated using four parameter logistic regression in GraphPad software Prism 8.0.

Pull-Down Assay. 4×10$^6$ Huh7 cells were seeded in a T-75 flask. The next day, cells were infected with DENV-2 strain NGC at a MOI of 2.0 in the presence of 10 μM compound 73 or 75. Cells treated with 0.25% DMSO were used as a control. After 48 h-incubation at 37° C., cells were harvested and lysed in 500 μL lysis buffer comprising 20 mM Tris-HCL pH 7.5, 100 mM NaCl, 0.5% DDM, and EDTA-free protease inhibitor cocktail (Roche). After removing the cell debris by centrifugation at 15000 rpm for 10 min, the lysates were mixed with corresponding compound at a final concentration of 100 μM or DMSO (0.25%) prior to incubation with 80 μL Streptavidin Magnetic Beads (ThermoFisher Scientific). After incubation at 4° C. overnight with agitation, the beads were washed 5 times with PBST buffer (PBS containing 0.1% Tween 20). The beads were finally mixed with 1×LDS sample buffer (ThermoFisher Scientific) containing 100 mM dithiothreitol (DTT, Sigma-Aldrich) and heated at 95° C. for 10 minutes to elute the bead-associated proteins. The eluates and cell lysates were loaded onto a 12% SDS-PAGE and viral NS4B proteins were detected by a mouse monoclonal antibody according to the protocol as reported previously.[56]

Selection of Resistant Viruses. Resistant viruses were selected by serial passaging of the DENV-2 strain NGC strain on Huh7 cells in the presence of increasing concentrations of compound 63 using a previously described protocol with some modifications.[53] Four selections in the presence of compound 63 and two selections in the presence of 0.45% DMSO were performed independently. In brief, Huh7 cells in a 12-well plate were infected by DENV-2 Strain NGC or previously passaged viruses. After incubation at 30° C. for 1 h, the inoculum was changed to fresh medium with 2% FBS containing corresponding concentration of compound 63 or DMSO. The cells were incubated at 37° C. for 3 days. A part of the supernatants from each passage were collected and stored at −80° C. The P12 viruses were tested for compound sensitivity by viral reduction assay. For whole-genome sequencing, viral RNA was extracted from the P12 supernatants. cDNA of the viral entire genome was amplified by RT-PCR and subjected to Sanger sequencing.

In Vivo PK Studies. The PK profiles of compound 15 were determined in male SD rats following intravenous (i.v.) and oral (p.o.) administration of 10 and 20 mg/kg, respectively. The formulations used for i.v. and p.o. were solution in DMSO: 20% HP-(3-CD in saline=1:9. IV bolus injection, animal number N=3; dose level: 10 mg/kg; sample collection time points: 5 min, 15 min, 30 min, 1 h, 2 h, 4 h, 8 h, 24 h; PO: animal number N=3; fasting 12 h, dose level: 20 mg/kg; sample collection time points: 15 min, 30 min, 1 h, 2 h, 4 h, 8 h, 24 h. Plasma concentrations of compound 15 were measured by API-4000/5500 LC-MS/MS with 8 point standard curve and 6 QCs. Pharmacokinetic parameters were calculated by a non-compartmental approach using WinNonLin software.

In Vivo Efficacy Studies. Animal studies were performed as approved by the University of Texas Medical Branch (UTMB) Institutional Animal Care and Use Committee (IACUC). All efforts were made to minimize animal suffering. The in vivo efficacy of compound 15 was evaluated in a dengue viremia model.[57] 3-week-old A129 mice (with knockout of IFN-α/β receptors) and DENV-2 strain D2Y98P were used in this model. The virus stock was propagated in BHK-21 cells grown in RPMI 1640 medium. 100 μL (10$^7$ PFU/ml) of D2Y98P viruses were injected subcutaneously (S.C.) into the mice. The mice (n=6 per group) immediately were dosed orally twice daily (BID) with compound 15 (100 mg/kg) or the vehicle for 3 days. The compound was reconstituted as a suspension in the vehicle solution containing 2.5% DMSO, 50% PEG-400 and 47.5% DPBS. On day 3 post-infection (p.i.), the mice were bled via the retro-orbital (R.O.) route. The plasma was collected and used for measuring the viral loads in the sera (Viremia) by plaque assay. The means and standard deviations were presented. Statistical analysis was performed by an unpaired parametric test using Prism software (GraphPad). Mouse weight was carefully monitored for 12 d after infection. A two-way ANOVA with multiple comparison was performed to analyze the statistically significant difference between compound 15 and vehicle-treated groups.

Abbreviations Used

DENV, dengue virus; DHF, dengue hemorrhagic fever; DSS, dengue shock syndrome; SAR, structure-activity relationship; WHO, World Health Organization; TLC, thin layer chromatography; UV, ultraviolet; TMS, tetramethylsilane; HRMS, high-resolution mass spectrometry; HPLC, high-performance liquid chromatography; HOBt, 1-hydroxybenzotriazole; DIEA, N,N-diisopropylethylamine; DCM, dichloromethane; DMAP, 4-(dimethylamino)pyridine; DMF, N,N-dimethylformamide; DMSO, dimethyl sulfoxide; EtOAc, ethyl acetate; LiHDMS, lithium bis(trimethylsilyl)amide; THF, tetrahydrofuran; TsOH, p-toluenesulfonic acid; iv, intravenous injection; po, oral administration; PROTAC, proteolysis targeting chimera.

REFERENCES

1. *Dengue: Guidelines for Diagnosis, Treatment, Prevention and Control*. World Health Organization: Geneva, 2009.
2. Whitehorn, J.; Simmons, C. P. The Pathogenesis of Dengue. *Vaccine*. 2011, 29, 7221-7228.
3. Brady, O. J.; Gething, P. W.; Bhatt, S.; Messina, J. P.; Brownstein, J. S.; Hoen, A. G.; Moyes, C. L.; Farlow, A. W.; Scott, T. W.; Hay, S. I. Refining the Global Spatial Limits of Dengue Virus Transmission by Evidence-Based Consensus. *PLoS Negl. Trop. Dis.* 2012, 6, e1760.
4. Jentes, E. S.; Lash, R. R.; Johansson, M. A.; Sharp, T. M.; Henry, R.; Brady, O. J.; Sotir, M. J.; Hay, S. I.; Margolis, H. S.; Brunette, G. W. Evidence-Based Risk Assessment and Communication: A New Global Dengue-Risk Map for Travellers and Clinicians. *J. Travel Med.* 2016, 23, 1-5.
5. *Global Strategy for Dengue Prevention and Control 2012-2020*. World Health Organization: Geneva, 2012.
6. Bhatt, S.; Gething, P. W.; Brady, O. J.; Messina, J. P.; Farlow, A. W.; Moyes, C. L.; Drake, J. M.; Brownstein, J. S.; Hoen, A. G.; Sankoh, O.; Myers, M. F.; George, D. B.; Jaenisch, T.; Wint, G. R.; Simmons, C. P.; Scott, T. W.; Farrar, J. J.; Hay, S. I. The Global Distribution and Burden of Dengue. *Nature*. 2013, 496, 504-507.
7. Stanaway, J. D.; Shepard, D. S.; Undurraga, E. A.; Halasa, Y. A.; Coffeng, L. E.; Brady, O. J.; Hay, S. I.; Bedi, N.; Bensenor, I. M.; Castaneda-Orjuela, C. A.; Chuang, T. W.; Gibney, K. B.; Memish, Z. A.; Rafay, A.; Ukwaja, K. N.; Yonemoto, N.; Murray, C. J. L. The Global Burden of Dengue: An Analysis from the Global Burden of Disease Study 2013. *Lancet Infect. Dis.* 2016, 16, 712-723.
8. Stevens, A. J.; Gahan, M. E.; Mahalingam, S.; Keller, P. A. The Medicinal Chemistry of Dengue Fever. *J. Med. Chem.* 2009, 52, 7911-7926.
9. Chao, B.; Tong, X. K.; Tang, W.; Li, D. W.; He, P. L.; Garcia, J. M.; Zeng, L. M.; Gao, A. H.; Yang, L.; Li, J.; Nan, F. J.; Jacobs, M.; Altmeyer, R.; Zuo, J. P.; Hu, Y. H. Discovery and Optimization of 2,4-Diaminoquinazoline Derivatives as a New Class of Potent Dengue Virus Inhibitors. *J. Med. Chem.* 2012, 55, 3135-3143.
10. Lim, S. P.; Wang, Q. Y.; Noble, C. G.; Chen, Y. L.; Dong, H.; Zou, B.; Yokokawa, F.; Nilar, S.; Smith, P.; Beer, D.; Lescar, J.; Shi, P. Y. Ten Years of Dengue Drug Discovery: Progress and Prospects. *Antiviral Res.* 2013, 100, 500-519.
11. Nitsche, C.; Holloway, S.; Schirmeister, T.; Klein, C. D. Biochemistry and Medicinal Chemistry of the Dengue Virus Protease. *Chem. Rev.* 2014, 114, 11348-11381.
12. Beesetti, H.; Khanna, N.; Swaminathan, S. Drugs for Dengue: A Patent Review (2010-2014). *Expert Opin. Ther. Pat.* 2014, 24, 1171-1184.
13. Behnam, M. A.; Nitsche, C.; Boldescu, V.; Klein, C. D. The Medicinal Chemistry of Dengue Virus. *J. Med. Chem.* 2016, 59, 5622-5649.
14. *Informing Vaccination Programs: A Guide to the Design and Conduct of Dengue Serosurveys*. World Health Organization: Geneva, 2017.
15. Ye, N.; Chen, H.; Wold, E. A.; Shi, P. Y.; Zhou, J. Therapeutic Potential of Spirooxindoles as Antiviral Agents. *ACS Infect. Dis.* 2016, 2, 382-392.
16. Verdonck, S.; Pu, S.-Y.; Sorrell, F. J.; Elkins, J. M.; Froeyen, M.; Gao, L.-J.; Prugar, L. I.; Dorosky, D. E.; Brannan, J. M.; Barouch-Bentov, R.; Knapp, S.; Dye, J. M.; Herdewijn, P.; Einav, S.; De Jonghe, S. Synthesis and Structure-Activity Relationships of 3,5-Disubstituted-Pyrrolo[2,3-b]Pyridines as Inhibitors of Adaptor-Associated Kinase 1 with Antiviral Activity. *J. Med. Chem.* 2019, 62, 5810-5831.
17. Yang, Y.; Cao, L.; Gao, H.; Wu, Y.; Wang, Y.; Fang, F.; Lan, T.; Lou, Z.; Rao, Y. Discovery, Optimization, and Target Identification of Novel Potent Broad-Spectrum Antiviral Inhibitors. *J. Med. Chem.* 2019, 62, 4056-4073.
18. *Global Advisory Committee on Vaccine Safety, 6-7 Jun. 2018*. Weekly Epidemiological Record: World Health Organization: Geneva, 2018; Vol. 93, p 389-396.
19. Vannice, K. S.; Wilder-Smith, A.; Barrett, A. D. T.; Carrijo, K.; Cavaleri, M.; de Silva, A.; Durbin, A. P.; Endy, T.; Harris, E.; Innis, B. L.; Katzelnick, L. C.; Smith, P. G.; Sun, W.; Thomas, S. J.; Hombach, J. Clinical Development and Regulatory Points for Consideration for Second-Generation Live Attenuated Dengue Vaccines. *Vaccine*. 2018, 36, 3411-3417.
20. *Dengue Vaccine: WHO Position Paper—September 2018*. Weekly Epidemiological Record: World Health Organization: Geneva, 2018; Vol. 93, p 457-476.
21. Messina, J. P.; Brady, O. J.; Scott, T. W.; Zou, C.; Pigott, D. M.; Duda, K. A.; Bhatt, S.; Katzelnick, L.; Howes, R. E.; Battle, K. E.; Simmons, C. P.; Hay, S. I. Global Spread of Dengue Virus Types: Mapping the 70 Year History. *Trends Microbiol.* 2014, 22, 138-146.
22. Guzman, M. G.; Harris, E. Dengue. *Lancet*. 2015, 385, 453-465.
23. Halsey, E. S.; Marks, M. A.; Gotuzzo, E.; Fiestas, V.; Suarez, L.; Vargas, J.; Aguayo, N.; Madrid, C.; Vimos, C.; Kochel, T. J.; Laguna-Torres, V. A. Correlation of Serotype-Specific Dengue Virus Infection with Clinical Manifestations. *PLoS Negl. Trop. Dis.* 2012, 6, e1638.
24. Rocha, B. A. M.; Guilarde, A. O.; Argolo, A. F. L. T.; Tassara, M. P.; da Silveira, L. A.; Junqueira, I. C.; Turchi, M. D.; Féres, V. C. R.; Martelli, C. M. T. Dengue-Specific Serotype Related to Clinical Severity During the 2012/2013 Epidemic in Centre of Brazil. *Infect Dis Poverty.* 2017, 6, 116.
25. Yung, C. F.; Lee, K. S.; Thein, T. L.; Tan, L. K.; Gan, V. C.; Wong, J. G. X.; Lye, D. C.; Ng, L. C.; Leo, Y. S.

25. Dengue Serotype-Specific Differences in Clinical Manifestation, Laboratory Parameters and Risk of Severe Disease in Adults, Singapore. *Am. J. Trop. Med. Hyg.* 2015, 92, 999-1005.
26. Montoya, M.; Gresh, L.; Mercado, J. C.; Williams, K. L.; Vargas, M. J.; Gutierrez, G.; Kuan, G.; Gordon, A.; Balmaseda, A.; Harris, E. Symptomatic Versus Inapparent Outcome in Repeat Dengue Virus Infections Is Influenced by the Time Interval between Infections and Study Year. *PLoS Negl. Trop. Dis.* 2013, 7, e2357.
27. Reich, N. G.; Shrestha, S.; King, A. A.; Rohani, P.; Lessler, J.; Kalayanarooj, S.; Yoon, I. K.; Gibbons, R. V.; Burke, D. S.; Cummings, D. A. Interactions between Serotypes of Dengue Highlight Epidemiological Impact of Cross-Immunity. *J. R. Soc. Interface.* 2013, 10, 20130414.
28. Sangkawibha, N.; Rojanasuphot, S.; Ahandrik, S.; Viriyapongse, S.; Jatanasen, S.; Salitul, V.; Phanthumachinda, B.; Halstead, S. B. Risk Factors in Dengue Shock Syndrome: A Prospective Epidemiologic Study in Rayong, Thailand. I. The 1980 Outbreak. *Am. J. Epidemiol.* 1984, 120, 653-669.
29. Thein, S.; Aung, M. M.; Shwe, T. N.; Aye, M.; Zaw, A.; Aye, K.; Aye, K. M.; Aaskov, J. Risk Factors in Dengue Shock Syndrome. *Am. J. Trop. Med. Hyg.* 1997, 56, 566-572.
30. Graham, R. R.; Juffrie, M.; Tan, R.; Hayes, C. G.; Laksono, I.; Ma'roef, C.; Erlin; Sutaryo; Porter, K. R.; Halstead, S. B. A Prospective Seroepidemiologic Study on Dengue in Children Four to Nine Years of Age in Yogyakarta, Indonesia I. Studies in 1995-1996. *Am. J. Trop. Med. Hyg.* 1999, 61, 412-419.
31. Endy, T. P.; Yoon, I. K.; Mammen, M. P. Prospective Cohort Studies of Dengue Viral Transmission and Severity of Disease. *Curr. Top. Microbiol. Immunol.* 2010, 338, 1-13.
32. Guzman, M. G.; Alvarez, M.; Halstead, S. B. Secondary Infection as a Risk Factor for Dengue Hemorrhagic Fever/Dengue Shock Syndrome: An Historical Perspective and Role of Antibody-Dependent Enhancement of Infection. *Arch. Virol.* 2013, 158, 1445-1459.
33. Yokokawa, F.; Nilar, S.; Noble, C. G.; Lim, S. P.; Rao, R.; Tania, S.; Wang, G.; Lee, G.; Hunziker, J.; Karuna, R.; Manjunatha, U.; Shi, P. Y.; Smith, P. W. Discovery of Potent Non-Nucleoside Inhibitors of Dengue Viral RNA-Dependent RNA Polymerase from a Fragment Hit Using Structure-Based Drug Design. *J. Med. Chem.* 2016, 59, 3935-3952.
34. Noble, C. G.; Shi, P. Y. Structural Biology of Dengue Virus Enzymes: Towards Rational Design of Therapeutics. *Antiviral Res.* 2012, 96, 115-126.
35. Li, Y.; Wong, Y. L.; Lee, M. Y.; Li, Q.; Wang, Q. Y.; Lescar, J.; Shi, P. Y.; Kang, C. Secondary Structure and Membrane Topology of the Full-Length Dengue Virus NS4B in Micelles. *Angew. Chem. Int. Ed. Engl.* 2016, 55, 12068-12072.
36. Xie, X.; Zou, J.; Wang, Q. Y.; Shi, P. Y. Targeting Dengue Virus NS4B Protein for Drug Discovery. *Antiviral Res.* 2015, 118, 39-45.
37. Zou, J.; Xie, X.; Lee le, T.; Chandrasekaran, R.; Reynaud, A.; Yap, L.; Wang, Q. Y.; Dong, H.; Kang, C.; Yuan, Z.; Lescar, J.; Shi, P. Y. Dimerization of Flavivirus NS4B Protein. *J. Virol.* 2014, 88, 3379-3391.
38. Youn, S.; Li, T.; McCune, B. T.; Edeling, M. A.; Fremont, D. H.; Cristea, I. M.; Diamond, M. S. Evidence for a Genetic and Physical Interaction between Nonstructural Proteins NS1 and NS4B That Modulates Replication of West Nile Virus. *J. Virol.* 2012, 86, 7360-7371.
39. Umareddy, I.; Chao, A.; Sampath, A.; Gu, F.; Vasudevan, S. G. Dengue Virus NS4B Interacts with NS3 and Dissociates It from Single-Stranded Rna. *J. Gen. Virol.* 2006, 87, 2605-2614.
40. Zou, J.; Lee le, T.; Wang, Q. Y.; Xie, X.; Lu, S.; Yau, Y. H.; Yuan, Z.; Geifman Shochat, S.; Kang, C.; Lescar, J.; Shi, P. Y. Mapping the Interactions between the NS4B and NS3 Proteins of Dengue Virus. *J. Virol.* 2015, 89, 3471-3483.
41. Tajima, S.; Takasaki, T.; Kurane, I. Restoration of Replication-Defective Dengue Type 1 Virus Bearing Mutations in the N-Terminal Cytoplasmic Portion of NS4A by Additional Mutations in NS4B. *Arch. Virol.* 2011, 156, 63-69.
42. Li, X. D.; Ye, H. Q.; Deng, C. L.; Liu, S. Q.; Zhang, H. L.; Shang, B. D.; Shi, P. Y.; Yuan, Z. M.; Zhang, B. Genetic Interaction between NS4A and NS4B for Replication of Japanese Encephalitis Virus. *J. Gen. Virol.* 2015, 96, 1264-1275.
43. Zou, J.; Xie, X.; Wang, Q. Y.; Dong, H.; Lee, M. Y.; Kang, C.; Yuan, Z.; Shi, P. Y. Characterization of Dengue Virus NS4A and NS4B Protein Interaction. *J. Virol.* 2015, 89, 3455-3470.
44. Munoz-Jordan, J. L.; Laurent-Rolle, M.; Ashour, J.; Martinez-Sobrido, L.; Ashok, M.; Lipkin, W. I.; Garcia-Sastre, A. Inhibition of Alpha/Beta Interferon Signaling by the NS4B Protein of Flaviviruses. *J. Virol.* 2005, 79, 8004-8013.
45. Munoz-Jordan, J. L.; Sanchez-Burgos, G. G.; Laurent-Rolle, M.; Garcia-Sastre, A. Inhibition of Interferon Signaling by Dengue Virus. *Proc. Natl. Acad. Sci. U.S.A.* 2003, 100, 14333-14338.
46. Kounde, C. S.; Yeo, H. Q.; Wang, Q. Y.; Wan, K. F.; Dong, H.; Karuna, R.; Dix, I.; Wagner, T.; Zou, B.; Simon, O.; Bonamy, G. M. C.; Yeung, B. K. S.; Yokokawa, F. Discovery of 2-Oxopiperazine Dengue Inhibitors by Scaffold Morphing of a Phenotypic High-Throughput Screening Hit. *Bioorg. Med. Chem. Lett.* 2017, 27, 1385-1389.
47. Bardiot, D.; Koukni, M.; Smets, W.; Carlens, G.; McNaughton, M.; Kaptein, S.; Dallmeier, K.; Chaltin, P.; Neyts, J.; Marchand, A. Discovery of Indole Derivatives as Novel and Potent Dengue Virus Inhibitors. *J. Med. Chem.* 2018, 61, 8390-8401.
48. Xie, X.; Wang, Q. Y.; Xu, H. Y.; Qing, M.; Kramer, L.; Yuan, Z.; Shi, P. Y. Inhibition of Dengue Virus by Targeting Viral NS4B Protein. *J. Virol.* 2011, 85, 11183-11195.
49. van Cleef, K. W.; Overheul, G. J.; Thomassen, M. C.; Kaptein, S. J.; Davidson, A. D.; Jacobs, M.; Neyts, J.; van Kuppeveld, F. J.; van Rij, R. P. Identification of a New Dengue Virus Inhibitor That Targets the Viral NS4B Protein and Restricts Genomic RNA Replication. *Antiviral Res.* 2013, 99, 165-171.
50. Patkar, C. G.; Larsen, M.; Owston, M.; Smith, J. L.; Kuhn, R. J. Identification of Inhibitors of Yellow Fever Virus Replication Using a Replicon-Based High-Throughput Assay. *Antimicrob. Agents Chemother.* 2009, 53, 4103-4114.
51. Zou, B.; Chan, W. L.; Ding, M.; Leong, S. Y.; Nilar, S.; Seah, P. G.; Liu, W.; Karuna, R.; Blasco, F.; Yip, A.; Chao, A.; Susila, A.; Dong, H.; Wang, Q. Y.; Xu, H. Y.; Chan, K.; Wan, K. F.; Gu, F.; Diagana, T. T.; Wagner, T.; Dix, I.; Shi, P. Y.; Smith, P. W. Lead Optimization of Spiropyrazolopyridones: A New and Potent Class of Dengue Virus Inhibitors. *ACS Med. Chem. Lett.* 2015, 6, 344-348.

52. Chan, W. L.; Ding, M.; Zou, B. Preparation of Spiro-pyrazolopyridine Derivatives and Uses Thereof for the Treatment of Viral Infections. WO2014167528A1, 2014.
53. Wang, Q. Y.; Dong, H.; Zou, B.; Karuna, R.; Wan, K. F.; Zou, J.; Susila, A.; Yip, A.; Shan, C.; Yeo, K. L.; Xu, H.; Ding, M.; Chan, W. L.; Gu, F.; Seah, P. G.; Liu, W.; Lakshminarayana, S. B.; Kang, C.; Lescar, J.; Blasco, F.; Smith, P. W.; Shi, P. Y. Discovery of Dengue Virus NS4B Inhibitors. *J. Virol.* 2015, 89, 8233-8244.
54. Wang, P.; Zhou, J. Proteolysis Targeting Chimera (PROTAC): A Paradigm-Shifting Approach in Small Molecule Drug Discovery. *Curr. Top. Med. Chem.* 2018, 18, 1354-1356.
55. Xie, X.; Zou, J.; Shan, C.; Yang, Y.; Kum, D. B.; Dallmeier, K.; Neyts, J.; Shi, P.-Y. Zika Virus Replicons for Drug Discovery. *E Bio Medicine*. 2016, 12, 156-160.
56. Xie, X.; Zou, J.; Wang, Q. Y.; Noble, C. G.; Lescar, J.; Shi, P. Y. Generation and Characterization of Mouse Monoclonal Antibodies against NS4B Protein of Dengue Virus. *Virology*. 2014, 450-451, 250-257.
57. Xie, X.; Yang, Y.; Muruato, A. E.; Zou, J.; Shan, C.; Nunes, B. T.; Medeiros, D. B.; Vasconcelos, P. F.; Weaver, S. C.; Rossi, S. L.; Shi, P. Y. Understanding Zika Virus Stability and Developing a Chimeric Vaccine through Functional Analysis. *MBio*. 2017, 8, 1-14.

REFERENCES

A number of patents and publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

We claim:
1. A compound of Formula (I)

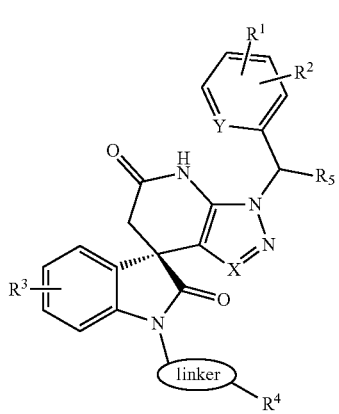

wherein:
$R^1$, $R^2$ are independently chosen from H, F, Cl, Br and $CF_3$;
$R^3$ is F, Cl or Br;
$R^4$ is F, Cl, Br, alkyl, alkenyl, alkynyl, alkoxy, hydroxyl, carboxyl, ester, acetal, amino, 5-membered cycle or heterocycle, or 6-membered cycle or heterocycle;
$R^5$ is H or alkyl;
X, Y are independently chosen from CH and N; and
linker is a 1-20 atom length carbon chain, wherein said chain optionally includes one or more ester bonds, amide bonds or oxygen atoms.

2. The compound according to claim 1, wherein:
wherein X is CH, Y is CH, $R^3$=Cl, and $R^5$ is H.

3. A compound according to Formula Ib, wherein:

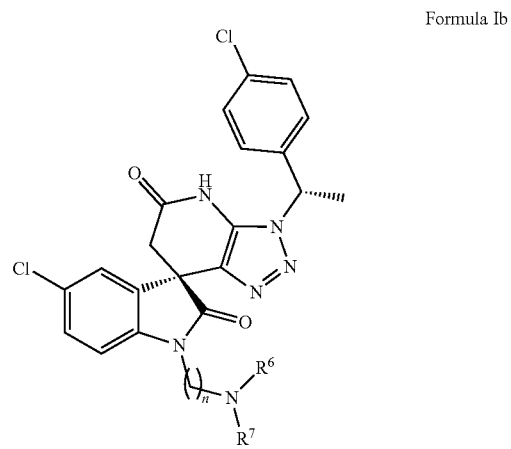

wherein $R^6$, $R^7$ are independently chosen from H and alkyl; or $R^6$ and $R^7$ taken together with the N atom to which they are attached to form a form 5-membered or 6-membered heterocycle ring; and
n is 1-10.

4. A compound according to formula Ic, wherein:

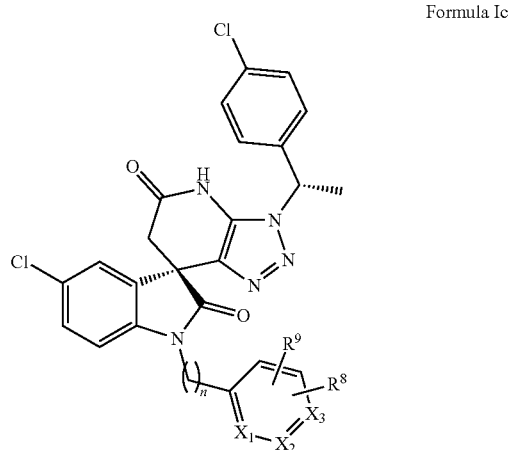

wherein $R^8$, $R^9$ is independently chosen from H, alkyl, alkoxy, F, Cl, Br, $CF_3$, hydroxyl, carboxyl, ester, cyano, amino, and nitro, or $R^8$ and $R^9$ taken together with the atoms to which they are attached form 5-membered or 6-membered fused ring;
$X_1$, $X_2$, $X_3$ are independently chosen from CH and N; and
n is 1-10.

5. A compound represented by
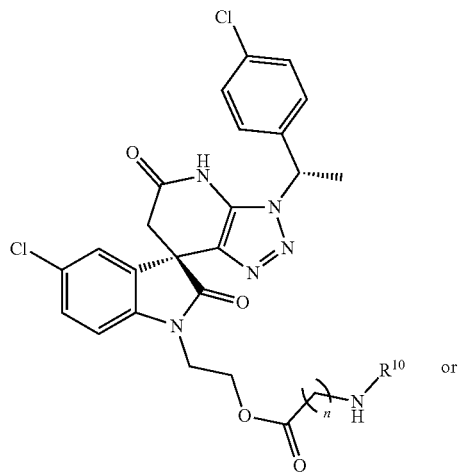
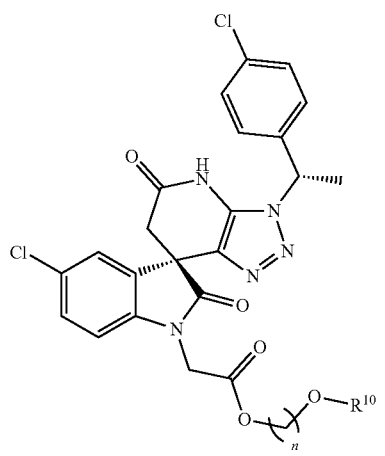
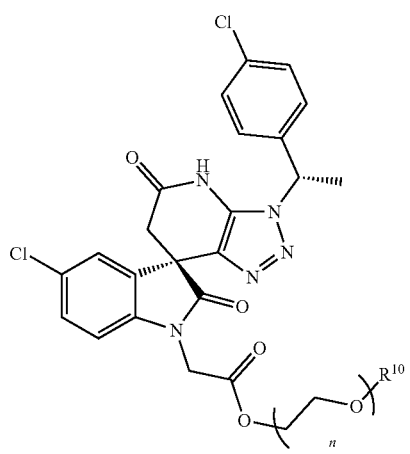
wherein $R^{10}$ is chosen from
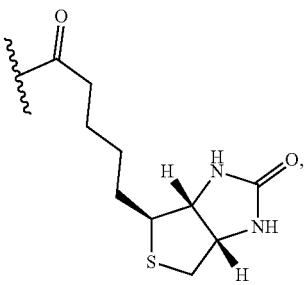
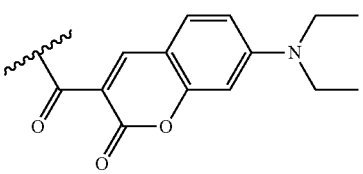
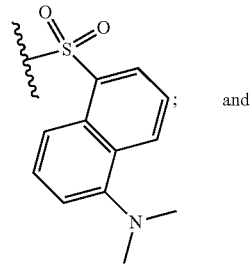
and n is 1-10.
6. A compound represented by:
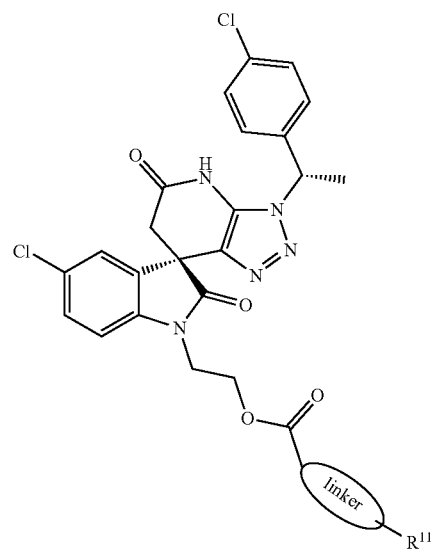

67

-continued

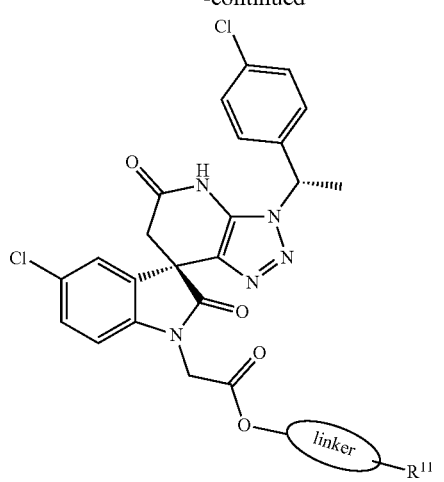

or

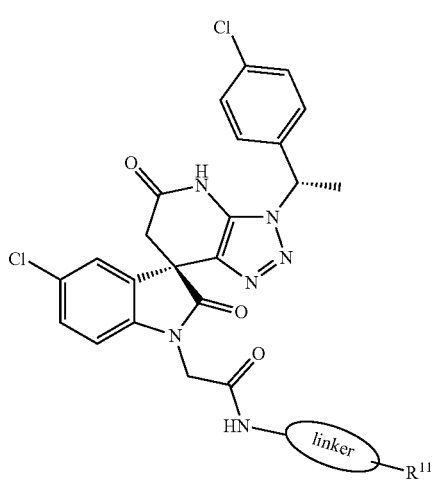

wherein R[11] is chosen from

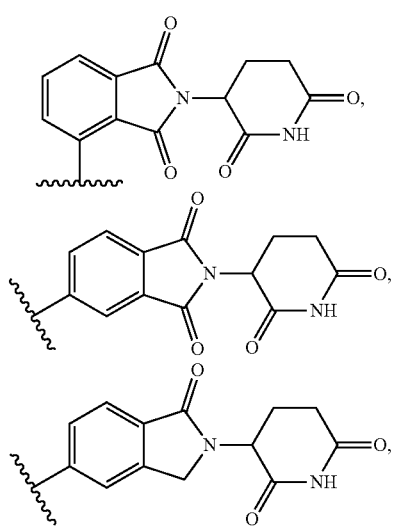

68

-continued

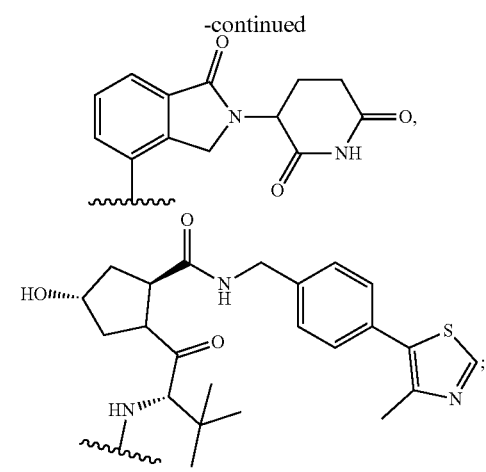

and
linker is a 1-20 atom length carbon chain, wherein said chain optionally includes ester bonds, amide bonds or oxygen atoms.

7. A compound of Formula (II)

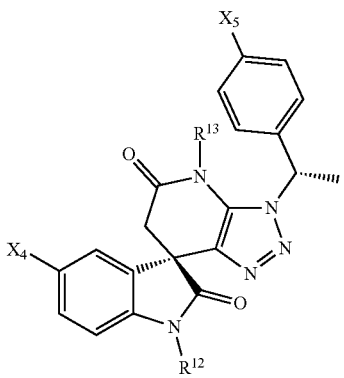

Formula II wherein $X_4$, $X_5$ are independently chosen from F, Cl, Br and $CF_3$; and $R^{12}$, $R^{13}$ are 1-20 atom length carbon chains, which is optionally substituted with one or more ester bonds, amide bonds or oxygen atoms; wherein said chain is tethered to a terminal group chosen from F, Cl, Br, alkyl, alkenyl, alkynyl, alkoxy, hydroxyl, carboxyl, ester, acetal, amino, 5-membered cycle or heterocycle, or 6-membered cycle and heterocycle.

8. The compound according to claim 1, wherein said linker is a 7-20 atom length carbon chain, which is optionally substituted with one or more ester bonds, amide bonds or oxygen atoms; and
wherein $R^4$ is F, Cl, Br, alkyl, alkenyl, alkynyl, alkoxy, hydroxyl, carboxyl, ester, acetal, amino, 5-membered cycle or heterocycle, or 6-membered cycle or heterocycle.

9. The compound according to claim 1, wherein
said linker is a 13-20 atom length carbon chain, which is optionally with substituted one or more ester bonds, amide bonds or oxygen atoms; and
wherein $R^4$ is F, Cl, Br, alkyl, alkenyl, alkynyl, alkoxy, hydroxyl, carboxyl, ester, acetal, amino, 5-membered cycle or heterocycle, or 6-membered cycle or heterocycle.

10. A method of treating dengue disease comprising administering an Dengue NS4B specific inhibitor to a subject having dengue disease, wherein the Dengue NS4B specific inhibitor is a compound of claim 1.

11. The method of claim 10, wherein the dengue disease is severe dengue disease, dengue hemorrhagic fever, or dengue shock syndrome.

12. The method of claim 10, where in the dengue disease is caused by a dengue virus of serotype 1, 2, or 3.

13. The compound according to claim 2, wherein said compound is:

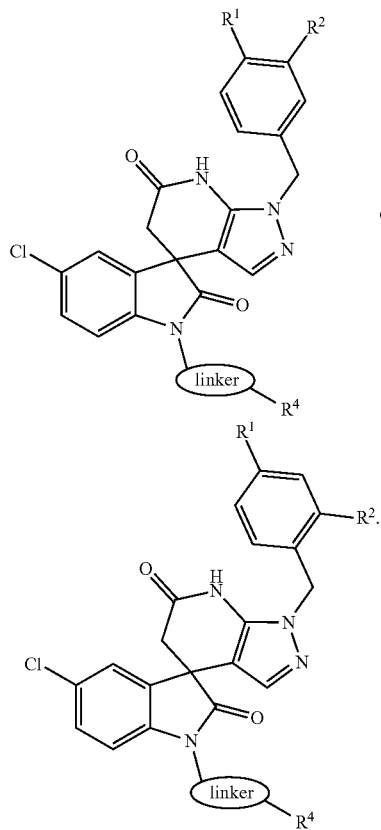

Formula Ib

14. The compound according to claim 3, wherein said compound is:

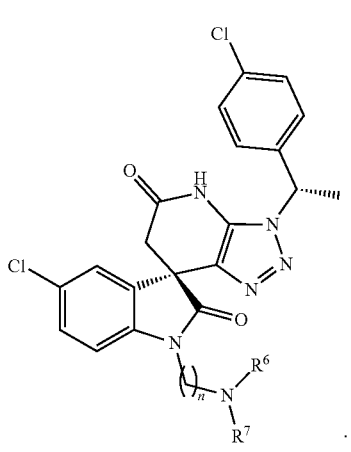

wherein $R^6$, $R^7$ are independently chosen from H and alkyl.

15. The compound according to claim 5, wherein said compound is:

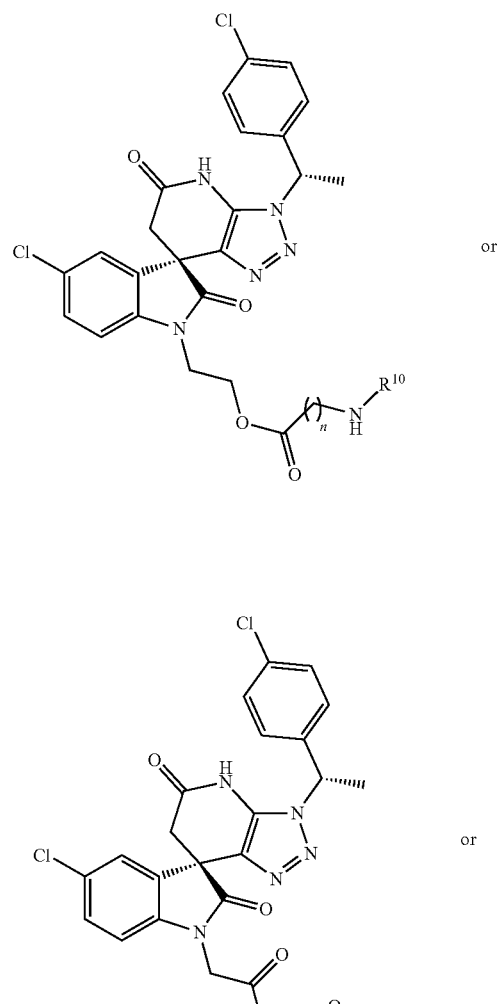

wherein R[10] is
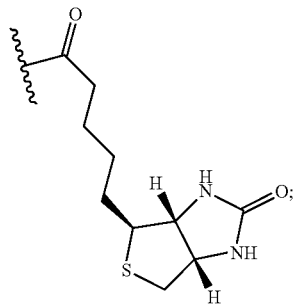 [SMILES: *C(=O)CCCC[C@@H]1SC[C@H]2NC(=O)N[C@@H]12]
and n is 1-10.
16. The compound according to claim 4, wherein said compound is:
Formula Ic
wherein R[8], R[9] is H, alkyl, alkoxy, F, Cl, Br, CF$_3$, hydroxy, carboxyl, ester, cyano, amino, and nitro.
* * * * *